US012377135B2

(12) United States Patent
Mirsaeidi et al.

(10) Patent No.: US 12,377,135 B2
(45) Date of Patent: *Aug. 5, 2025

(54) GHRH ANTAGONISTS FOR USE IN A METHOD OF TREATING SARCOIDOSIS

(71) Applicants: University of Miami, Miami, FL (US); The United States Government as Represented by the Department of Veterans Affairs, Washington, DC (US)

(72) Inventors: Mehdi Mirsaeidi, Jacksonville, FL (US); Chongxu Zhang, Riverside, IL (US); Andrew V. Schally, Miami Beach, FL (US); Renzhi Cai, Miami, FL (US)

(73) Assignees: University of Miami, Miami, FL (US); The United States Government as Represented by the Department Veterans Affairs, Washington, DC (US)

( * ) Notice: Subject to any disclaimer, the term of this patent is extended or adjusted under 35 U.S.C. 154(b) by 749 days.

This patent is subject to a terminal disclaimer.

(21) Appl. No.: 17/648,137

(22) Filed: Jan. 17, 2022

(65) Prior Publication Data

US 2022/0143149 A1     May 12, 2022

Related U.S. Application Data

(63) Continuation of application No. PCT/US2020/042540, filed on Jul. 17, 2020.

(60) Provisional application No. 62/875,703, filed on Jul. 18, 2019.

(51) Int. Cl.
    *A61K 38/25*      (2006.01)
    *A61P 11/00*      (2006.01)

(52) U.S. Cl.
    CPC .............. *A61K 38/25* (2013.01); *A61P 11/00* (2018.01)

(58) Field of Classification Search
None
See application file for complete search history.

(56) References Cited

U.S. PATENT DOCUMENTS

| 4,659,693 | A | 4/1987 | Nester |
| 4,914,189 | A | 4/1990 | Schally et al. |
| 5,084,555 | A | 1/1992 | Coy et al. |
| 5,550,212 | A | 8/1996 | Zarandi et al. |
| 5,942,489 | A | 8/1999 | Schally et al. |
| 6,057,422 | A | 5/2000 | Schally et al. |
| 6,124,263 | A | 9/2000 | Muccioli et al. |
| 7,452,865 | B2 | 11/2008 | Schally et al. |
| 8,227,405 | B2 | 7/2012 | Schally et al. |
| 8,227,421 | B2 | 7/2012 | Schally et al. |
| 8,691,942 | B2 | 4/2014 | Schally et al. |
| 9,260,504 | B2 | 2/2016 | Schally et al. |
| 2007/0042950 | A1 | 2/2007 | Schally et al. |
| 2011/0066230 | A1 | 3/2011 | Schally et al. |
| 2013/0261055 | A1 | 10/2013 | Schally et al. |
| 2014/0206836 | A1 | 7/2014 | Schally et al. |
| 2015/0166617 | A1 | 6/2015 | Schally et al. |
| 2017/0202907 | A1 | 7/2017 | Romero-Lucas |
| 2018/0250358 | A1 | 9/2018 | Schally et al. |
| 2019/0300590 | A1 | 10/2019 | Bhandari |
| 2021/0395327 | A1 | 12/2021 | Jackson et al. |
| 2022/0000983 | A1 | 1/2022 | Jackson et al. |

FOREIGN PATENT DOCUMENTS

| CA | 2733440 | 2/2010 | |
| CN | 1326353 A | 12/2001 | |
| CN | 102170864 | 8/2011 | |
| EP | 2222272 | 11/2012 | |
| EP | 2478011 | 8/2014 | |
| WO | 9116923 | 11/1991 | |
| WO | 9742223 | 11/1997 | |
| WO | 0031136 | 6/2000 | |
| WO | 2005016953 | 2/2005 | |
| WO | 2005113822 | 12/2005 | |
| WO | 2009120831 | 10/2009 | |
| WO | 2010015818 | 2/2010 | |
| WO | 2011034976 | 3/2011 | |
| WO | 2014004934 | 1/2014 | |
| WO | 2019060601 | 3/2019 | |
| WO | 2020163833 | 8/2020 | |
| WO | WO-2020163833 A2 * | 8/2020 | ............ A61K 38/25 |
| WO | 2021011874 | 1/2021 | |
| WO | 2021222129 | 11/2021 | |

OTHER PUBLICATIONS

Barabutis, Nektarios et al: "Antioxidant activity of growth hormone-releasing hormone antagonists in LNCaP human prostate cancer line," PNAS, Dec. 2008, vol. 105, No. 51:20470-20475.

Baughman, Robert P. et al: "A retrospective pilot study examining the use of Acthar gel in sarcoidosis patients," Respiratory Medicine, 2016, vol. 110:66-72.

Baughman, Robert P. et al: "Clinical characteristics of patients in a case control study of sarcoidosis," Am J Respir Crit Care Med, 2001, vol. 164:1885-1889.

Brownell, Isaac et al: "Evidence for mycobacteria in sarcoidosis," Am J Respir Cell Mol Biol, 2011, vol. 45:899-905.

Auerbach, Robert et al: "Angiogenesis assays: Problems and pitfalls," Cancer and Metastasis Review, 2000, vol. 19:167-172.

Cervini, Laura A. et al:"Human Growth Hormone-Releasing Hormone hGHRH(1-29)-NH2: Systematic Structure-Activity Relationship Studies," J. Med. Chem, 1998, vol. 41: 717-727.

Dermer, Gerald B.: "Another Anniversary for the War on Cancer," Biotechnology, 1994, vol. 12: 320.

Gura, Trisha: "Systems for Identifying New Drugs are Often Faulty," Science, 1997, vol. 278, Issue 5340: 1041-1042.

Halmos, Gabor et al.: "Human renal cell carcinoma expresses distinct binding sites for growth hormone-releasing hormone," PNAS, Sep. 2000, vol. 97, No. 19: 10555-10560.

(Continued)

*Primary Examiner* — Christina Bradley

(74) *Attorney, Agent, or Firm* — Stanley A. Kim

(57) ABSTRACT

The disclosure provides a method of treating sarcoidosis, the method comprising administering a GHRH antagonist to mammalian subject in need thereof.

16 Claims, 39 Drawing Sheets

Specification includes a Sequence Listing.

(56) References Cited

OTHER PUBLICATIONS

Jaffe, Craig A. et al.: "Suppression of growth hormone (GH) hypersecretion due to Ectopic GH-releasing hormne (GHRH) by a selective GHRH antagonist," Journal of Clinical Endocrinology and Metabolism, 1996, vol. 82, No. 2: 634-637.
Jain, Rakesh K. et al: "Quantitative angiogenesis assays: Progress and problems," Nature Medicine, 1997, vol. 3, No. 11: 1203-1208.
Kiaris, Hippokratis et al: "Expression of a splice variant of the receptor for GHRH in 3T3 fibroblasts activates cell proliferation responses to GHRH analogs," PNAS, Jan. 2002, vol. 99, No. 1: 196-200.
Klukovits, Anna et al.: "Novel antagonists of growth hormone-releasing hormone inhibit growth and vascularization of human experimental ovarian cancers," Cancer, 2012: 670-680.
Letsch, Markus et a.: "Growth hormone-releasing hormone (GHRH) antagonists inhibit the proliferation of androgen-dependent and-independent prostate cancers," PNAS, Feb. 2003, vol. 100, No. 3: 1250-1255.
Merrifield, R.B.: Solid phase peptide synthesis. I. The synthesis of a tetrapeptide, Syntheisis of a Tetrapeptide, Jul. 1963, vol. 85: 2149-2154.
Perez, Roberto et al.: "Antagonists of growth hormone-releasing hormone suppress in vivo tumor growth and gene expression in triple negative breast cancers," Oncotarget, 2012, vol. 3: 988-997.
Plonowski, Artur et al.: "Inhibition of proliferation of PC-3 human prostrate cancer by antagonists of growth hormone-releasing hormone: Lack of correlation with the levels of serum IGF-I and expression of Tumoral IGF-II and vascular endothelial growth factor," The Prostrate, 2002, vol. 52: 173-182.
Pozsgai, Eva et al.: "The effect of GHRH antagonists on human glioblastomas and their mechanism of action," Int. J. Cancer, 2010, vol. 127: 2313-2322.
Pozsgai, Eva et al.: "The effect of a novel antagonist of growth hormone releasing hormone on cell proliferation and on the key cell signaling pathways in nine different breast cancer cell lines," Int Journal of Oncology, 2011, vol. 39: 1025-1032.
Rekasi, Zoltan et al.: "Antagonists of growth hormone-releasing hormone and vasoactive intestinal peptide inhibit tumor proliferation by different mechanisms: Evidence from in vitro studies on human prostatic and pancreatic cancers," Endocrinology, 2000, vol. 141, No. 6: 2120-2128.
Rekasi, Zoltan et al.: "Islolation and sequencing of cDNAs for splice variants of growth hormone-releasing hormone receptors from human cancers," PNAS, Sep. 2000, vol. 97, No. 19: 10561-10566.
Schally, Andrew V. et al.: "Antagonistic analogs of growth hormone-releasing hormone: New potential antitumor agents," TEM, 1999, vol. 10, No. 10: 383-391.
Schally, Andrew V. et al.: "Hypothalamic hormones and cancer," Frontiers in Neuroendocrinology, 2002, vol. 22: 248-291.
Schally, Andrew V. et al.: "Antagonists of growth hormone-releasing hormone in oncology," Combinatorial Chemistry & High Throughput Screening, 2006, vol. 9: 163-170.
Siejka, A. et al.: "GH-RH antagonist (MZ-4-71) inhibits VEGF secretion and proliferation of murine endothelial cells," Life Sciences, 2003, vol. 72: 2473-2479.
Szepeshazi, Karoly et al.: "Antagonists of GHRH decrease production of GH and IGF-I in MXT mouse mammary cancers and inhibit tumor growth," Endocrinology, 2001, vol. 14: 4371-4378.
Szereday, Zoltan et al.: "Antagonists of growth hormone-releasing hormone inhibit the proliferation of experimental non-small cell lung carcinoma," Cancer Research, 2003, vol. 63: 7913-7919.
Toth, Katalin et al.: "New analogs of human growth hormone-releasing hormone (1-29) with high and prolonged antagonistic activity," J. Peptide Res., 1998, vol. 51: 134-141.
Varga, Jozsef L. et al.: "Synthesis and biological evaluation of antagonists of growth hormone-releasing hormone with high and protracted in vivo activities," Proc. Natl. Acad. Sci., 1999, vol. 96: 692-697.
Varga, Jozsef L. et al.: "Increased activity of antagonists of growth hormone-releasing hormone substituted at positions 8, 9, and 10," PNAS, Feb. 2004, vol. 101, No. 6: 1708-1713.
Voskoglou-Nomikos, Theodora et al.: "Clinical predictive value of the in vitro cell line, human xenograft, and mouse allograft preclinical cancer models," Clinical Cancer Research, 2003, vol. 9: 4227-4239.
Zarandi, Marta et al.: "Potent agonists of growth hormone-releasing hormone," Int. J. Peptide Protein Res., 1992, vol. 39: 211-217.
Zarandi, M. et al.: "Synthesis and biological activities of highly potent antagonists of growth hormone-releasing hormone," Proc. Natl. Acad. Sci., 1994 vol. 91: 12298-12302.
"Restenosis Treatment," web page , <https://www/news-medical.net/health/Restenosis-Treatment.aspx>, 7 pages, retrieved from website on Mar. 18, 2022.
Cabrera, Sandra et al.: "Gene expression profiles reveal molecular mechanisms involved in the progression and resolution of bleomycin-induced lung fibrosis," Am J Physiol Lung Cell Mol Physiol, 2013, vol. 304: 593-601.
Chen, Edward S. et al.: "Etiology of sarcoidosis," Clin Chest Med, 2008, vol. 29: 365-377.
Cui, Tengjiao et al.: "Agonistic analogs of growth hormone releasing hormone (GHRH) promote wound healing by stimulating the proliferation and survival of human dermal fibroblasts through ERK and AKT pathways," Aug. 2016, Oncotarget, vol. 7, No. 33: 52661-52672.
Dubaniewicz, Anna et al.: "*Mycobacterium tuberculosis* complex and mycobacterial heat shock proteins in lymph node tissue from patient with pulmonary sarcoidosis," Journal of Clinical Microbiology, 2006, vol. 44, No. 9: 3448-3451.
Elhai, Muriel et al.: "OX40L blockade protects against inflammation-driven fibrosis," PNAS, Jun. 2016: E3901-E3910.
Facchetti, Fabio et al.: "Expression of Inducible nitric oxide synthase in human granulomas and histiocytic reactions," American Journal of Pathology, Jan. 1999, vol. 154, No. 1: 145-152.
Fu, Yung-Kang et al.: "A novel role of growth hormone and insulin-like growth factor-1," The Journal of Immunology, 1991 vol. 146: 1602-1608.
Havt, Alexandre et al.: "The expression of the pituitary growth hormone-releasing hormone receptor and its splice variants in normal and neoplastic human tissues," PNAS, Nov. 2005, vol. 102, No. 48: 17424-17429.
Huang, Xinqiang et al.: "Molecular characterization of a precision-cut rat lung slice model for the evaluation of antifibrotic drugs," Am J Physiol Lung Cell Mol Physiol, 2019, vol. 316: L348-L357.
Jenkins, R. Gisli et al.: "An official american thoracic society workshop report: Use of animal models for the preclinical assessment of potential therapies for pulmonary fibrosis," Am J Respir Cell Mol Biol, 2017, vol. 56, No. 5: 667-679.
Koh, Timothy J. et al.: "Inflammation and wound healing: the role of the macrophage," Expert Review in Molecular Medcine, Jul. 2011, vol. 13, e23: 1-12.
Kral, Julia Barbara et al.: "Sustained PI3K Activation exaerbates BLM-induced lung fibrosis via activation of pro-inflammatory and pro-fibrotic pathways," Scientific Reports, Mar. 2016, pp. 1-16.
Kucera, Gena P. et al.: "Occupational risk factors for sarcoidosis in African-American siblings," Chest, May 2003, vol. 5: 1527-1535.
Lazarus, Angeline: "Sarcoidosis: Epidemiology, etiology, pathogenesis, and genetics," DM, Nov. 2009: 649-660.
Miller, Milton A. et al.: "Effect of acthar-c (ACTH) in sarcoidosis," Case Reports, Feb. 1952:776-784.
Mirsaeidi, Mehdi et al.: "Racial difference in sarcoidosis mortality in the United States," Chest, Feb. 2015, vol. 147, No. 2: 438-449.
Rutherford, Robert et al.: "Mycobacteria in Pathogenesis of Sarcoidosis," Chest., 2004; 125(1):354.
Fang, Chuling, et al.: "Immunological Evidence for the Role of Mycobacteria in Sarcoidosis: A Meta-Analysis," PLOS ONE, 2016, No. 10:1-14.
Iannuzzi, Michael C. et al.: "Sarcoidosis," The New England Journal of Medicine, 2007, No. 357:2153-2165.
Newman, Lee S. et al.: "A case control etiologic study of sarcoidosis," Am J Respir Crit Care Med, 2004, vol. 170: 1324-1330.

(56) References Cited

OTHER PUBLICATIONS

Nunes, Hilario et al.: Sarcoidosis, Orphanet Journal of Rare Diseases, 2007, vol. 2, No. 46: 1-8.
Ocampo-Lin, Blanca et al.: "Nocturnal growth hormone (GH) secretion is eliminated by infusion of GH-releasing hormone antagonist," Journal of Clinical Endocrinology and Metabolism, 1996, vol. 81, No. 12: 4396-4399.
Oswald-Richter, Kyra A. et al.: "Dual analysis for mycobacteria and propionibacteria in sarcoidosis BAL," J Clin Immunol, 2012, vol. 32: 1129-1140.
Patterson, Karen C. et al.: "Pulmonary fibrosis in sarcoidosis," Ann Am Thorac Soc, Aug. 2013, vol. 10, No. 4: 362-370.
Ren, Jia Lin et al.: "Growth hormone-releasing hormone receptor mediates cytokine production in ciliary and iris epithelial cells during LPS-induced ocular inflammation," Experimental Eye Research, 2019, vol. 181: 277-284.
Ryter Stefan W. et al.: "Mitochondrial dysfunction as a pathogenic mediator of chronic obstructive pulmonary disease and idiopathic pulmonary fibrosis," Ann Am Thorac Soc, Dec. 2018, vol. 15, Supplement 4: S266-S272.
Hung, Chi F. et al.: "Role of IGF-1 pathway in lung fibroblast activation," Respiratory Research, 2013, vol. 14: 102, pp. 1-11.
Schally, Andrew V. et al.: "Hypothalamic and other peptide hormones," Endocrine Therapy, 2003, Section 14: 911-926.
Simonian, Philip L. et al.: "Regulatory role of γδ T cells in the recruitment of CD4+ and CD8+ T cells to lung and subsequent pulmonary fibrosis," The Journal of Immunology, 2006, vol. 177: 4436-4443.
Bellyei, Szabolcs et al.: "GHRH antagonists reduce the invasive and metastatic potential of human cancer cell lines in vitro," Cancer Letters, 2010, vol. 293: 31-40.
Warwick-Davies, Jan et al.: "Growth hormone is a human macrophage activating factor," The Journal of Immunology, 1995, vol. 154: 1909-1918.
Waters, David W. et al.: "STAT3 regulates the onset of oxidant-induced senescence in lung fibroblasts," Am J Respir Cell Mol Biol, 2019, vol. 61, Issue No. 1: 61-73.
Zarandi, Marta et al.: "Synthesis and structure-activity studies on novel analogs of human growth hormone releasing hormone (GHRH) with enhanced inhibitory activities on tumor growth," Peptides, 2017, vol. 89: 60-70.
Zhang, Chongxu et al.: "Growth hormone-releasing hormone receptor antagonist modulates lung inflammation and fibrosis due to bleomycin," Lung, 2019, vol. 197: 541-549.
Chen, Edward et al.: "Serum amyloid A regulates granulomatous inflammation in sarcoidosis through toll-like receptor-2," Am J Respir Crit Care Med, 2010, vol. 181: 360-373.
Gan, Jinfeng et al.: Growth hormone-releasing hormone receptor antagonists inhibit human gastric cancer through downregulation of PAK1-STAT3/NF-κB signaling, PNAS, 2016, vol. 113, No. 51: 14745-14550.
Jackson, Robert M. et al.: "Growth hormone-releasing hormone receptor antagonist MIA-602 modulates mouse lung inflammation and fibrosis due to bleomycin," European Respiratory journal, 2018, 52 Suppl. 62:1-2; (Only Abstract—No Full-Text Version is Available).
Cleveland Clinic: Pulmonary Fibrosis, <https://my.clevelandclinic.org/health/diseases/10959-pulmonary-fibrosis#symptoms-and-causes>, accessed online on Jul. 26, 2023.
Qin, Yong Jie et al., "Antagonist of GH-releasing hormone receptors alleviates experimental ocular inflammation," PNAS, 2014, vol. 111, No. 51:18303-18308.
Kono, Keiko, "Eye Lesion of Sarcoidosis, the Therapy and Adult Disease," Lifestyle-Related Disease, 2023, 43rd vol., No. 10:1229-1233.

* cited by examiner

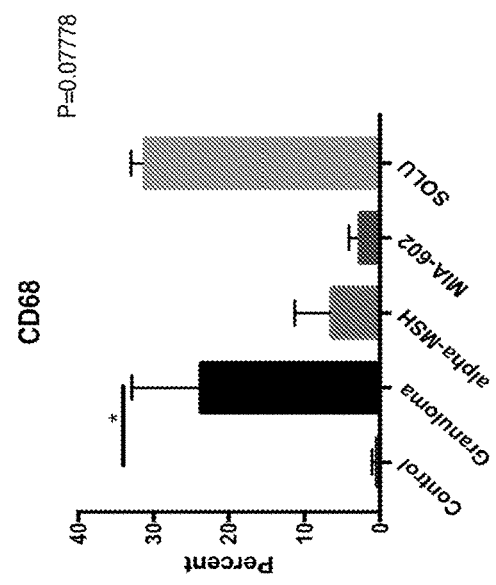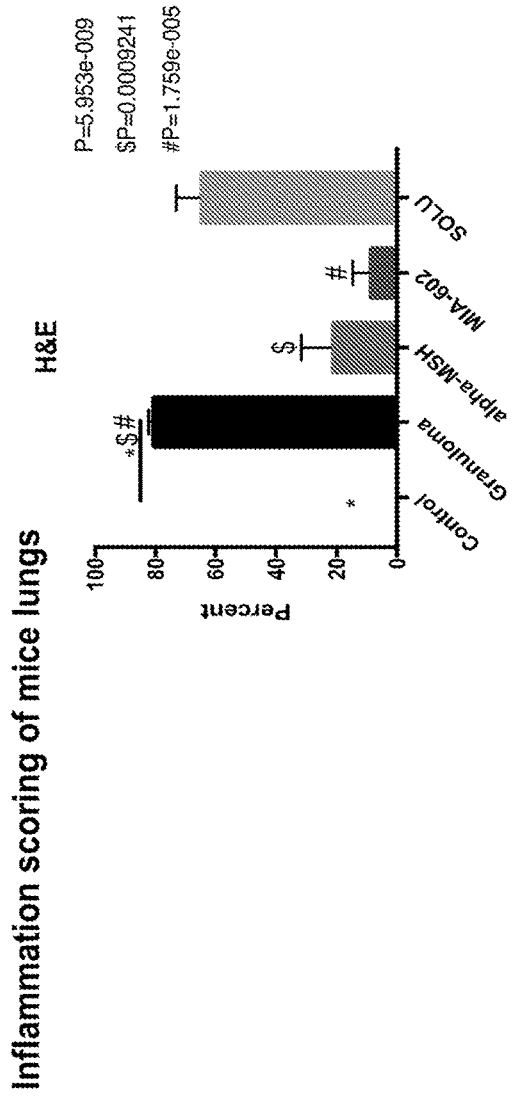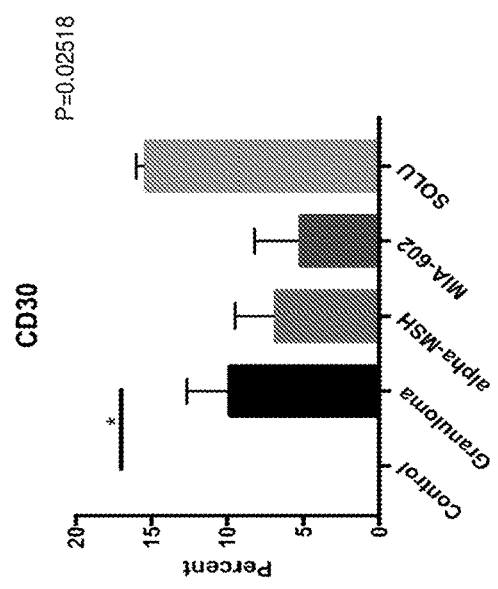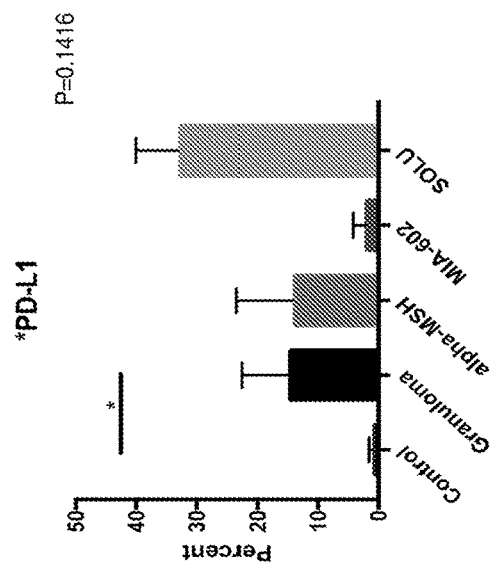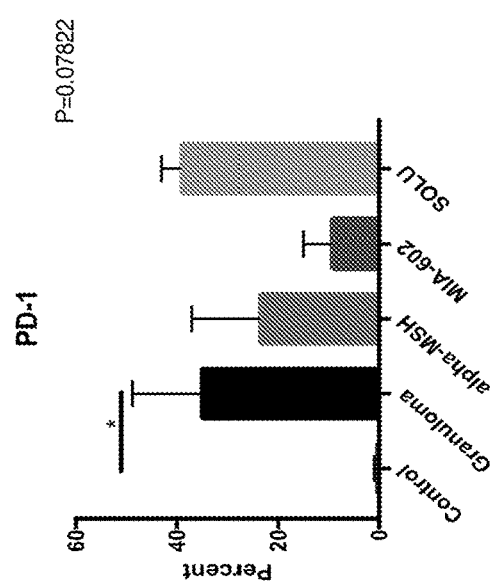

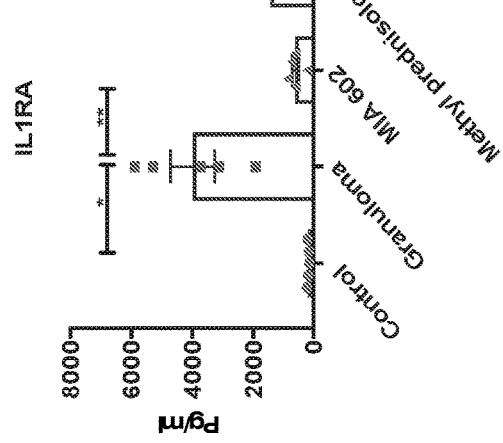
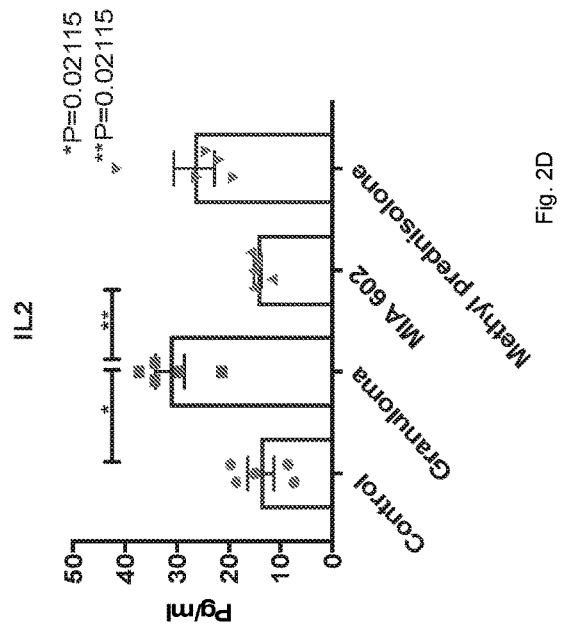
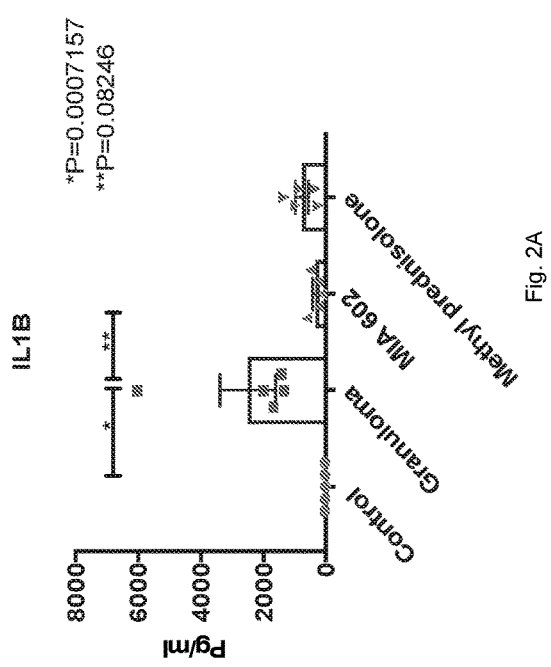
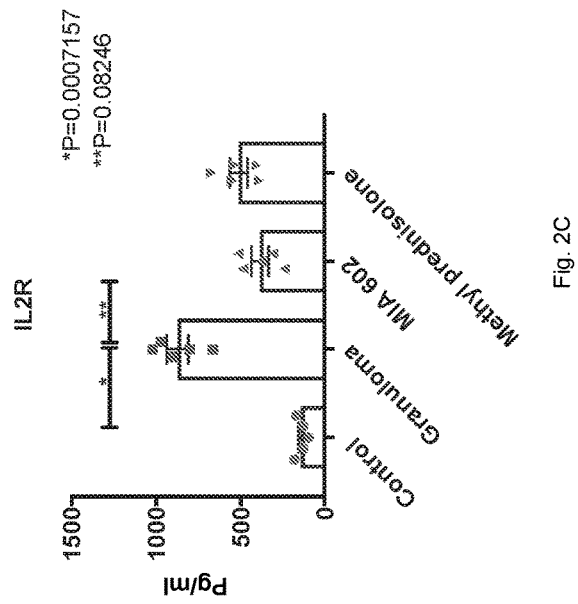
Fig. 2A
Fig. 2B
Fig. 2C
Fig. 2D

| Stable Identifier (Ensembl Ref.) | Gene Name | Type |
|---|---|---|
| ENSMUSG00000086602 | "Gm15609" | processed_transcript |
| ENSMUSG00000085664 | "Atxn7l1os2" | antisense_RNA |
| ENSMUSG00000093906 | "Igkv9-129" | IG_V_gene |
| ENSMUSG00000107999 | "Gm44123" | antisense_RNA |
| ENSMUSG00000016998 | "Svs4" | protein_coding |
| ENSMUSG00000065084 | "Gm26496" | snRNA |
| ENSMUSG00000110608 | "Gm8838" | processed_pseudogene |
| ENSMUSG00000114690 | "AC162183.1" | lincRNA |
| ENSMUSG00000095866 | "Ighv2-4" | IG_V_gene |
| ENSMUSG00000115548 | "AC138716.2" | lincRNA |
| ENSMUSG00000095957 | "Olfr832" | protein_coding |
| ENSMUSG00000058186 | "Zfp980" | protein_coding |
| ENSMUSG00000097833 | "Gm5976" | processed_pseudogene |
| ENSMUSG00000106367 | "Gm34078" | lincRNA |
| ENSMUSG00000105875 | "Gm43518" | protein_coding |
| ENSMUSG00000110638 | "Gm45887" | TEC |
| ENSMUSG00000104443 | "4932442E05Rik" | TEC |
| ENSMUSG00000113540 | "AC160931.3" | TEC |
| ENSMUSG00000091283 | "Gm17234" | antisense_RNA |
| ENSMUSG00000036800 | "Fam135b" | protein_coding |
| ENSMUSG00000087552 | "Gm15819" | antisense_RNA |
| ENSMUSG00000086222 | "Gm11665" | antisense_RNA |
| ENSMUSG00000096515 | "Igkv14-100" | IG_V_gene |
| ENSMUSG00000095477 | "Gm25076" | snoRNA |
| ENSMUSG00000113387 | "AC162181.1" | lincRNA |
| ENSMUSG00000097686 | "Gm26647" | antisense_RNA |
| ENSMUSG00000103255 | "Pcdhac1" | protein_coding |
| ENSMUSG00000106589 | "4931419H13Rik" | antisense_RNA |
| ENSMUSG00000064299 | "4921528I07Rik" | processed_transcript |
| ENSMUSG00000087693 | "Gm16191" | antisense_RNA |
| ENSMUSG00000109647 | "Gm45510" | antisense_RNA |
| ENSMUSG00000101800 | "Rnf170-ps" | processed_pseudogene |
| ENSMUSG00000045341 | "Olfr167" | protein_coding |
| ENSMUSG00000065418 | "Mir322" | miRNA |
| ENSMUSG00000080817 | "Gm13751" | processed_pseudogene |
| ENSMUSG00000081041 | "Nlk-ps1" | processed_pseudogene |
| ENSMUSG00000104788 | "Gm36448" | unprocessed_pseudogene |

Fig. 9

| | | |
|---|---|---|
| ENSMUSG00000092928 | "Gm24563" | miRNA |
| ENSMUSG00000089814 | "Gm15310" | transcribed_processed_pseudogene |
| ENSMUSG00000014351 | "Gip" | protein_coding |
| ENSMUSG00000053211 | "Zfy1" | protein_coding |
| ENSMUSG00000114504 | "AC154681.1" | antisense_RNA |
| ENSMUSG00000111006 | "Gm10826" | TEC |
| ENSMUSG00000106630 | "Igkv2-116" | IG_V_pseudogene |
| ENSMUSG00000096793 | "Gm3002" | protein_coding |
| ENSMUSG00000073781 | "Gm6471" | lincRNA |
| ENSMUSG00000112162 | "AC155929.2" | processed_pseudogene |
| ENSMUSG00000115125 | "AC101205.1" | processed_pseudogene |
| ENSMUSG00000077607 | "Gm25803" | snoRNA |
| ENSMUSG00000036449 | "Lcn8" | protein_coding |
| ENSMUSG00000094198 | "Ighv1-50" | IG_V_gene |
| ENSMUSG00000065417 | "Mir340" | miRNA |
| ENSMUSG00000110523 | "C230057M02Rik" | lincRNA |
| ENSMUSG00000022243 | "Slc45a2" | protein_coding |
| ENSMUSG00000106824 | "Gm7697" | protein_coding |
| ENSMUSG00000056755 | "Grm7" | protein_coding |
| ENSMUSG00000045174 | "Amer3" | protein_coding |
| ENSMUSG00000086205 | "Gm12679" | antisense_RNA |
| ENSMUSG00000111447 | "AC153845.2" | antisense_RNA |
| ENSMUSG00000084979 | "Gm16267" | lincRNA |
| ENSMUSG00000083372 | "Gm11235" | processed_pseudogene |
| ENSMUSG00000095737 | "Igkv11-125" | IG_V_gene |
| ENSMUSG00000072664 | "Ugt3a1" | protein_coding |
| ENSMUSG00000113201 | "Gm21936" | protein_coding |
| ENSMUSG00000072592 | "Gm10373" | lincRNA |
| ENSMUSG00000076666 | "Ighv14-4" | IG_V_gene |
| ENSMUSG00000045648 | "Vwc2l" | protein_coding |
| ENSMUSG00000080334 | "Gm25110" | miRNA |
| ENSMUSG00000111268 | "AC121264.1" | bidirectional_promoter_lncRNA |
| ENSMUSG00000114498 | "AC126275.1" | processed_pseudogene |
| ENSMUSG00000096824 | "Ighv2-7" | IG_V_gene |
| ENSMUSG00000110989 | "Gm7444" | processed_pseudogene |
| ENSMUSG00000045967 | "Gpr158" | protein_coding |
| ENSMUSG00000112989 | "AC164556.1" | processed_pseudogene |
| ENSMUSG00000044286 | "Olfr221" | protein_coding |
| ENSMUSG00000108290 | "Gm44120" | TEC |

Fig. 9 contd.

| | | |
|---|---|---|
| ENSMUSG00000101784 | "Gm7553" | processed_pseudogene |
| ENSMUSG00000065040 | "Gm24977" | snRNA |
| ENSMUSG00000109711 | "Gm45445" | processed_pseudogene |
| ENSMUSG00000072731 | "Gm3715" | unprocessed_pseudogene |
| ENSMUSG00000097621 | "Gm26562" | lincRNA |
| ENSMUSG00000101433 | "Gm29441" | processed_pseudogene |
| ENSMUSG00000113579 | "AC122327.2" | processed_pseudogene |
| ENSMUSG00000080574 | "Mir466i" | miRNA |
| ENSMUSG00000102940 | "Gm37551" | TEC |
| ENSMUSG00000102868 | "Gm37633" | TEC |
| ENSMUSG00000106906 | "Gm34728" | lincRNA |
| ENSMUSG00000103904 | "Gm37497" | TEC |
| ENSMUSG00000092364 | "Gm20476" | antisense_RNA |
| ENSMUSG00000103521 | "Gm29730" | processed_pseudogene |
| ENSMUSG00000081330 | "Gm13013" | processed_pseudogene |
| ENSMUSG00000110781 | "Gm31992" | lincRNA |
| ENSMUSG00000086248 | "Gm16127" | processed_transcript |
| ENSMUSG00000083238 | "Hspe1-ps4" | processed_pseudogene |
| ENSMUSG00000106641 | "Gm43534" | TEC |
| ENSMUSG00000113257 | "Gm30409" | sense_intronic |
| ENSMUSG00000073964 | "Olfr570" | protein_coding |
| ENSMUSG00000074946 | "Olfr1313" | protein_coding |
| ENSMUSG00000104096 | "Gm20356" | lincRNA |
| ENSMUSG00000024992 | "Pde6c" | protein_coding |
| ENSMUSG00000097682 | "4930554H23Rik" | lincRNA |
| ENSMUSG00000107483 | "Gm44288" | TEC |
| ENSMUSG00000031884 | "Ces2d-ps" | unprocessed_pseudogene |
| ENSMUSG00000103082 | "Gm38124" | TEC |
| ENSMUSG00000086932 | "Gm22000" | processed_transcript |
| ENSMUSG00000101286 | "Gm21317" | protein_coding |
| ENSMUSG00000080849 | "Gm15702" | processed_pseudogene |
| ENSMUSG00000083065 | "Gm13195" | processed_pseudogene |
| ENSMUSG00000110084 | "Gm45257" | TEC |
| ENSMUSG00000085835 | "Gm12707" | processed_transcript |
| ENSMUSG00000087358 | "4930453H23Rik" | lincRNA |
| ENSMUSG00000058626 | "Capn11" | protein_coding |
| ENSMUSG00000046774 | "8030474K03Rik" | protein_coding |
| ENSMUSG00000075586 | "Gm11529" | processed_transcript |
| ENSMUSG00000084911 | "Gm16185" | antisense_RNA |

Fig. 9 contd.

| | | |
|---|---|---|
| ENSMUSG00000091771 | "Vmn2r103" | protein_coding |
| ENSMUSG00000101468 | "Gm7761" | processed_pseudogene |
| ENSMUSG00000102801 | "Gm37478" | TEC |
| ENSMUSG00000111085 | "Gm7607" | lincRNA |
| ENSMUSG00000097435 | "Gm26783" | lincRNA |
| ENSMUSG00000111815 | "Gm6018" | processed_pseudogene |
| ENSMUSG00000093223 | "Gm27903" | miRNA |
| ENSMUSG00000061707 | "Gm4871" | protein_coding |
| ENSMUSG00000108151 | "Gm33201" | lincRNA |
| ENSMUSG00000088964 | "Gm22087" | snRNA |
| ENSMUSG00000114246 | "AC102542.1" | TEC |
| ENSMUSG00000070489 | "4930527J03Rik" | processed_transcript |
| ENSMUSG00000113814 | "Gm9255" | unprocessed_pseudogene |
| ENSMUSG00000113084 | "A030003K21Rik" | protein_coding |
| ENSMUSG00000089759 | "3632454L22Rik" | processed_transcript |
| ENSMUSG00000097871 | "B230104I21Rik" | protein_coding |
| ENSMUSG00000085858 | "Gm15831" | lincRNA |
| ENSMUSG00000053862 | "Slc51b" | protein_coding |
| ENSMUSG00000047384 | "A730013G03Rik" | TEC |
| ENSMUSG00000106426 | "Gm36211" | lincRNA |
| ENSMUSG00000104240 | "Gm36858" | unprocessed_pseudogene |
| ENSMUSG00000092097 | "Gm5819" | protein_coding |
| ENSMUSG00000104414 | "Gm37799" | lincRNA |
| ENSMUSG00000103594 | "A430034D21Rik" | lincRNA |
| ENSMUSG00000111655 | "4930434F21Rik" | bidirectional_promoter_lncRNA |
| ENSMUSG00000073173 | "Gm10477" | protein_coding |
| ENSMUSG00000075218 | "Olfr995" | protein_coding |
| ENSMUSG00000073103 | "Gm10466" | lincRNA |
| ENSMUSG00000080729 | "Gm8084" | unprocessed_pseudogene |
| ENSMUSG00000080744 | "Gm12710" | processed_pseudogene |
| ENSMUSG00000089576 | "Gm23007" | misc_RNA |
| ENSMUSG00000092832 | "Mir3088" | miRNA |
| ENSMUSG00000095093 | "Vmn2r111" | protein_coding |
| ENSMUSG00000097117 | "Gm26730" | lincRNA |
| ENSMUSG00000097783 | "Gm26747" | lincRNA |
| ENSMUSG00000098186 | "Gm7132" | processed_pseudogene |
| ENSMUSG00000113037 | "Gm36550" | antisense_RNA |
| ENSMUSG00000089348 | "Gm22669" | misc_RNA |
| ENSMUSG00000106004 | "Gm43391" | antisense_RNA |

Fig. 9 contd.

| | | |
|---|---|---|
| ENSMUSG00000108696 | "Gm5738" | processed_pseudogene |
| ENSMUSG00000076287 | "Gm24273" | miRNA |
| ENSMUSG00000082160 | "Gm11578" | processed_pseudogene |
| ENSMUSG00000094478 | "Igkv3-3" | IG_V_gene |
| ENSMUSG00000106663 | "Gm42839" | antisense_RNA |
| ENSMUSG00000113336 | "Gm16497" | lincRNA |
| ENSMUSG00000099162 | "Gm27168" | lincRNA |
| ENSMUSG00000081594 | "Gm15467" | processed_pseudogene |
| ENSMUSG00000112643 | "Gm19688" | processed_pseudogene |
| ENSMUSG00000085486 | "Gm11634" | protein_coding |
| ENSMUSG00000107307 | "Gm42935" | processed_pseudogene |
| ENSMUSG00000062732 | "Lypd4" | protein_coding |
| ENSMUSG00000109795 | "Gm45522" | processed_pseudogene |
| ENSMUSG00000099071 | "Mir8095" | miRNA |
| ENSMUSG00000068600 | "Gml2" | protein_coding |
| ENSMUSG00000076533 | "Igkv4-90" | IG_V_gene |
| ENSMUSG00000103908 | "Gm37502" | lincRNA |
| ENSMUSG00000079539 | "Obp2b" | protein_coding |
| ENSMUSG00000111318 | "AC158630.1" | lincRNA |
| ENSMUSG00000071763 | "4933416I08Rik" | unprocessed_pseudogene |
| ENSMUSG00000084010 | "Gm13302" | unprocessed_pseudogene |
| ENSMUSG00000109867 | "Gm5338" | processed_pseudogene |
| ENSMUSG00000114268 | "AC154515.1" | processed_pseudogene |
| ENSMUSG00000115014 | "AC113031.1" | processed_pseudogene |
| ENSMUSG00000046934 | "Csl" | protein_coding |
| ENSMUSG00000087768 | "Gm22755" | snRNA |
| ENSMUSG00000105258 | "Gm40038" | lincRNA |
| ENSMUSG00000086689 | "Gm16876" | antisense_RNA |
| ENSMUSG00000083803 | "Gm12455" | processed_pseudogene |
| ENSMUSG00000093528 | "Nrg3os" | antisense_RNA |
| ENSMUSG00000101234 | "1700007E05Rik" | transcribed_processed_pseudogene |
| ENSMUSG00000076573 | "Igkv1-35" | IG_V_gene |
| ENSMUSG00000056219 | "Tmem229b-ps" | processed_pseudogene |
| ENSMUSG00000112159 | "AC160031.1" | processed_pseudogene |
| ENSMUSG00000106554 | "Gm33474" | lincRNA |
| ENSMUSG00000096978 | "Gm26851" | lincRNA |
| ENSMUSG00000093493 | "Vmn2r-ps133" | unprocessed_pseudogene |
| ENSMUSG00000091697 | "Eif3s6-ps2" | processed_pseudogene |
| ENSMUSG00000102962 | "Gm37944" | IG_C_pseudogene |

Fig. 9 contd.

| | | |
|---|---|---|
| ENSMUSG00000113138 | "AC133083.2" | lincRNA |
| ENSMUSG00000110749 | "AC160123.1" | lincRNA |
| ENSMUSG00000075480 | "Gm10840" | protein_coding |
| ENSMUSG00000041138 | "Nme8" | protein_coding |
| ENSMUSG00000108040 | "Gm43900" | TEC |
| ENSMUSG00000092909 | "Gm25732" | miRNA |
| ENSMUSG00000087640 | "Gm14798" | antisense_RNA |
| ENSMUSG00000071015 | "Gm136" | protein_coding |
| ENSMUSG00000096365 | "Olfr1463" | protein_coding |
| ENSMUSG00000113926 | "Gm3565" | processed_pseudogene |
| ENSMUSG00000094789 | "Gm28490" | protein_coding |
| ENSMUSG00000100204 | "Gm4849" | processed_pseudogene |
| ENSMUSG00000106044 | "Gm42860" | TEC |
| ENSMUSG00000105418 | "Gm43650" | antisense_RNA |
| ENSMUSG00000106016 | "Igkv4-56" | IG_V_pseudogene |
| ENSMUSG00000062705 | "Tpbpb" | protein_coding |
| ENSMUSG00000055761 | "Nkain3" | protein_coding |
| ENSMUSG00000074681 | "Defb23" | protein_coding |
| ENSMUSG00000075598 | "Smok3c" | protein_coding |
| ENSMUSG00000104066 | "Gm37955" | TEC |
| ENSMUSG00000073965 | "Olfr568" | protein_coding |
| ENSMUSG00000105035 | "Gm9682" | processed_pseudogene |
| ENSMUSG00000085176 | "Gm15397" | sense_intronic |
| ENSMUSG00000091749 | "Tspy-ps" | transcribed_unprocessed_pseudogene |
| ENSMUSG00000105002 | "Mir6375" | miRNA |
| ENSMUSG00000106939 | "Gm29778" | processed_pseudogene |
| ENSMUSG00000086402 | "Gm15322" | lincRNA |
| ENSMUSG00000107969 | "Gm44085" | antisense_RNA |
| ENSMUSG00000044518 | "Foxe3" | protein_coding |
| ENSMUSG00000082341 | "Gm14143" | processed_pseudogene |
| ENSMUSG00000085533 | "Gm12146" | antisense_RNA |
| ENSMUSG00000086815 | "3110082J24Rik" | protein_coding |
| ENSMUSG00000087294 | "Gm13556" | antisense_RNA |
| ENSMUSG00000089590 | "Gm26160" | snRNA |
| ENSMUSG00000098233 | "Gm26954" | antisense_RNA |
| ENSMUSG00000100161 | "Gm28445" | lincRNA |
| ENSMUSG00000107922 | "Gm44285" | processed_pseudogene |
| ENSMUSG00000051638 | "Gm9857" | protein_coding |
| ENSMUSG00000086767 | "Gm13070" | antisense_RNA |

Fig. 9 contd.

| | | |
|---|---|---|
| ENSMUSG00000081522 | "Gm13170" | processed_pseudogene |
| ENSMUSG00000105802 | "Gm43012" | TEC |
| ENSMUSG00000114887 | "CT030194.2" | processed_pseudogene |
| ENSMUSG00000101036 | "Gm28588" | antisense_RNA |
| ENSMUSG00000104607 | "Gm31651" | lincRNA |
| ENSMUSG00000086409 | "Gm13898" | processed_pseudogene |
| ENSMUSG00000080050 | "Gm14864" | processed_pseudogene |
| ENSMUSG00000102762 | "4930403P22Rik" | lincRNA |
| ENSMUSG00000108855 | "Gm44917" | processed_pseudogene |
| ENSMUSG00000045004 | "Spata21" | protein_coding |
| ENSMUSG00000115180 | "AC154738.3" | lincRNA |
| ENSMUSG00000030463 | "4933421I07Rik" | protein_coding |
| ENSMUSG00000114522 | "CT025552.1" | lincRNA |
| ENSMUSG00000083421 | "Gm14776" | processed_pseudogene |
| ENSMUSG00000081854 | "Gm11447" | processed_pseudogene |
| ENSMUSG00000104668 | "Vmn2r-ps24" | processed_pseudogene |
| ENSMUSG00000109196 | "Gm44715" | processed_pseudogene |
| ENSMUSG00000113854 | "Gm2099" | transcribed_processed_pseudogene |
| ENSMUSG00000102855 | "Gm38002" | processed_pseudogene |
| ENSMUSG00000094035 | "Ldlrad2" | protein_coding |
| ENSMUSG00000104796 | "Gm44354" | miRNA |
| ENSMUSG00000093751 | "Gm3307" | processed_pseudogene |
| ENSMUSG00000022738 | "Gsc2" | protein_coding |
| ENSMUSG00000074375 | "Sult2a3" | protein_coding |
| ENSMUSG00000081274 | "Gm15727" | processed_pseudogene |
| ENSMUSG00000086792 | "Gm12364" | antisense_RNA |
| ENSMUSG00000089790 | "Gm16588" | processed_pseudogene |
| ENSMUSG00000103201 | "Gm37329" | TEC |
| ENSMUSG00000103351 | "Gm6350" | processed_pseudogene |
| ENSMUSG00000105249 | "Gm44458" | miRNA |
| ENSMUSG00000106270 | "C820005J03Rik" | lincRNA |
| ENSMUSG00000109821 | "Gm6593" | processed_pseudogene |
| ENSMUSG00000111188 | "Gm19709" | processed_pseudogene |
| ENSMUSG00000112444 | "4930401C15Rik" | lincRNA |
| ENSMUSG00000113502 | "AC158115.1" | TEC |
| ENSMUSG00000115437 | "AC122459.3" | TEC |
| ENSMUSG00000081951 | "Gm15352" | processed_pseudogene |
| ENSMUSG00000076548 | "Igkv4-69" | IG_V_gene |
| ENSMUSG00000091412 | "Gm2895" | processed_transcript |

Fig. 9 contd.

| | | |
|---|---|---|
| ENSMUSG00000033200 | "Tpsg1" | protein_coding |
| ENSMUSG00000096638 | "Ighv2-9" | IG_V_gene |
| ENSMUSG00000045010 | "Gm4779" | protein_coding |
| ENSMUSG00000044457 | "Stk-ps2" | transcribed_processed_pseudogene |
| ENSMUSG00000094951 | "Ighv5-6" | IG_V_gene |
| ENSMUSG00000109160 | "4930598N05Rik" | processed_transcript |
| ENSMUSG00000094533 | "Ighv11-1" | IG_V_gene |
| ENSMUSG00000103811 | "Gm38004" | lincRNA |
| ENSMUSG00000113725 | "AC113441.2" | TEC |
| ENSMUSG00000079045 | "Prox1os" | antisense_RNA |
| ENSMUSG00000057223 | "Gm6578" | transcribed_processed_pseudogene |
| ENSMUSG00000101328 | "Rpl30-ps6" | processed_pseudogene |
| ENSMUSG00000105516 | "Gm36823" | lincRNA |
| ENSMUSG00000076906 | "Traj23" | TR_J_gene |
| ENSMUSG00000112622 | "AC122850.1" | TEC |
| ENSMUSG00000091157 | "Serpina3l-ps" | unprocessed_pseudogene |
| ENSMUSG00000098977 | "Gm27196" | antisense_RNA |
| ENSMUSG00000069609 | "Cd300ld4" | protein_coding |
| ENSMUSG00000088249 | "Gm25908" | rRNA |
| ENSMUSG00000087485 | "Gm13383" | lincRNA |
| ENSMUSG00000060187 | "Lrrc10" | protein_coding |
| ENSMUSG00000102260 | "D330025C20Rik" | TEC |
| ENSMUSG00000069911 | "Fam196b" | protein_coding |
| ENSMUSG00000030433 | "Sbk2" | protein_coding |
| ENSMUSG00000089281 | "Scarna6" | scaRNA |
| ENSMUSG00000041287 | "Sox15" | protein_coding |
| ENSMUSG00000104103 | "Gm9517" | processed_pseudogene |
| ENSMUSG00000102926 | "Gm37151" | TEC |
| ENSMUSG00000056035 | "Cyp3a11" | protein_coding |
| ENSMUSG00000051067 | "Lingo3" | protein_coding |
| ENSMUSG00000086799 | "4930502E09Rik" | processed_transcript |
| ENSMUSG00000049134 | "Nrap" | protein_coding |
| ENSMUSG00000104648 | "Gm42570" | processed_pseudogene |
| ENSMUSG00000105656 | "Gm43017" | sense_intronic |
| ENSMUSG00000077756 | "Snord90" | snoRNA |
| ENSMUSG00000094262 | "Igkv4-62" | IG_V_gene |
| ENSMUSG00000109725 | "Gm45265" | TEC |
| ENSMUSG00000108138 | "Gm18485" | processed_pseudogene |
| ENSMUSG00000111193 | "Gm35288" | lincRNA |

Fig. 9 contd.

| | | |
|---|---|---|
| ENSMUSG00000113869 | "AC131743.3" | processed_pseudogene |
| ENSMUSG00000084108 | "Gm15794" | processed_pseudogene |
| ENSMUSG00000107131 | "Gm43763" | lincRNA |
| ENSMUSG00000046590 | "Olfr1165-ps" | polymorphic_pseudogene |
| ENSMUSG00000102565 | "Gm37036" | TEC |
| ENSMUSG00000102657 | "Gm37899" | TEC |
| ENSMUSG00000110826 | "AC113291.1" | lincRNA |
| ENSMUSG00000084572 | "Gm23657" | misc_RNA |
| ENSMUSG00000113244 | "Gm31218" | lincRNA |
| ENSMUSG00000020636 | "Allc" | protein_coding |
| ENSMUSG00000096920 | "Rps19-ps8" | processed_pseudogene |
| ENSMUSG00000092048 | "Vmn2r85" | protein_coding |
| ENSMUSG00000113987 | "4930453C13Rik" | antisense_RNA |
| ENSMUSG00000086777 | "Far2os2" | antisense_RNA |
| ENSMUSG00000094133 | "Olfr1431" | protein_coding |
| ENSMUSG00000076327 | "Gm26338" | miRNA |
| ENSMUSG00000100981 | "Gm29072" | processed_pseudogene |
| ENSMUSG00000110314 | "Gm45625" | lincRNA |
| ENSMUSG00000085500 | "Gm16976" | transcribed_unprocessed_pseudogene |
| ENSMUSG00000042250 | "Pglyrp4" | protein_coding |
| ENSMUSG00000109835 | "Olfr730" | protein_coding |
| ENSMUSG00000021228 | "Acot3" | protein_coding |
| ENSMUSG00000080793 | "Cbx3-ps3" | processed_pseudogene |
| ENSMUSG00000092247 | "Gm20426" | transcribed_processed_pseudogene |
| ENSMUSG00000106193 | "Mir7090" | miRNA |
| ENSMUSG00000112554 | "AC122905.1" | lincRNA |
| ENSMUSG00000049761 | "Pmis2" | protein_coding |
| ENSMUSG00000105479 | "Gm43132" | lincRNA |
| ENSMUSG00000085580 | "1700061F12Rik" | lincRNA |
| ENSMUSG00000102148 | "Gm38059" | TEC |
| ENSMUSG00000114067 | "AC161117.2" | transcribed_unprocessed_pseudogene |
| ENSMUSG00000113706 | "AC151982.1" | processed_pseudogene |
| ENSMUSG00000099758 | "Gm10830" | antisense_RNA |
| ENSMUSG00000089957 | "A830011K09Rik" | antisense_RNA |
| ENSMUSG00000019913 | "Sim1" | protein_coding |
| ENSMUSG00000083107 | "Gm5303" | processed_pseudogene |
| ENSMUSG00000090211 | "Gm16050" | lincRNA |
| ENSMUSG00000101869 | "Gm29500" | lincRNA |
| ENSMUSG00000081504 | "Gm12508" | processed_pseudogene |

Fig. 9 contd.

| | | |
|---|---|---|
| ENSMUSG00000114152 | "Gm5374" | transcribed_processed_pseudogene |
| ENSMUSG00000056777 | "Rpl21-ps13" | processed_pseudogene |
| ENSMUSG00000103179 | "Gm37171" | TEC |
| ENSMUSG00000099979 | "Gm5896" | processed_pseudogene |
| ENSMUSG00000110701 | "Gm6013" | processed_pseudogene |
| ENSMUSG00000044254 | "Pcsk9" | protein_coding |
| ENSMUSG00000088790 | "Gm22541" | snoRNA |
| ENSMUSG00000109284 | "B230311B06Rik" | lincRNA |
| ENSMUSG00000105181 | "Gm19620" | processed_pseudogene |
| ENSMUSG00000102988 | "Trbv22" | TR_V_pseudogene |
| ENSMUSG00000055385 | "Rnf212" | protein_coding |
| ENSMUSG00000105321 | "Gm44382" | miRNA |
| ENSMUSG00000076065 | "Mir681" | miRNA |
| ENSMUSG00000049217 | "Olfr788" | protein_coding |
| ENSMUSG00000111283 | "E230034D01Rik" | processed_transcript |
| ENSMUSG00000079700 | "Fpr3" | protein_coding |
| ENSMUSG00000104625 | "Gm42448" | TEC |
| ENSMUSG00000086151 | "Gm5698" | processed_pseudogene |
| ENSMUSG00000077564 | "Gm23202" | snoRNA |
| ENSMUSG00000101505 | "1700109G14Rik" | antisense_RNA |
| ENSMUSG00000102508 | "Gm37367" | TEC |
| ENSMUSG00000105894 | "Gm42710" | TEC |
| ENSMUSG00000087082 | "Gm15423" | antisense_RNA |
| ENSMUSG00000100274 | "1700006F04Rik" | sense_intronic |
| ENSMUSG00000020481 | "Ankrd36" | protein_coding |
| ENSMUSG00000115664 | "CT010577.1" | lincRNA |
| ENSMUSG00000086162 | "Gm16342" | unitary_pseudogene |
| ENSMUSG00000065100 | "Gm26132" | snoRNA |
| ENSMUSG00000064586 | "Gm25132" | snRNA |
| ENSMUSG00000091165 | "Gm17036" | antisense_RNA |
| ENSMUSG00000101287 | "Gm28166" | lincRNA |
| ENSMUSG00000028356 | "Ambp" | protein_coding |
| ENSMUSG00000110964 | "Gm20953" | processed_pseudogene |
| ENSMUSG00000094926 | "Gm16533" | processed_pseudogene |
| ENSMUSG00000096377 | "Mir5123" | miRNA |
| ENSMUSG00000112314 | "AC155712.2" | lincRNA |
| ENSMUSG00000084995 | "Lyzl4os" | antisense_RNA |
| ENSMUSG00000111208 | "AC156504.2" | lincRNA |
| ENSMUSG00000113904 | "Gm32351" | lincRNA |

Fig. 9 contd.

| | | |
|---|---|---|
| ENSMUSG00000026940 | "Ccdc183" | protein_coding |
| ENSMUSG00000046676 | "Lce1l" | protein_coding |
| ENSMUSG00000101559 | "Gm28258" | lincRNA |
| ENSMUSG00000105682 | "Gm44323" | miRNA |
| ENSMUSG00000081745 | "Gm15549" | processed_pseudogene |
| ENSMUSG00000111204 | "AC166052.1" | antisense_RNA |
| ENSMUSG00000015787 | "Abo" | protein_coding |
| ENSMUSG00000091768 | "Gm17617" | protein_coding |
| ENSMUSG00000052767 | "Gm12703" | processed_transcript |
| ENSMUSG00000088573 | "Gm24530" | misc_RNA |
| ENSMUSG00000105816 | "D030025E07Rik" | processed_transcript |
| ENSMUSG00000115748 | "AC102291.3" | processed_pseudogene |
| ENSMUSG00000085245 | "Gm11713" | antisense_RNA |
| ENSMUSG00000087470 | "A630031M04Rik" | lincRNA |
| ENSMUSG00000115071 | "AC154843.1" | TEC |
| ENSMUSG00000065560 | "Mir148b" | miRNA |
| ENSMUSG00000106126 | "Gm43781" | TEC |
| ENSMUSG00000085088 | "4931413K12Rik" | processed_transcript |
| ENSMUSG00000086167 | "Gm13827" | processed_pseudogene |
| ENSMUSG00000029679 | "Hyal6" | protein_coding |
| ENSMUSG00000112477 | "AC153506.3" | lincRNA |
| ENSMUSG00000113698 | "AC124586.1" | TEC |
| ENSMUSG00000030507 | "Dbx1" | protein_coding |
| ENSMUSG00000114654 | "AC154222.2" | lincRNA |
| ENSMUSG00000097155 | "Gm26511" | lincRNA |
| ENSMUSG00000020168 | "Olfr299" | protein_coding |
| ENSMUSG00000102942 | "Ighv1-33" | IG_V_pseudogene |
| ENSMUSG00000030378 | "Sult2a8" | protein_coding |
| ENSMUSG00000098653 | "Gm27672" | miRNA |
| ENSMUSG00000064717 | "Gm24208" | snoRNA |
| ENSMUSG00000115625 | "AC140426.1" | lincRNA |
| ENSMUSG00000082196 | "Gm14231" | processed_pseudogene |
| ENSMUSG00000106469 | "C030015E24Rik" | TEC |
| ENSMUSG00000028298 | "Cga" | protein_coding |
| ENSMUSG00000050201 | "Otop2" | protein_coding |
| ENSMUSG00000026336 | "Slco6d1" | protein_coding |
| ENSMUSG00000114572 | "AC154328.1" | processed_pseudogene |
| ENSMUSG00000092568 | "Olfr759-ps1" | unprocessed_pseudogene |
| ENSMUSG00000086491 | "Gm13291" | lincRNA |

Fig. 9 contd.

| | | |
|---|---|---|
| ENSMUSG00000105153 | "Gm3143" | lincRNA |
| ENSMUSG00000115310 | "CT009515.3" | lincRNA |
| ENSMUSG00000026368 | "F13b" | protein_coding |
| ENSMUSG00000071179 | "Serpina16" | protein_coding |
| ENSMUSG00000087346 | "Gm5699" | processed_pseudogene |
| ENSMUSG00000094017 | "Gm13160" | processed_pseudogene |
| ENSMUSG00000095218 | "Olfr1338" | protein_coding |
| ENSMUSG00000030307 | "Slc6a11" | protein_coding |
| ENSMUSG00000014747 | "Ankrd53" | protein_coding |
| ENSMUSG00000003974 | "Grm3" | protein_coding |
| ENSMUSG00000109734 | "Gm45272" | lincRNA |
| ENSMUSG00000110754 | "4930405J17Rik" | antisense_RNA |
| ENSMUSG00000102357 | "Gm38348" | sense_intronic |
| ENSMUSG00000056995 | "Olfr1178" | protein_coding |
| ENSMUSG00000084240 | "Gm15383" | processed_pseudogene |
| ENSMUSG00000076923 | "Traj5" | TR_J_gene |
| ENSMUSG00000087666 | "B230359F08Rik" | TR_V_gene |
| ENSMUSG00000100146 | "1700020M21Rik" | lincRNA |
| ENSMUSG00000089080 | "Gm24003" | snRNA |
| ENSMUSG00000085931 | "Gm12648" | lincRNA |
| ENSMUSG00000061863 | "Gm6822" | processed_pseudogene |
| ENSMUSG00000067229 | "Cyp2c66" | protein_coding |
| ENSMUSG00000099273 | "Gm27452" | miRNA |
| ENSMUSG00000107153 | "Gm38404" | lincRNA |
| ENSMUSG00000079391 | "Gm2974" | protein_coding |
| ENSMUSG00000086337 | "Gm11535" | lincRNA |
| ENSMUSG00000082141 | "Gm11212" | unprocessed_pseudogene |
| ENSMUSG00000035780 | "Ugt2a3" | protein_coding |
| ENSMUSG00000109312 | "Gm44682" | TEC |
| ENSMUSG00000115035 | "AC149294.4" | processed_pseudogene |
| ENSMUSG00000086338 | "Gm13723" | protein_coding |
| ENSMUSG00000113081 | "Gm3333" | transcribed_processed_pseudogene |
| ENSMUSG00000109628 | "BC024386" | processed_transcript |
| ENSMUSG00000091376 | "Aadacl2" | protein_coding |
| ENSMUSG00000108986 | "Gm32061" | lincRNA |
| ENSMUSG00000083831 | "Gm14248" | processed_pseudogene |
| ENSMUSG00000021867 | "Tmem254b" | protein_coding |
| ENSMUSG00000098506 | "Phf20-ps" | processed_pseudogene |
| ENSMUSG00000052595 | "A1cf" | protein_coding |

Fig. 9 contd.

| | | |
|---|---|---|
| ENSMUSG00000106762 | "4930478P22Rik" | lincRNA |
| ENSMUSG00000024173 | "Tpsab1" | protein_coding |
| ENSMUSG00000022877 | "Hrg" | protein_coding |
| ENSMUSG00000113129 | "Gm21569" | processed_pseudogene |
| ENSMUSG00000107595 | "Gm44441" | TEC |
| ENSMUSG00000096895 | "Gm25245" | snRNA |
| ENSMUSG00000042801 | "Olfr769" | protein_coding |
| ENSMUSG00000108703 | "Gm44793" | antisense_RNA |
| ENSMUSG00000089967 | "Gm16550" | processed_pseudogene |
| ENSMUSG00000084909 | "4930528G23Rik" | lincRNA |
| ENSMUSG00000114188 | "Gm40849" | lincRNA |
| ENSMUSG00000081221 | "Gm14760" | processed_pseudogene |
| ENSMUSG00000110825 | "Gm8959" | processed_pseudogene |
| ENSMUSG00000080844 | "Gm14107" | processed_pseudogene |
| ENSMUSG00000082682 | "Gm15349" | processed_pseudogene |
| ENSMUSG00000100784 | "Gm28421" | lincRNA |
| ENSMUSG00000092075 | "Serpina4-ps1" | unprocessed_pseudogene |
| ENSMUSG00000081494 | "Gm14130" | processed_pseudogene |
| ENSMUSG00000084221 | "Hmgb1-ps4" | processed_pseudogene |
| ENSMUSG00000038676 | "Ucn" | protein_coding |
| ENSMUSG00000115021 | "Vmn1r173" | protein_coding |
| ENSMUSG00000089871 | "Speer4cos" | antisense_RNA |
| ENSMUSG00000103441 | "7530428D23Rik" | transcribed_processed_pseudogene |
| ENSMUSG00000106705 | "Gm2602" | processed_pseudogene |
| ENSMUSG00000099401 | "Gm28375" | antisense_RNA |
| ENSMUSG00000091814 | "Gm8050" | protein_coding |
| ENSMUSG00000025013 | "Tll2" | protein_coding |
| ENSMUSG00000092342 | "Esp31" | protein_coding |
| ENSMUSG00000026572 | "Tbx19" | protein_coding |
| ENSMUSG00000072931 | "Gm15080" | protein_coding |
| ENSMUSG00000103241 | "Gm38089" | TEC |
| ENSMUSG00000032517 | "Mobp" | protein_coding |
| ENSMUSG00000103713 | "Gm2136" | TEC |
| ENSMUSG00000097082 | "4933440J02Rik" | lincRNA |
| ENSMUSG00000063830 | "Gm6065" | processed_pseudogene |
| ENSMUSG00000085838 | "Chn1os1" | antisense_RNA |
| ENSMUSG00000088244 | "Gm25909" | snoRNA |
| ENSMUSG00000095870 | "Lce1k" | protein_coding |
| ENSMUSG00000098121 | "Gm27038" | processed_pseudogene |

Fig. 9 contd.

| | | |
|---|---|---|
| ENSMUSG00000097886 | "Gsg1l2" | protein_coding |
| ENSMUSG00000087080 | "Gm12199" | antisense_RNA |
| ENSMUSG00000091731 | "Gm17542" | protein_coding |
| ENSMUSG00000081289 | "Gm14857" | processed_pseudogene |
| ENSMUSG00000093289 | "Snord92" | snoRNA |
| ENSMUSG00000093666 | "Vmn1r-ps15" | unprocessed_pseudogene |
| ENSMUSG00000095063 | "Slx" | protein_coding |
| ENSMUSG00000065521 | "Mir296" | miRNA |
| ENSMUSG00000082933 | "Gm14811" | processed_pseudogene |
| ENSMUSG00000110674 | "Gm45892" | antisense_RNA |
| ENSMUSG00000102892 | "Gm37854" | antisense_RNA |
| ENSMUSG00000088873 | "Gm25864" | snRNA |
| ENSMUSG00000098481 | "Gm27387" | miRNA |
| ENSMUSG00000046000 | "Naa11" | protein_coding |
| ENSMUSG00000046321 | "Hs3st2" | protein_coding |
| ENSMUSG00000097605 | "9430098F02Rik" | lincRNA |
| ENSMUSG00000085237 | "Gm15406" | lincRNA |
| ENSMUSG00000081940 | "Xlr3e-ps" | unprocessed_pseudogene |
| ENSMUSG00000081946 | "Gm11472" | processed_pseudogene |
| ENSMUSG00000040759 | "Cmtm5" | protein_coding |
| ENSMUSG00000041468 | "Gpr12" | protein_coding |
| ENSMUSG00000113960 | "4933412O06Rik" | lincRNA |
| ENSMUSG00000040452 | "Cdh12" | protein_coding |
| ENSMUSG00000082836 | "Gm13612" | processed_pseudogene |
| ENSMUSG00000105387 | "Gm29681" | lincRNA |
| ENSMUSG00000102952 | "Ighv1-25" | IG_V_pseudogene |
| ENSMUSG00000065486 | "Mir450-1" | miRNA |
| ENSMUSG00000096486 | "Gm5426" | protein_coding |
| ENSMUSG00000071452 | "Gm11397" | protein_coding |
| ENSMUSG00000093738 | "AI606473" | processed_transcript |
| ENSMUSG00000090128 | "Gm16038" | unprocessed_pseudogene |
| ENSMUSG00000015854 | "Cd5l" | protein_coding |
| ENSMUSG00000078235 | "Fam43b" | protein_coding |
| ENSMUSG00000064581 | "Gm25133" | snoRNA |
| ENSMUSG00000112277 | "AC159379.1" | lincRNA |
| ENSMUSG00000110573 | "Gm5485" | protein_coding |
| ENSMUSG00000075245 | "Gm6043" | processed_pseudogene |
| ENSMUSG00000112650 | "Gm5184" | processed_pseudogene |
| ENSMUSG00000090306 | "Adh6-ps1" | transcribed_unprocessed_pseudogene |

Fig. 9 contd.

| | | |
|---|---|---|
| ENSMUSG00000056880 | "Gadl1" | protein_coding |
| ENSMUSG00000104117 | "Gm20743" | processed_transcript |
| ENSMUSG00000026450 | "Chit1" | protein_coding |
| ENSMUSG00000038670 | "Mybpc2" | protein_coding |
| ENSMUSG00000059898 | "Dsc3" | protein_coding |
| ENSMUSG00000099469 | "Gm29141" | unprocessed_pseudogene |
| ENSMUSG00000052554 | "Defb34" | protein_coding |
| ENSMUSG00000113737 | "BB123696" | lincRNA |
| ENSMUSG00000075387 | "Olfr341" | protein_coding |
| ENSMUSG00000086666 | "Gm12249" | lincRNA |
| ENSMUSG00000066366 | "Serpina1a" | protein_coding |
| ENSMUSG00000064658 | "Gm24166" | snoRNA |
| ENSMUSG00000033268 | "Duox1" | protein_coding |
| ENSMUSG00000019787 | "Trdn" | protein_coding |
| ENSMUSG00000114595 | "AC115760.1" | antisense_RNA |
| ENSMUSG00000084386 | "Gm13852" | processed_pseudogene |
| ENSMUSG00000095892 | "Rnu5g" | snRNA |
| ENSMUSG00000100166 | "B230110G15Rik" | antisense_RNA |
| ENSMUSG00000034482 | "Ly6g5c" | protein_coding |
| ENSMUSG00000106130 | "Gm44361" | miRNA |
| ENSMUSG00000113569 | "AC134917.1" | processed_pseudogene |
| ENSMUSG00000081194 | "Gm8424" | processed_pseudogene |
| ENSMUSG00000005474 | "Myl10" | protein_coding |
| ENSMUSG00000102999 | "Gm37762" | TEC |
| ENSMUSG00000097052 | "Snhg7" | snoRNA |
| ENSMUSG00000081972 | "Gm16397" | processed_pseudogene |
| ENSMUSG00000097940 | "Gm21392" | processed_pseudogene |
| ENSMUSG00000090131 | "Gm16162" | processed_pseudogene |
| ENSMUSG00000111941 | "Gm33263" | lincRNA |
| ENSMUSG00000058207 | "Serpina3k" | protein_coding |
| ENSMUSG00000084143 | "Gm13400" | processed_pseudogene |
| ENSMUSG00000114563 | "AC139750.2" | antisense_RNA |
| ENSMUSG00000058252 | "Tcp11x2" | protein_coding |
| ENSMUSG00000001622 | "Csn3" | protein_coding |
| ENSMUSG00000106080 | "Gm8836" | processed_pseudogene |
| ENSMUSG00000081226 | "Gm8802" | processed_pseudogene |
| ENSMUSG00000109653 | "Gm45608" | processed_pseudogene |
| ENSMUSG00000070577 | "Gm572" | protein_coding |
| ENSMUSG00000060404 | "Olfr1369-ps1" | protein_coding |

Fig. 9 contd.

| | | |
|---|---|---|
| ENSMUSG00000076891 | "Traj39" | TR_J_gene |
| ENSMUSG00000031210 | "Gpr165" | protein_coding |
| ENSMUSG00000112876 | "Gm32443" | lincRNA |
| ENSMUSG00000103497 | "Gm37407" | TEC |
| ENSMUSG00000056966 | "Gjc3" | protein_coding |
| ENSMUSG00000025754 | "Agbl1" | protein_coding |
| ENSMUSG00000086760 | "1700025D23Rik" | lincRNA |
| ENSMUSG00000100780 | "Gm28579" | lincRNA |
| ENSMUSG00000106046 | "Gm44462" | miRNA |
| ENSMUSG00000024227 | "Pdzph1" | protein_coding |
| ENSMUSG00000088071 | "Gm22818" | snRNA |
| ENSMUSG00000108183 | "Gm44227" | processed_pseudogene |
| ENSMUSG00000096577 | "Ighv1-71" | IG_V_gene |
| ENSMUSG00000106325 | "Ighv8-10" | IG_V_pseudogene |
| ENSMUSG00000106485 | "3830422I06Rik" | TEC |
| ENSMUSG00000043165 | "Lor" | protein_coding |
| ENSMUSG00000044220 | "Nkx2-3" | protein_coding |
| ENSMUSG00000115458 | "AC140244.1" | processed_pseudogene |
| ENSMUSG00000107823 | "Gm44436" | TEC |
| ENSMUSG00000033122 | "Hsd17b3" | protein_coding |
| ENSMUSG00000066586 | "Scgb2b26" | protein_coding |
| ENSMUSG00000091129 | "Iqcf6" | protein_coding |
| ENSMUSG00000059203 | "Il1rapl2" | protein_coding |
| ENSMUSG00000109761 | "5430403N17Rik" | lincRNA |
| ENSMUSG00000092338 | "Gm26940" | lincRNA |
| ENSMUSG00000076376 | "Mir674" | miRNA |
| ENSMUSG00000047643 | "Gm5454" | processed_pseudogene |
| ENSMUSG00000090489 | "Gm17415" | processed_pseudogene |
| ENSMUSG00000113132 | "Gm9231" | processed_pseudogene |
| ENSMUSG00000086957 | "Gm13869" | lincRNA |
| ENSMUSG00000052276 | "Ostn" | protein_coding |
| ENSMUSG00000087896 | "Gm25282" | snRNA |
| ENSMUSG00000083940 | "Gm11298" | processed_pseudogene |
| ENSMUSG00000101641 | "Gm29560" | TEC |
| ENSMUSG00000103092 | "Pcdha5" | protein_coding |
| ENSMUSG00000062561 | "Gm10118" | protein_coding |
| ENSMUSG00000111979 | "AC122887.1" | TEC |
| ENSMUSG00000096205 | "Gm22068" | snRNA |
| ENSMUSG00000108866 | "Gm35082" | lincRNA |

Fig. 9 contd.

| | | |
|---|---|---|
| ENSMUSG00000055730 | "Ces2a" | protein_coding |
| ENSMUSG00000093634 | "Gm10860" | antisense_RNA |
| ENSMUSG00000111351 | "AC153845.1" | processed_pseudogene |
| ENSMUSG00000085588 | "3110004A20Rik" | lincRNA |
| ENSMUSG00000110138 | "4831440D22Rik" | antisense_RNA |
| ENSMUSG00000111457 | "Gm18996" | processed_pseudogene |
| ENSMUSG00000114989 | "CT030238.1" | lincRNA |
| ENSMUSG00000067438 | "Hmx1" | protein_coding |
| ENSMUSG00000005202 | "Shbg" | protein_coding |
| ENSMUSG00000048304 | "Slitrk3" | protein_coding |
| ENSMUSG00000082729 | "Gm14845" | processed_pseudogene |
| ENSMUSG00000111631 | "Gm32017" | processed_transcript |
| ENSMUSG00000092841 | "Gm24330" | miRNA |
| ENSMUSG00000014198 | "Zfp385c" | protein_coding |
| ENSMUSG00000109353 | "Gm45183" | TEC |
| ENSMUSG00000090066 | "1110002E22Rik" | protein_coding |
| ENSMUSG00000102723 | "Gm37936" | TEC |
| ENSMUSG00000115425 | "CT030238.3" | lincRNA |
| ENSMUSG00000098097 | "6530403H02Rik" | lincRNA |
| ENSMUSG00000070990 | "Foxe1" | protein_coding |
| ENSMUSG00000081433 | "Serpinb1-ps1" | unprocessed_pseudogene |
| ENSMUSG00000042118 | "Bhmt2" | protein_coding |
| ENSMUSG00000073830 | "Mup14" | protein_coding |
| ENSMUSG00000111371 | "AC164123.1" | lincRNA |
| ENSMUSG00000113548 | "Gm34047" | lincRNA |
| ENSMUSG00000029882 | "2210010C04Rik" | protein_coding |
| ENSMUSG00000095430 | "Vmn1r72" | protein_coding |
| ENSMUSG00000106995 | "Gm33167" | TEC |
| ENSMUSG00000101595 | "Gm29395" | lincRNA |
| ENSMUSG00000113749 | "Mrto4-ps1" | processed_pseudogene |
| ENSMUSG00000043329 | "Gm8849" | processed_pseudogene |
| ENSMUSG00000103555 | "Gm37337" | TEC |
| ENSMUSG00000082308 | "Gm15770" | processed_pseudogene |
| ENSMUSG00000051062 | "Fbll1" | protein_coding |
| ENSMUSG00000106353 | "Gm43726" | processed_pseudogene |
| ENSMUSG00000020875 | "Hoxb9" | protein_coding |
| ENSMUSG00000055088 | "Olfr354" | protein_coding |
| ENSMUSG00000094745 | "Olfr954" | protein_coding |
| ENSMUSG00000086598 | "Btbd18" | protein_coding |

Fig. 9 contd.

| | | |
|---|---|---|
| ENSMUSG00000050211 | "Pla2g4e" | protein_coding |
| ENSMUSG00000067771 | "Gm14685" | protein_coding |
| ENSMUSG00000104123 | "Gm37483" | TEC |
| ENSMUSG00000102698 | "Gm37777" | TEC |
| ENSMUSG00000098501 | "Gm19272" | lincRNA |
| ENSMUSG00000103732 | "Gm38315" | TEC |
| ENSMUSG00000085300 | "Gm16345" | processed_pseudogene |
| ENSMUSG00000096936 | "Gm3510" | lincRNA |
| ENSMUSG00000065460 | "Mir133a-2" | miRNA |
| ENSMUSG00000090634 | "Gm8126" | protein_coding |
| ENSMUSG00000105484 | "Gm42775" | lincRNA |
| ENSMUSG00000083855 | "Olfr1175-ps" | protein_coding |
| ENSMUSG00000108003 | "Gm35386" | lincRNA |
| ENSMUSG00000040134 | "Rdh7" | protein_coding |
| ENSMUSG00000104982 | "Gm32554" | lincRNA |
| ENSMUSG00000101061 | "Platr1" | lincRNA |
| ENSMUSG00000023802 | "Nox3" | protein_coding |
| ENSMUSG00000107780 | "9530013L04Rik" | TEC |
| ENSMUSG00000103654 | "Gm37203" | processed_pseudogene |
| ENSMUSG00000061387 | "Olfr1490" | protein_coding |
| ENSMUSG00000110006 | "Gm45490" | lincRNA |
| ENSMUSG00000085427 | "6430710C18Rik" | lincRNA |
| ENSMUSG00000093784 | "Gm22394" | snoRNA |
| ENSMUSG00000105423 | "Gm36814" | processed_transcript |
| ENSMUSG00000080767 | "Gm15595" | processed_pseudogene |
| ENSMUSG00000092939 | "Gm22907" | miRNA |
| ENSMUSG00000113683 | "CT030159.2" | antisense_RNA |
| ENSMUSG00000106536 | "Gm42508" | TEC |
| ENSMUSG00000097393 | "D030068K23Rik" | lincRNA |
| ENSMUSG00000108749 | "Gm44767" | antisense_RNA |
| ENSMUSG00000110592 | "4930488N15Rik" | lincRNA |
| ENSMUSG00000013936 | "Myl2" | protein_coding |
| ENSMUSG00000010064 | "Slc38a3" | protein_coding |
| ENSMUSG00000112175 | "4930452L12Rik" | lincRNA |
| ENSMUSG00000109248 | "Gm44993" | lincRNA |
| ENSMUSG00000031204 | "Asb12" | protein_coding |
| ENSMUSG00000081934 | "Gm12193" | processed_pseudogene |
| ENSMUSG00000103011 | "Gm8860" | processed_pseudogene |
| ENSMUSG00000076668 | "Ighv7-4" | IG_V_gene |

Fig. 9 contd.

| | | |
|---|---|---|
| ENSMUSG00000099243 | "Gm27538" | misc_RNA |
| ENSMUSG00000027470 | "Mylk2" | protein_coding |
| ENSMUSG00000095165 | "Gm25547" | snRNA |
| ENSMUSG00000041698 | "Slco1a1" | protein_coding |
| ENSMUSG00000087133 | "Gm27192" | lincRNA |
| ENSMUSG00000073967 | "Olfr557" | protein_coding |
| ENSMUSG00000111160 | "AC160118.1" | lincRNA |
| ENSMUSG00000105481 | "6430500D05Rik" | TEC |
| ENSMUSG00000114471 | "AC117237.1" | processed_pseudogene |
| ENSMUSG00000022485 | "Hoxc5" | protein_coding |
| ENSMUSG00000097474 | "Gm26584" | lincRNA |
| ENSMUSG00000098944 | "Mir8120" | miRNA |
| ENSMUSG00000100637 | "Gm20819" | unprocessed_pseudogene |
| ENSMUSG00000097857 | "Gm26603" | lincRNA |
| ENSMUSG00000030592 | "Ryr1" | protein_coding |
| ENSMUSG00000111429 | "Gm32511" | antisense_RNA |
| ENSMUSG00000076547 | "Igkv4-70" | IG_V_gene |
| ENSMUSG00000111922 | "AC153370.1" | lincRNA |
| ENSMUSG00000099381 | "Gm18303" | processed_pseudogene |
| ENSMUSG00000068889 | "Lce1e" | protein_coding |
| ENSMUSG00000031492 | "Chrnb3" | protein_coding |
| ENSMUSG00000092574 | "2810047C21Rik1" | transcribed_unprocessed_pseudogene |
| ENSMUSG00000063751 | "Platr8" | processed_transcript |
| ENSMUSG00000091060 | "7420461P10Rik" | protein_coding |
| ENSMUSG00000109755 | "Gm8489" | processed_pseudogene |
| ENSMUSG00000027401 | "Tgm3" | protein_coding |
| ENSMUSG00000106869 | "Gm42473" | TEC |
| ENSMUSG00000099869 | "1700030F04Rik" | lincRNA |
| ENSMUSG00000114293 | "AC154788.1" | processed_pseudogene |
| ENSMUSG00000031772 | "Cntnap4" | protein_coding |
| ENSMUSG00000065544 | "Mir32" | miRNA |
| ENSMUSG00000114041 | "Gm9269" | unprocessed_pseudogene |
| ENSMUSG00000089151 | "Mir1950" | miRNA |
| ENSMUSG00000026058 | "Khdrbs2" | protein_coding |
| ENSMUSG00000103999 | "Gm38026" | TEC |
| ENSMUSG00000109923 | "Gm20039" | processed_pseudogene |
| ENSMUSG00000103129 | "Gm37393" | TEC |
| ENSMUSG00000088958 | "Scarna8" | scaRNA |
| ENSMUSG00000092210 | "A930009A15Rik" | protein_coding |

Fig. 9 contd.

| | | |
|---|---|---|
| ENSMUSG00000075222 | "Olfr988" | protein_coding |
| ENSMUSG00000102556 | "Gm37569" | TEC |
| ENSMUSG00000080616 | "Gm22152" | snoRNA |
| ENSMUSG00000057454 | "Lypd3" | protein_coding |
| ENSMUSG00000101724 | "Gm29453" | sense_intronic |
| ENSMUSG00000084413 | "Gm12017" | processed_pseudogene |
| ENSMUSG00000097229 | "Platr23" | lincRNA |
| ENSMUSG00000006014 | "Prg4" | protein_coding |
| ENSMUSG00000025991 | "Cps1" | protein_coding |
| ENSMUSG00000085548 | "Gm11753" | sense_intronic |
| ENSMUSG00000031998 | "1700128F08Rik" | transcribed_processed_pseudogene |
| ENSMUSG00000107486 | "Trbv4" | TR_V_gene |
| ENSMUSG00000086156 | "Gm15354" | antisense_RNA |
| ENSMUSG00000032807 | "Alox12b" | protein_coding |
| ENSMUSG00000115651 | "AC122769.4" | processed_pseudogene |
| ENSMUSG00000112874 | "Gm34297" | lincRNA |
| ENSMUSG00000114439 | "AC159106.2" | lincRNA |
| ENSMUSG00000039508 | "Fam26d" | protein_coding |
| ENSMUSG00000003053 | "Cyp2c29" | protein_coding |
| ENSMUSG00000106905 | "Gm42741" | TEC |
| ENSMUSG00000024863 | "Mbl2" | protein_coding |
| ENSMUSG00000098225 | "Gm9556" | processed_pseudogene |
| ENSMUSG00000046354 | "Defb14" | protein_coding |
| ENSMUSG00000086911 | "Gm12027" | lincRNA |
| ENSMUSG00000098929 | "Mir6400" | miRNA |
| ENSMUSG00000105219 | "Gm43821" | lincRNA |
| ENSMUSG00000031957 | "Ctrb1" | protein_coding |
| ENSMUSG00000061701 | "Fbxw20" | protein_coding |
| ENSMUSG00000092843 | "Gm24332" | miRNA |
| ENSMUSG00000097843 | "Gm26755" | lincRNA |
| ENSMUSG00000074647 | "Fam83c" | protein_coding |
| ENSMUSG00000100431 | "4930558N11Rik" | lincRNA |
| ENSMUSG00000033544 | "Angptl1" | protein_coding |
| ENSMUSG00000108398 | "Gm30191" | protein_coding |
| ENSMUSG00000107601 | "Gm2651" | processed_pseudogene |
| ENSMUSG00000040113 | "Mettl11b" | protein_coding |
| ENSMUSG00000109299 | "Gm45164" | lincRNA |
| ENSMUSG00000112888 | "AC166256.1" | processed_transcript |
| ENSMUSG00000057534 | "Elobl" | protein_coding |

Fig. 9 contd.

| | | |
|---|---|---|
| ENSMUSG00000028749 | "Pla2g2f" | protein_coding |
| ENSMUSG00000031519 | "Asb5" | protein_coding |
| ENSMUSG00000078815 | "Cacng6" | protein_coding |
| ENSMUSG00000111871 | "AC113304.1" | lincRNA |
| ENSMUSG00000073656 | "Gm10558" | antisense_RNA |
| ENSMUSG00000064052 | "Gm5089" | protein_coding |
| ENSMUSG00000026835 | "Fcnb" | protein_coding |
| ENSMUSG00000088090 | "Gm23668" | rRNA |
| ENSMUSG00000096446 | "Gm8104" | protein_coding |
| ENSMUSG00000088892 | "Gm22518" | miRNA |
| ENSMUSG00000095635 | "Gm22951" | snRNA |
| ENSMUSG00000022454 | "Nell2" | protein_coding |
| ENSMUSG00000107251 | "Gm43102" | TEC |
| ENSMUSG00000042816 | "Gpr151" | protein_coding |
| ENSMUSG00000102231 | "1700074A21Rik" | TEC |
| ENSMUSG00000085791 | "Rpl30-ps9" | processed_pseudogene |
| ENSMUSG00000085845 | "Gm13944" | antisense_RNA |
| ENSMUSG00000020214 | "Glipr1l2" | protein_coding |
| ENSMUSG00000067522 | "Olfr76" | protein_coding |
| ENSMUSG00000040694 | "Apobec2" | protein_coding |
| ENSMUSG00000096579 | "Gm17121" | processed_pseudogene |
| ENSMUSG00000113707 | "Gm10457" | lincRNA |
| ENSMUSG00000037140 | "Tas2r108" | protein_coding |
| ENSMUSG00000092795 | "Gm22690" | miRNA |
| ENSMUSG00000044938 | "Klhl31" | protein_coding |
| ENSMUSG00000090464 | "Gm17140" | antisense_RNA |
| ENSMUSG00000105550 | "Gm35585" | lincRNA |
| ENSMUSG00000112125 | "AC087891.2" | lincRNA |
| ENSMUSG00000013653 | "1810065E05Rik" | protein_coding |
| ENSMUSG00000073956 | "Olfr592" | protein_coding |
| ENSMUSG00000108295 | "Gm36406" | processed_transcript |
| ENSMUSG00000081873 | "Gm15197" | processed_pseudogene |
| ENSMUSG00000009580 | "Odam" | protein_coding |
| ENSMUSG00000108338 | "Gm44794" | TEC |
| ENSMUSG00000057446 | "Cts8" | protein_coding |
| ENSMUSG00000111703 | "AC121870.1" | TEC |
| ENSMUSG00000090044 | "Gm16557" | processed_pseudogene |
| ENSMUSG00000111606 | "Gm7213" | processed_pseudogene |
| ENSMUSG00000082936 | "Gm16166" | processed_pseudogene |

Fig. 9 contd.

| | | |
|---|---|---|
| ENSMUSG00000025129 | "Ppp1r27" | protein_coding |
| ENSMUSG00000110574 | "Gm21112" | processed_pseudogene |
| ENSMUSG00000100252 | "Mir124-2hg" | lincRNA |
| ENSMUSG00000019936 | "Epyc" | protein_coding |
| ENSMUSG00000074433 | "Lce3e" | protein_coding |
| ENSMUSG00000094248 | "Hist1h2ao" | protein_coding |
| ENSMUSG00000027547 | "Sall4" | protein_coding |
| ENSMUSG00000041359 | "Tcl1" | protein_coding |
| ENSMUSG00000105534 | "Gm42435" | antisense_RNA |
| ENSMUSG00000076892 | "Traj38" | TR_J_gene |
| ENSMUSG00000084834 | "4930565N06Rik" | antisense_RNA |
| ENSMUSG00000020805 | "Slc13a5" | protein_coding |
| ENSMUSG00000089703 | "Gm15833" | processed_pseudogene |
| ENSMUSG00000032083 | "Apoa1" | protein_coding |
| ENSMUSG00000102771 | "Gm33320" | TEC |
| ENSMUSG00000114693 | "AC124489.2" | lincRNA |
| ENSMUSG00000079048 | "4933413L06Rik" | antisense_RNA |
| ENSMUSG00000091419 | "Gm17450" | pseudogene |
| ENSMUSG00000109563 | "Gm44772" | TEC |
| ENSMUSG00000085559 | "Gm11959" | lincRNA |
| ENSMUSG00000032081 | "Apoc3" | protein_coding |
| ENSMUSG00000088922 | "Gm24296" | snRNA |
| ENSMUSG00000060918 | "Olfr51" | protein_coding |
| ENSMUSG00000052372 | "Il1rapl1" | protein_coding |
| ENSMUSG00000102885 | "Gm37280" | lincRNA |
| ENSMUSG00000027912 | "Lce1m" | protein_coding |
| ENSMUSG00000028236 | "Sdr16c5" | protein_coding |
| ENSMUSG00000075307 | "Klhl41" | protein_coding |
| ENSMUSG00000060556 | "Olfr1418" | protein_coding |
| ENSMUSG00000061614 | "Olfr845" | protein_coding |
| ENSMUSG00000072849 | "Serpina1e" | protein_coding |
| ENSMUSG00000107433 | "Gm43882" | TEC |
| ENSMUSG00000114414 | "AC154849.2" | lincRNA |
| ENSMUSG00000108865 | | processed_transcript |
| ENSMUSG00000108726 | "Gm30684" | lincRNA |
| ENSMUSG00000077643 | "Gm24985" | snoRNA |
| ENSMUSG00000114732 | "CT009713.8" | lincRNA |
| ENSMUSG00000049160 | "Tex50" | protein_coding |
| ENSMUSG00000073602 | "Serpinb3b" | protein_coding |

Fig. 9 contd.

| | | |
|---|---|---|
| ENSMUSG00000101299 | "Gm28175" | lincRNA |
| ENSMUSG00000057215 | "Platr28" | lincRNA |
| ENSMUSG00000113309 | "AC173210.1" | TEC |
| ENSMUSG00000113472 | "CT009757.3" | TEC |
| ENSMUSG00000095676 | "Gm25099" | snRNA |
| ENSMUSG00000108553 | "Gm38569" | lincRNA |
| ENSMUSG00000109113 | "Gm32916" | lincRNA |
| ENSMUSG00000098579 | "Mir6937" | miRNA |
| ENSMUSG00000115143 | "AC142114.1" | processed_pseudogene |
| ENSMUSG00000081295 | "Gm6275" | processed_pseudogene |
| ENSMUSG00000106246 | "Gm18867" | processed_pseudogene |
| ENSMUSG00000094025 | "Gm8879" | protein_coding |
| ENSMUSG00000000183 | "Fgf6" | protein_coding |
| ENSMUSG00000058147 | "Xlr3c" | protein_coding |
| ENSMUSG00000058328 | "Xlr5a" | protein_coding |
| ENSMUSG00000029656 | "C8b" | protein_coding |
| ENSMUSG00000096157 | "Gm5472" | processed_pseudogene |
| ENSMUSG00000060084 | "Olfr748" | protein_coding |
| ENSMUSG00000067006 | "Serpinb5" | protein_coding |
| ENSMUSG00000094605 | "Gm25873" | snRNA |
| ENSMUSG00000044086 | "Lmod3" | protein_coding |
| ENSMUSG00000100335 | "2310008N11Rik" | lincRNA |
| ENSMUSG00000048455 | "Sprr1b" | protein_coding |
| ENSMUSG00000026950 | "Neb" | protein_coding |
| ENSMUSG00000092223 | "Gm19807" | processed_pseudogene |
| ENSMUSG00000031936 | "Hephl1" | protein_coding |
| ENSMUSG00000056632 | "Dsg3" | protein_coding |
| ENSMUSG00000064580 | "Gm25134" | snRNA |
| ENSMUSG00000056912 | "1700017N19Rik" | protein_coding |
| ENSMUSG00000113586 | "CT025611.1" | lincRNA |
| ENSMUSG00000114670 | "AC154305.3" | processed_pseudogene |
| ENSMUSG00000079584 | "Gm364" | protein_coding |
| ENSMUSG00000096003 | "Gm3500" | protein_coding |
| ENSMUSG00000022342 | "Kcnv1" | protein_coding |
| ENSMUSG00000089404 | "Gm24877" | misc_RNA |
| ENSMUSG00000107917 | "Gm44235" | TEC |
| ENSMUSG00000062826 | "Ces2f" | protein_coding |
| ENSMUSG00000061527 | "Krt5" | protein_coding |
| ENSMUSG00000071561 | "BC100530" | protein_coding |

Fig. 9 contd.

| | | |
|---|---|---|
| ENSMUSG00000007122 | "Casq1" | protein_coding |
| ENSMUSG00000106851 | "4930421C12Rik" | TEC |
| ENSMUSG00000097497 | "Gm26652" | lincRNA |
| ENSMUSG00000114171 | "Gm18313" | processed_pseudogene |
| ENSMUSG00000105923 | "A830019L24Rik" | lincRNA |
| ENSMUSG00000111453 | "Olfr925-ps1" | unprocessed_pseudogene |
| ENSMUSG00000114569 | "AC154849.3" | lincRNA |
| ENSMUSG00000027022 | "Xirp2" | protein_coding |
| ENSMUSG00000110986 | "Gm20276" | TEC |
| ENSMUSG00000029368 | "Alb" | protein_coding |
| ENSMUSG00000027923 | "Lce1b" | protein_coding |
| ENSMUSG00000113164 | "4930559C10Rik" | lincRNA |
| ENSMUSG00000060583 | "Olfr881" | protein_coding |
| ENSMUSG00000094174 | "Ighv6-4" | IG_V_gene |
| ENSMUSG00000071177 | "Serpina1d" | protein_coding |
| ENSMUSG00000026983 | "Il1f5" | protein_coding |
| ENSMUSG00000083713 | "Gm5883" | processed_pseudogene |
| ENSMUSG00000036938 | "Try5" | protein_coding |
| ENSMUSG00000027868 | "Tbx15" | protein_coding |
| ENSMUSG00000067231 | "Cyp2c65" | protein_coding |
| ENSMUSG00000076541 | "Igkv4-79" | IG_V_gene |
| ENSMUSG00000054630 | "Ugt2b5" | protein_coding |
| ENSMUSG00000086219 | "Srrm4os" | antisense_RNA |
| ENSMUSG00000109907 | "Gm45321" | lincRNA |
| ENSMUSG00000020125 | "Elane" | protein_coding |
| ENSMUSG00000065743 | "Gm25008" | snRNA |
| ENSMUSG00000034768 | "Asb16" | protein_coding |
| ENSMUSG00000103243 | "Lce1d" | protein_coding |
| ENSMUSG00000078498 | "Zfp988" | protein_coding |
| ENSMUSG00000086676 | "Gm14705" | antisense_RNA |
| ENSMUSG00000046932 | "Vmn1r193" | protein_coding |
| ENSMUSG00000024512 | "Dynap" | protein_coding |
| ENSMUSG00000001657 | "Hoxc8" | protein_coding |
| ENSMUSG00000082464 | "Rab9b-ps1" | processed_pseudogene |
| ENSMUSG00000027919 | "Lce1g" | protein_coding |
| ENSMUSG00000082701 | "Gm14460" | processed_pseudogene |
| ENSMUSG00000066364 | "Serpina3b" | protein_coding |
| ENSMUSG00000091721 | "Gimd1" | protein_coding |
| ENSMUSG00000026253 | "Chrng" | protein_coding |

Fig. 9 contd.

| | | |
|---|---|---|
| ENSMUSG00000042258 | "Isl1" | protein_coding |
| ENSMUSG00000073834 | "Mup11" | protein_coding |
| ENSMUSG00000065331 | "Gm24927" | snRNA |
| ENSMUSG00000093010 | "Gm22460" | miRNA |
| ENSMUSG00000092392 | "Gm20546" | lincRNA |
| ENSMUSG00000097624 | "Gm5091" | lincRNA |
| ENSMUSG00000079025 | "Gsdmc" | protein_coding |
| ENSMUSG00000020950 | "Foxg1" | protein_coding |
| ENSMUSG00000044322 | "Dsc1" | protein_coding |
| ENSMUSG00000042353 | "Frem3" | protein_coding |
| ENSMUSG00000033831 | "Fgb" | protein_coding |
| ENSMUSG00000089718 | "2310075C17Rik" | lincRNA |
| ENSMUSG00000061762 | "Tac1" | protein_coding |
| ENSMUSG00000059832 | "Kprp" | protein_coding |
| ENSMUSG00000089936 | "Gm16199" | processed_pseudogene |
| ENSMUSG00000061816 | "Myl1" | protein_coding |
| ENSMUSG00000028386 | "Slc46a2" | protein_coding |
| ENSMUSG00000099143 | "Gm27483" | misc_RNA |
| ENSMUSG00000087095 | "Emx2os" | antisense_RNA |
| ENSMUSG00000030399 | "Ckm" | protein_coding |
| ENSMUSG00000109576 | "Gm44704" | TEC |
| ENSMUSG00000063297 | "Luzp2" | protein_coding |
| ENSMUSG00000098816 | "Gm27786" | misc_RNA |
| ENSMUSG00000022227 | "Mcpt1" | protein_coding |
| ENSMUSG00000026100 | "Mstn" | protein_coding |
| ENSMUSG00000031097 | "Tnni2" | protein_coding |
| ENSMUSG00000043969 | "Emx2" | protein_coding |
| ENSMUSG00000057609 | "Lce1a1" | protein_coding |
| ENSMUSG00000048981 | "Krt31" | protein_coding |
| ENSMUSG00000027209 | "Fam227b" | protein_coding |
| ENSMUSG00000059741 | "Myl3" | protein_coding |
| ENSMUSG00000062181 | "Ces3b" | protein_coding |
| ENSMUSG00000075402 | "Krt76" | protein_coding |
| ENSMUSG00000079015 | "Serpina1c" | protein_coding |
| ENSMUSG00000105757 | "Ighv1-83" | IG_V_pseudogene |
| ENSMUSG00000027887 | "Sypl2" | protein_coding |
| ENSMUSG00000113178 | "Mylf-ps" | processed_pseudogene |
| ENSMUSG00000085903 | "Gm15340" | lincRNA |
| ENSMUSG00000034648 | "Lrrn1" | protein_coding |

Fig. 9 contd.

| | | |
|---|---|---|
| ENSMUSG00000012520 | "Phox2b" | protein_coding |
| ENSMUSG00000056078 | "Lipm" | protein_coding |
| ENSMUSG00000027077 | "Smtnl1" | protein_coding |
| ENSMUSG00000034362 | "Csta1" | protein_coding |
| ENSMUSG00000029361 | "Nos1" | protein_coding |
| ENSMUSG00000000766 | "Oprm1" | protein_coding |
| ENSMUSG00000045776 | "Lrtm1" | protein_coding |
| ENSMUSG00000087404 | "Gm11752" | lincRNA |
| ENSMUSG00000032079 | "Apoa5" | protein_coding |
| ENSMUSG00000053675 | "Tgm5" | protein_coding |
| ENSMUSG00000073842 | "Mup7" | protein_coding |
| ENSMUSG00000057280 | "Musk" | protein_coding |
| ENSMUSG00000018862 | "Otop3" | protein_coding |
| ENSMUSG00000039269 | "2300002M23Rik" | protein_coding |
| ENSMUSG00000029205 | "Chrna9" | protein_coding |
| ENSMUSG00000085348 | "Myhas" | antisense_RNA |
| ENSMUSG00000045019 | "Acer1" | protein_coding |
| ENSMUSG00000079278 | "Tmem233" | protein_coding |
| ENSMUSG00000068890 | "Lce1a2" | protein_coding |
| ENSMUSG00000107585 | "3300002P13Rik" | lincRNA |
| ENSMUSG00000085479 | "9430073C21Rik" | antisense_RNA |
| ENSMUSG00000094993 | "Igkv4-51" | IG_V_gene |
| ENSMUSG00000061723 | "Tnnt3" | protein_coding |
| ENSMUSG00000044594 | "Serpinb3a" | protein_coding |
| ENSMUSG00000005716 | "Pvalb" | protein_coding |
| ENSMUSG00000096537 | "Fam240b" | protein_coding |
| ENSMUSG00000068885 | "Lce3f" | protein_coding |
| ENSMUSG00000061808 | "Ttr" | protein_coding |
| ENSMUSG00000054325 | "Lce3a" | protein_coding |
| ENSMUSG00000094862 | "Ighv1-56" | IG_V_gene |
| ENSMUSG00000022875 | "Kng1" | protein_coding |
| ENSMUSG00000026413 | "Pkp1" | protein_coding |
| ENSMUSG00000093087 | "Mir3473d" | miRNA |
| ENSMUSG00000049173 | "Myoz3" | protein_coding |
| ENSMUSG00000041991 | "Hrnr" | protein_coding |
| ENSMUSG00000046699 | "Slitrk4" | protein_coding |
| ENSMUSG00000049641 | "Vgll2" | protein_coding |
| ENSMUSG00000042031 | "Lce3b" | protein_coding |
| ENSMUSG00000026251 | "Chrnd" | protein_coding |

Fig. 9 contd.

| | | |
|---|---|---|
| ENSMUSG00000073375 | "Lrrc30" | protein_coding |
| ENSMUSG00000032368 | "Zic1" | protein_coding |
| ENSMUSG00000100410 | "2310020H05Rik" | lincRNA |
| ENSMUSG00000009471 | "Myod1" | protein_coding |
| ENSMUSG00000059230 | "Defb4" | protein_coding |
| ENSMUSG00000074001 | "Klhl40" | protein_coding |
| ENSMUSG00000079428 | "Tceal7" | protein_coding |
| ENSMUSG00000037086 | "Prr32" | protein_coding |
| ENSMUSG00000026459 | "Myog" | protein_coding |
| ENSMUSG00000063821 | "Dupd1" | protein_coding |
| ENSMUSG00000054905 | "Stfa3" | protein_coding |
| ENSMUSG00000069372 | "Ctxn3" | protein_coding |
| ENSMUSG00000025216 | "Lbx1" | protein_coding |
| ENSMUSG00000045475 | "Lce3c" | protein_coding |
| ENSMUSG00000033765 | "Calm4" | protein_coding |
| ENSMUSG00000005355 | "Casp14" | protein_coding |
| ENSMUSG00000030672 | "Mylpf" | protein_coding |
| ENSMUSG00000027107 | "Chrna1" | protein_coding |
| ENSMUSG00000000214 | "Th" | protein_coding |
| ENSMUSG00000016327 | "Atp1b4" | protein_coding |
| ENSMUSG00000058354 | "Krt6a" | protein_coding |
| ENSMUSG00000078672 | "Mup20" | protein_coding |
| ENSMUSG00000030730 | "Atp2a1" | protein_coding |
| ENSMUSG00000045539 | "Sprr3" | protein_coding |
| ENSMUSG00000039070 | "Cpa4" | protein_coding |
| ENSMUSG00000053522 | "Lgals7" | protein_coding |
| ENSMUSG00000025229 | "Pitx3" | protein_coding |
| ENSMUSG00000074768 | "Bhmt" | protein_coding |
| ENSMUSG00000027913 | "Crct1" | protein_coding |
| ENSMUSG00000068697 | "Myoz1" | protein_coding |
| ENSMUSG00000017204 | "Gsdma" | protein_coding |
| ENSMUSG00000046095 | "Krt32" | protein_coding |
| ENSMUSG00000045545 | "Krt14" | protein_coding |
| ENSMUSG00000085888 | "Gm12224" | antisense_RNA |
| ENSMUSG00000020722 | "Cacng1" | protein_coding |
| ENSMUSG00000066154 | "Mup3" | protein_coding |
| ENSMUSG00000099906 | "Gm28653" | lincRNA |
| ENSMUSG00000031757 | "Mt4" | protein_coding |
| ENSMUSG00000006457 | "Actn3" | protein_coding |

Fig. 9 contd.

| | | |
|---|---|---|
| ENSMUSG00000035923 | "Myf6" | protein_coding |
| ENSMUSG00000020216 | "Jsrp1" | protein_coding |
| ENSMUSG00000000031 | "H19" | lincRNA |
| ENSMUSG00000044041 | "Krt13" | protein_coding |
| ENSMUSG00000027419 | "Pcsk2" | protein_coding |
| ENSMUSG00000071858 | "Gm94" | protein_coding |
| ENSMUSG00000033196 | "Myh2" | protein_coding |
| ENSMUSG00000059668 | "Krt4" | protein_coding |
| ENSMUSG00000087410 | "2310065F04Rik" | lincRNA |
| ENSMUSG00000062713 | "Sim2" | protein_coding |
| ENSMUSG00000024471 | "Myot" | protein_coding |
| ENSMUSG00000063651 | "Cnfn" | protein_coding |
| ENSMUSG00000074199 | "Krtdap" | protein_coding |
| ENSMUSG00000017300 | "Tnnc2" | protein_coding |
| ENSMUSG00000087090 | "Nctc1" | processed_transcript |
| ENSMUSG00000031972 | "Acta1" | protein_coding |
| ENSMUSG00000020061 | "Mybpc1" | protein_coding |
| ENSMUSG00000056328 | "Myh1" | protein_coding |
| ENSMUSG00000055775 | "Myh8" | protein_coding |
| ENSMUSG00000057003 | "Myh4" | protein_coding |

Fig. 9 contd.

SEQUENCE LISTING

```
<160> NUMBER OF SEQ ID NOS: 8

<210> SEQ ID NO 1
<211> LENGTH: 29
<212> TYPE: PRT
<213> ORGANISM: Homo sapiens
<220> FEATURE:
<221> NAME/KEY: MISC_FEATURE
<223> OTHER INFORMATION: hGHRH (1-29)HN2

<400> SEQUENCE: 1

Tyr Ala Asp Ala Ile Phe Thr Asn Ser Tyr Arg Lys Val Leu Gly Gln
1               5                   10                  15

Leu Ser Ala Arg Lys Leu Leu Gln Asp Ile Met Ser Arg
            20                  25

<210> SEQ ID NO 2
```

```
<211> LENGTH: 32
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Xaa is PhAc (phenylacetyl), Nac
      (naphthylacetyl), Oct (octanoyl), N-Me-Aib (N-methyl-alpha-
      aminoisobutyroyl), Dca (dichloroacetyl), Ac-Ada (acetyl-12-
      aminododecanoyl), Fer (ferulyl), Ac-Amc (acetyl-8-aminocaprylyl),
      Me-NH-Sub (methyl-NH-suberyl),
<220> FEATURE:
<221> NAME/KEY: MISC_FEATURE
<222> LOCATION: (3)..(3)
<223> OTHER INFORMATION: Xaa is D-Arg
<220> FEATURE:
<221> NAME/KEY: MISC_FEATURE
<222> LOCATION: (5)..(5)
<223> OTHER INFORMATION: Xaa is Ala or Me-Ala
<220> FEATURE:
<221> NAME/KEY: MISC_FEATURE
<222> LOCATION: (7)..(7)
<223> OTHER INFORMATION: Xaa is Cpa (para-chlorophenylalanine) or Phe(F)
<220> FEATURE:
<221> NAME/KEY: MISC_FEATURE
<222> LOCATION: (9)..(9)
<223> OTHER INFORMATION: Xaa is Ala, Pal (pyridylalanine), Dip ((3,3-
      diphenyl)alanine), or Me-Ala
<220> FEATURE:
<221> NAME/KEY: MISC_FEATURE
<222> LOCATION: (10)..(10)
<223> OTHER INFORMATION: Xaa is Har
<220> FEATURE:
<221> NAME/KEY: MISC_FEATURE
<222> LOCATION: (11)..(11)
<223> OTHER INFORMATION: Xaa is FPa5, Tyr(Alk) where Alk is Me or Et
<220> FEATURE:
<221> NAME/KEY: MISC_FEATURE
<222> LOCATION: (12)..(12)
<223> OTHER INFORMATION: Xaa is His or Arg
<220> FEATURE:
<221> NAME/KEY: MISC_FEATURE
<222> LOCATION: (13)..(13)
<223> OTHER INFORMATION: Xaa is Lys, Lys(0-11) (Lys(A0-A1-A2-A3-A4-A5-
      A6-A7-A8-A9 A10-A11-), Lys(Me)2, or Orn (ornithine)
<220> FEATURE:
<221> NAME/KEY: MISC_FEATURE
<222> LOCATION: (16)..(16)
<223> OTHER INFORMATION: Xaa is Abu (alpha-aminobutyric acid) or Orn
<220> FEATURE:
<221> NAME/KEY: MISC_FEATURE
<222> LOCATION: (18)..(18)
<223> OTHER INFORMATION: Xaa is Leu or Glu
<220> FEATURE:
<221> NAME/KEY: MISC_FEATURE
<222> LOCATION: (21)..(21)
<223> OTHER INFORMATION: Xaa is Har (homoarginine) or His
<220> FEATURE:
<221> NAME/KEY: MISC_FEATURE
<222> LOCATION: (22)..(22)
<223> OTHER INFORMATION: Xaa is Lys, Lys(Me)2 or Orn
<220> FEATURE:
<221> NAME/KEY: MISC_FEATURE
<222> LOCATION: (28)..(28)
<223> OTHER INFORMATION: Xaa is Nle
<220> FEATURE:
<221> NAME/KEY: MISC_FEATURE
<222> LOCATION: (29)..(29)
<223> OTHER INFORMATION: Xaa is D-Arg
<220> FEATURE:
<221> NAME/KEY: MISC_FEATURE
<222> LOCATION: (30)..(30)
<223> OTHER INFORMATION: Xaa is Har, Arg or Agm (agmatine)
<220> FEATURE:
<221> NAME/KEY: MISC_FEATURE
<222> LOCATION: (31)..(31)
<223> OTHER INFORMATION: Xaa is  Ala, Amc, Apa, Ada, AE2A , AE4P,E -
```

```
            Lys( alpha-NH2), Agm, or absent
<220> FEATURE:
<221> NAME/KEY: MISC_FEATURE
<222> LOCATION: (32)..(32)
<223> OTHER INFORMATION: Xaa is  Lys(Oct), Ahx (6-aminohexanoyl), or
      absent
<220> FEATURE:
<221> NAME/KEY: MOD_RES
<222> LOCATION: (32)..(32)
<223> OTHER INFORMATION: AMIDATION

<400> SEQUENCE: 2

Xaa Tyr Xaa Asp Xaa Ile Xaa Thr Xaa Xaa Xaa Xaa Xaa Val Leu Xaa
1               5                   10                  15

Gln Xaa Ser Ala Xaa Xaa Leu Leu Gln Asp Ile Xaa Xaa Xaa Xaa Xaa
            20                  25                  30

<210> SEQ ID NO 3
<211> LENGTH: 32
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Xaa is Phac
<220> FEATURE:
<221> NAME/KEY: MISC_FEATURE
<222> LOCATION: (2)..(2)
<223> OTHER INFORMATION: Xaa is Ada
<220> FEATURE:
<221> NAME/KEY: MISC_FEATURE
<222> LOCATION: (4)..(4)
<223> OTHER INFORMATION: Xaa is D-Arg
<220> FEATURE:
<221> NAME/KEY: MISC_FEATURE
<222> LOCATION: (8)..(8)
<223> OTHER INFORMATION: Xaa is Phe(F)5
<220> FEATURE:
<221> NAME/KEY: MISC_FEATURE
<222> LOCATION: (11)..(11)
<223> OTHER INFORMATION: Xaa is Har
<220> FEATURE:
<221> NAME/KEY: MISC_FEATURE
<222> LOCATION: (12)..(12)
<223> OTHER INFORMATION: Xaa is Tyr(Me)
<220> FEATURE:
<221> NAME/KEY: MISC_FEATURE
<222> LOCATION: (14)..(14)
<223> OTHER INFORMATION: Xaa is Orn
<220> FEATURE:
<221> NAME/KEY: MISC_FEATURE
<222> LOCATION: (17)..(17)
<223> OTHER INFORMATION: Xaa is Abu
<220> FEATURE:
<221> NAME/KEY: MISC_FEATURE
<222> LOCATION: (23)..(23)
<223> OTHER INFORMATION: Xaa is Orn
<220> FEATURE:
<221> NAME/KEY: MISC_FEATURE
<222> LOCATION: (29)..(29)
<223> OTHER INFORMATION: Xaa is Nle
<220> FEATURE:
<221> NAME/KEY: MISC_FEATURE
<222> LOCATION: (30)..(30)
<223> OTHER INFORMATION: Xaa is D-Arg
<220> FEATURE:
<221> NAME/KEY: MISC_FEATURE
<222> LOCATION: (31)..(31)
<223> OTHER INFORMATION: Xaa is Har
<220> FEATURE:
<221> NAME/KEY: MISC_FEATURE
<222> LOCATION: (32)..(32)
<223> OTHER INFORMATION: Xaa is Agm
<220> FEATURE:
```

-continued

```
<221> NAME/KEY: MOD_RES
<222> LOCATION: (32)..(32)
<223> OTHER INFORMATION: AMIDATION

<400> SEQUENCE: 3

Xaa Xaa Tyr Xaa Asp Ala Ile Xaa Thr Ala Xaa Xaa His Xaa Val Leu
1               5                   10                  15

Xaa Gln Leu Ser Ala His Xaa Leu Leu Gln Asp Ile Xaa Xaa Xaa Xaa
            20                  25                  30

<210> SEQ ID NO 4
<211> LENGTH: 32
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Xaa is Phac
<220> FEATURE:
<221> NAME/KEY: MISC_FEATURE
<222> LOCATION: (2)..(2)
<223> OTHER INFORMATION: Xaa is Ada
<220> FEATURE:
<221> NAME/KEY: MISC_FEATURE
<222> LOCATION: (4)..(4)
<223> OTHER INFORMATION: Xaa is D-Arg
<220> FEATURE:
<221> NAME/KEY: MISC_FEATURE
<222> LOCATION: (8)..(8)
<223> OTHER INFORMATION: Xaa is Phe(F)5
<220> FEATURE:
<221> NAME/KEY: MISC_FEATURE
<222> LOCATION: (9)..(9)
<223> OTHER INFORMATION: Xaa is Thr(Me)
<220> FEATURE:
<221> NAME/KEY: MISC_FEATURE
<222> LOCATION: (11)..(11)
<223> OTHER INFORMATION: Xaa is Har
<220> FEATURE:
<221> NAME/KEY: MISC_FEATURE
<222> LOCATION: (12)..(12)
<223> OTHER INFORMATION: Xaa is Tyr(Me)
<220> FEATURE:
<221> NAME/KEY: MISC_FEATURE
<222> LOCATION: (14)..(14)
<223> OTHER INFORMATION: Xaa is Orn
<220> FEATURE:
<221> NAME/KEY: MISC_FEATURE
<222> LOCATION: (17)..(17)
<223> OTHER INFORMATION: Xaa is Abu
<220> FEATURE:
<221> NAME/KEY: MISC_FEATURE
<222> LOCATION: (23)..(23)
<223> OTHER INFORMATION: Xaa is Orn
<220> FEATURE:
<221> NAME/KEY: MISC_FEATURE
<222> LOCATION: (29)..(29)
<223> OTHER INFORMATION: Xaa is Nle
<220> FEATURE:
<221> NAME/KEY: MISC_FEATURE
<222> LOCATION: (30)..(30)
<223> OTHER INFORMATION: Xaa is D-Arg
<220> FEATURE:
<221> NAME/KEY: MISC_FEATURE
<222> LOCATION: (31)..(31)
<223> OTHER INFORMATION: Xaa is Har
<220> FEATURE:
<221> NAME/KEY: MISC_FEATURE
<222> LOCATION: (32)..(32)
<223> OTHER INFORMATION: Xaa is Agm
<220> FEATURE:
<221> NAME/KEY: MOD_RES
<222> LOCATION: (32)..(32)
<223> OTHER INFORMATION: AMIDATION
```

```
<400> SEQUENCE: 4

Xaa Xaa Tyr Xaa Asp Ala Ile Xaa Xaa Ala Xaa Xaa His Xaa Val Leu
1               5                   10                  15

Xaa Gln Leu Ser Ala His Xaa Leu Leu Gln Asp Ile Xaa Xaa Xaa Xaa
                20                  25                  30

<210> SEQ ID NO 5
<211> LENGTH: 31
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Xaa is Phac
<220> FEATURE:
<221> NAME/KEY: MISC_FEATURE
<222> LOCATION: (3)..(3)
<223> OTHER INFORMATION: Xaa is D-Ala
<220> FEATURE:
<221> NAME/KEY: MISC_FEATURE
<222> LOCATION: (7)..(7)
<223> OTHER INFORMATION: Xaa is Cpa
<220> FEATURE:
<221> NAME/KEY: MISC_FEATURE
<222> LOCATION: (10)..(10)
<223> OTHER INFORMATION: Xaa is Har
<220> FEATURE:
<221> NAME/KEY: MISC_FEATURE
<222> LOCATION: (11)..(11)
<223> OTHER INFORMATION: Xaa is Fpa
<220> FEATURE:
<221> NAME/KEY: MISC_FEATURE
<222> LOCATION: (13)..(13)
<223> OTHER INFORMATION: Xaa is Orn
<220> FEATURE:
<221> NAME/KEY: MISC_FEATURE
<222> LOCATION: (16)..(16)
<223> OTHER INFORMATION: Xaa is Abu
<220> FEATURE:
<221> NAME/KEY: MISC_FEATURE
<222> LOCATION: (22)..(22)
<223> OTHER INFORMATION: Xaa is Orn
<220> FEATURE:
<221> NAME/KEY: MISC_FEATURE
<222> LOCATION: (28)..(28)
<223> OTHER INFORMATION: Xaa is Nle
<220> FEATURE:
<221> NAME/KEY: MISC_FEATURE
<222> LOCATION: (29)..(29)
<223> OTHER INFORMATION: Xaa is D-Arg
<220> FEATURE:
<221> NAME/KEY: MISC_FEATURE
<222> LOCATION: (30)..(30)
<223> OTHER INFORMATION: Xaa is Har
<220> FEATURE:
<221> NAME/KEY: MISC_FEATURE
<222> LOCATION: (31)..(31)
<223> OTHER INFORMATION: Xaa is Ada
<220> FEATURE:
<221> NAME/KEY: MOD_RES
<222> LOCATION: (31)..(31)
<223> OTHER INFORMATION: AMIDATION

<400> SEQUENCE: 5

Xaa Tyr Xaa Asp Ala Ile Xaa Thr Ala Xaa Xaa His Xaa Val Leu Xaa
1               5                   10                  15

Gln Leu Ser Ala His Xaa Leu Leu Gly Ala Ile Xaa Xaa Xaa Xaa
                20                  25                  30

<210> SEQ ID NO 6
```

```
<211> LENGTH: 32
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Xaa is Phac
<220> FEATURE:
<221> NAME/KEY: MISC_FEATURE
<222> LOCATION: (2)..(2)
<223> OTHER INFORMATION: Xaa is Ada
<220> FEATURE:
<221> NAME/KEY: MISC_FEATURE
<222> LOCATION: (4)..(4)
<223> OTHER INFORMATION: Xaa is D-Arg
<220> FEATURE:
<221> NAME/KEY: MISC_FEATURE
<222> LOCATION: (8)..(8)
<223> OTHER INFORMATION: Xaa is Cpa
<220> FEATURE:
<221> NAME/KEY: MISC_FEATURE
<222> LOCATION: (11)..(11)
<223> OTHER INFORMATION: Xaa is Har
<220> FEATURE:
<221> NAME/KEY: MISC_FEATURE
<222> LOCATION: (12)..(12)
<223> OTHER INFORMATION: Xaa is Fpa
<220> FEATURE:
<221> NAME/KEY: MISC_FEATURE
<222> LOCATION: (14)..(14)
<223> OTHER INFORMATION: Xaa is Orn
<220> FEATURE:
<221> NAME/KEY: MISC_FEATURE
<222> LOCATION: (17)..(17)
<223> OTHER INFORMATION: Xaa is Abu
<220> FEATURE:
<221> NAME/KEY: MISC_FEATURE
<222> LOCATION: (23)..(23)
<223> OTHER INFORMATION: Xaa is Orn
<220> FEATURE:
<221> NAME/KEY: MISC_FEATURE
<222> LOCATION: (29)..(29)
<223> OTHER INFORMATION: Xaa is Nle
<220> FEATURE:
<221> NAME/KEY: MISC_FEATURE
<222> LOCATION: (30)..(30)
<223> OTHER INFORMATION: Xaa is D-Arg
<220> FEATURE:
<221> NAME/KEY: MISC_FEATURE
<222> LOCATION: (31)..(31)
<223> OTHER INFORMATION: Xaa is Har
<220> FEATURE:
<221> NAME/KEY: MISC_FEATURE
<222> LOCATION: (32)..(32)
<223> OTHER INFORMATION: Xaa is Ada
<220> FEATURE:
<221> NAME/KEY: MISC_FEATURE
<222> LOCATION: (32)..(32)
<223> OTHER INFORMATION: C-Term NH2
<220> FEATURE:
<221> NAME/KEY: MOD_RES
<222> LOCATION: (32)..(32)
<223> OTHER INFORMATION: AMIDATION

<400> SEQUENCE: 6

Xaa Xaa Tyr Xaa Asp Ala Ile Xaa Thr Ala Xaa Xaa His Xaa Val Leu
1               5                   10                  15

Xaa Gln Gln Ser Ala His Xaa Leu Leu Gln Asp Ile Xaa Xaa Xaa Xaa
            20                  25                  30

<210> SEQ ID NO 7
<211> LENGTH: 31
<212> TYPE: PRT
<213> ORGANISM: Artificial Sequence
```

```
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Xaa is Phac
<220> FEATURE:
<221> NAME/KEY: MISC_FEATURE
<222> LOCATION: (2)..(2)
<223> OTHER INFORMATION: Xaa is Ada
<220> FEATURE:
<221> NAME/KEY: MISC_FEATURE
<222> LOCATION: (4)..(4)
<223> OTHER INFORMATION: Xaa is D-Arg
<220> FEATURE:
<221> NAME/KEY: MISC_FEATURE
<222> LOCATION: (8)..(8)
<223> OTHER INFORMATION: Xaa is Cpa
<220> FEATURE:
<221> NAME/KEY: MISC_FEATURE
<222> LOCATION: (11)..(11)
<223> OTHER INFORMATION: Xaa is Har
<220> FEATURE:
<221> NAME/KEY: MISC_FEATURE
<222> LOCATION: (12)..(12)
<223> OTHER INFORMATION: Xaa is Fpa
<220> FEATURE:
<221> NAME/KEY: MISC_FEATURE
<222> LOCATION: (14)..(14)
<223> OTHER INFORMATION: Xaa is Orn
<220> FEATURE:
<221> NAME/KEY: MISC_FEATURE
<222> LOCATION: (17)..(17)
<223> OTHER INFORMATION: Xaa is Abu
<220> FEATURE:
<221> NAME/KEY: MISC_FEATURE
<222> LOCATION: (23)..(23)
<223> OTHER INFORMATION: Xaa is Orn
<220> FEATURE:
<221> NAME/KEY: MISC_FEATURE
<222> LOCATION: (29)..(29)
<223> OTHER INFORMATION: Xaa is Nle
<220> FEATURE:
<221> NAME/KEY: MISC_FEATURE
<222> LOCATION: (30)..(30)
<223> OTHER INFORMATION: Xaa is D-Arg
<220> FEATURE:
<221> NAME/KEY: MISC_FEATURE
<222> LOCATION: (31)..(31)
<223> OTHER INFORMATION: Xaa is Har
<220> FEATURE:
<221> NAME/KEY: MOD_RES
<222> LOCATION: (31)..(31)
<223> OTHER INFORMATION: AMIDATION

<400> SEQUENCE: 7

Xaa Xaa Tyr Xaa Asp Ala Ile Xaa Thr Ala Xaa Xaa His Xaa Val Leu
1               5                   10                  15

Xaa Gln Leu Ser Ala His Xaa Leu Leu Gln Asp Ile Xaa Xaa Xaa
            20                  25                  30

<210> SEQ ID NO 8
<211> LENGTH: 31
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Xaa is PhAc
<220> FEATURE:
<221> NAME/KEY: MISC_FEATURE
<222> LOCATION: (2)..(2)
<223> OTHER INFORMATION: Xaa is Ada
<220> FEATURE:
```

```
<221> NAME/KEY: MISC_FEATURE
<222> LOCATION: (4)..(4)
<223> OTHER INFORMATION: Xaa is D-ARg
<220> FEATURE:
<221> NAME/KEY: MISC_FEATURE
<222> LOCATION: (8)..(8)
<223> OTHER INFORMATION: Xaa is Fpa
<220> FEATURE:
<221> NAME/KEY: MISC_FEATURE
<222> LOCATION: (11)..(11)
<223> OTHER INFORMATION: Xaa is Har
<220> FEATURE:
<221> NAME/KEY: MISC_FEATURE
<222> LOCATION: (12)..(12)
<223> OTHER INFORMATION: Xaa is Tyr(Me)
<220> FEATURE:
<221> NAME/KEY: MISC_FEATURE
<222> LOCATION: (14)..(14)
<223> OTHER INFORMATION: Xaa is Orn
<220> FEATURE:
<221> NAME/KEY: MISC_FEATURE
<222> LOCATION: (17)..(17)
<223> OTHER INFORMATION: Xaa is Abu
<220> FEATURE:
<221> NAME/KEY: MISC_FEATURE
<222> LOCATION: (22)..(22)
<223> OTHER INFORMATION: Xaa is Orn
<220> FEATURE:
<221> NAME/KEY: MISC_FEATURE
<222> LOCATION: (29)..(29)
<223> OTHER INFORMATION: Xaa is Nle
<220> FEATURE:
<221> NAME/KEY: MISC_FEATURE
<222> LOCATION: (30)..(30)
<223> OTHER INFORMATION: Xaa is D-Arg
<220> FEATURE:
<221> NAME/KEY: MISC_FEATURE
<222> LOCATION: (31)..(31)
<223> OTHER INFORMATION: Xaa is Har

<400> SEQUENCE: 8

Xaa Xaa Tyr Xaa Asp Ala Ile Xaa Thr Ala Xaa Xaa His Xaa Val Leu
1               5                  10                  15

Xaa Gln Leu Ser Ala Xaa Lys Leu Leu Gln Asp Ile Xaa Xaa Xaa
            20                  25                  30
```

GHRH ANTAGONISTS FOR USE IN A METHOD OF TREATING SARCOIDOSIS

CROSS REFERENCE TO RELATED APPLICATIONS

The instant application is a continuation application under 35 U.S.C. 111(a) of international patent application number PCT/US2020/042540 filed on Jul. 17, 2020 and designating the United States, which claimed the priority of U.S. provisional patent application 62/875,703, filed on Jul. 18, 2019, which is incorporated by reference in its entirety.

STATEMENT AS TO FEDERALLY SPONSORED RESEARCH

This invention was made with government support under a Distinguished Scientist grant awarded by the Department of Veterans Affairs and under grant number P30CA240139 awarded by the National Institutes of Health (NIH). The government has certain rights in the invention.

INCORPORATION OF THE SEQUENCE LISTING

The present application contains a sequence listing that is submitted via EFS-Web concurrently with the filing of this application, containing the file name "7085-0008_SL.txt" Size: 10,859 bytes, created on Jul. 17, 2020, and is herein incorporated by reference in its entirety.

FIELD OF THE INVENTION

The invention relates to materials and methods for treating sarcoidosis.

BACKGROUND

Sarcoidosis is a multi-organ granulomatous disease of unknown etiology that is associated with significant morbidity and mortality in the US and affects hundreds of thousands of people around the world. Mirsaeidi et al., Chest. 2015; 147(2):438-449. Although the etiology of this condition is not well-known, there are significant similarities between sarcoidosis and other granuloma-forming disorders including mycobacterial and other microbial infections and environmental agent-induced granuloma. Chen et al., Clinics in chest medicine. 2008; 29(3):365-377, vii. In the affected organ, sarcoidosis triggers an early inflammatory reaction characterized by cellular recruitment of TH1 helper cells, followed by a later phase where macrophage recruitment leads to granuloma formation. In certain patients, anti-inflammatory responses, including cytokines and apoptosis, are activated to facilitate tissue healing and repair. Koh et al., Expert Rev Mol Med. 2011; 13:e23. Almost 50% of sarcoidosis patients require systemic steroid therapy. In up to 20% of patients, the inflammatory process continues despite steroids and leads to tissue remodeling with fibrosis (permanent scarring of affected tissue). Patterson et al., Annals of the American Thoracic Society. 2013; 10(4):362-370.

Given the multiorgan involvement of sarcoidosis in more than 50% of patients, the treatment of this disease is challenging. Corticosteroid is the cornerstone of therapy and the US Food and Drug Administration (FDA) has approved only two medications (prednisone and Acthar-Gel) for sarcoidosis 6,7. Miller et al., Ann Intern Med. 1952; 37(4):776-784; Baughman et al., Respir Med. 2016; 110:66-72. However, these agents cause significant side effects after prolonged use, making them undesirable for long-term treatment. In patients with persistent symptoms and complicated presentation with involvement in vital organs, treatment should be started immediately and be continued for months, thus signaling the need of an alternative strategy which is less toxic and tolerable.

SUMMARY

1. The disclosure provides a method of treating sarcoidosis, the method comprising administering a GHRH antagonist to mammalian subject in need thereof. The disclosure further provides use of a GHRH antagonist for treating sarcoidosis or in the preparation of a medicament for treating sarcoidosis. The disclosure also provides a GHRH antagonist for use in treating sarcoidosis.

2. In various aspects, such as the method or use of paragraph 1, the GHRH antagonist comprises the amino acid sequence (Formula I): $R^1$-Tyr$^1$-D-Arg$^2$-Asp$^3$-A$^4$-Ile$^5$-A$^6$-Thr$^7$-A$^8$-Har$^9$-A$^{10}$-A$^{11}$-A$^{12}$-Val$^{13}$-Leu$^{14}$-A$^{15}$-Gln$^{16}$-A$^{17}$-Ser$^{18}$-Ala$^{19}$-A$^{20}$-A$^{21}$-Leu$^{22}$-Leu$^{23}$-Gln$^{24}$-Asp$^{25}$-Ile$^{26}$-Nle$^{27}$-D-Arg$^{28}$-A$^{29}$-R$^2$-R$^3$—NH$_2$ (SEQ ID NO: 2), wherein $R^1$ is PhAc (phenylacetyl), Nac (naphthylacetyl), Oct (octanoyl), N-Me-Aib (N-methyl-alpha-aminoisobutyroyl), Dca (dichloroacetyl), Ac-Ada (acetyl-12-aminododecanoyl), Fer (ferulyl), Ac-Amc (acetyl-8-aminocaprylyl), Me-NH-Sub (methyl-NH-suberyl), PhAc-Ada (phenylacetyl 12-aminododecanoyl), Ac-Ada-D-Phe, Ac-Ada-Phe, Dca-Ada(dichloroacetyl-12-aminododecanoyl), Nac (naphthylacetyl), Nac-Ada, Ada-Ada, or $CH_3(CH_2)_{10}$—CO-Ada;

$A^4$ is Ala or Me-Ala;

$A^6$ is Cpa (para-chlorophenylalanine) or Phe(F)5 (pentafluoro-phenylalanine, also referred to as Fpa5);

$A^8$ is Ala, Pal (pyridylalanine), Dip ((3,3-diphenyl)alanine), or Me-Ala;

$A^{10}$ is Fpa5, Tyr(Alk) where Alk is Me or Et;

$A^{11}$ is His or Arg;

$A^{12}$ is Lys, Lys(0-11) (Lys(A0-A1-A2-A3-A4-A5-A6-A7-A8-A9-A10-A11-), Lys(Me)$_2$, or Orn (ornithine);

$A^{15}$ is Abu (alpha-aminobutyric acid) or Orn;

$A^{17}$ is Leu or Glu;

$A^{20}$ is Har (homoarginine) or His;

$A^{21}$ is Lys, Lys(Me)$_2$ or Orn;

$A^{29}$ is Har, Arg or Agm (agmatine);

$R^2$ is β-Ala, Amc (8-aminocaprylyl), Apa (5-aminopentanoyl), Ada (12-aminododecanoyl), AE2A (8-amino-3,6-dioxaoctanoyl), AE4P (15-amino-4,7,10,13-tetraoxapentadecanoyl), ε-Lys(α-NH2) (a Lys residue, the 8-amino group of which is acylated by the carbonyl group of an N-terminally located amino acid; the α-amino group of the Lys residue is free), Agm (agmatine), or absent; and $R^3$ is Lys(Oct), Ahx (6-aminohexanoyl), or absent.

3. In various aspects, such as the method or use of paragraph 1, the GHRH antagonist is MIA-602, MIA-604, MIA-606, MIA-610, MIA-640, or MIA-690.

4. In various aspects, such as the method or use of paragraph 1, the GHRH antagonist is MIA-602.

5. In various aspects, such as the method or use of any one of paragraphs 1-4, the GHRH antagonist is administered via intradermal, intramuscular, intraperitoneal, intravenous, intraarterial, subcutaneous, epidural, sublingual, intranasal, intracerebral, intraventricular, intrathecal, intravaginal, transdermal, rectally, inhalation, intrapulmonary, intra-airway, intrabronchial, intratracheal, or topical delivery.

6. In various aspects, such as the method or use of paragraph 5, the GHRH antagonist is administered subcutaneously.

7. In various aspects, such as the method or use of any one of paragraphs 1-5, the GHRH antagonist is administered via intranasal, inhalation, intrapulmonary, intra-airway, intra-bronchial, or intratracheal delivery.

8. In various aspects, such as the method or use of any one of paragraphs 1-7, the sarcoidosis is pulmonary sarcoidosis.

BRIEF DESCRIPTION OF THE FIGURES

FIGS. 1A-1E: Bar graphs illustrating the percentage of lung inflammation in mice suffering from sarcoidosis and treated with saline, α-Melanocortin stimulating hormone, (α-MSH, a melanocortin receptor agonist), MIA-602, and Solu-Medrol (methyl prednisolone; current FDA approved medication for sarcoidosis). Pulmonary inflammation was determined and scored by a lung pathologist using Hematoxylin and eosin stain (H&E) staining (FIG. 1A), CD68 levels (FIG. 1B), PD-1 levels (FIG. 1C), PD-L1 levels (FIG. 1D), and CD30 levels (FIG. 1E).

FIGS. 2A-2T are bar graphs illustrating cytokine production (x-axis, pg/mL) in granuloma samples treated with MIA-602 or Solu-Medrol (methyl prednisolone) with comparison to PBMC not challenged with microparticles and granuloma treated with saline.

FIG. 9: A list of genes which exhibited more than 2.5-fold differential expression upon treatment of sarcoidosis mice with MIA-602. The list includes the gene Stable Identifier (Ensembl database reference number), gene name, and RNA transcript type.

DETAILED DESCRIPTION

Figure 2F:
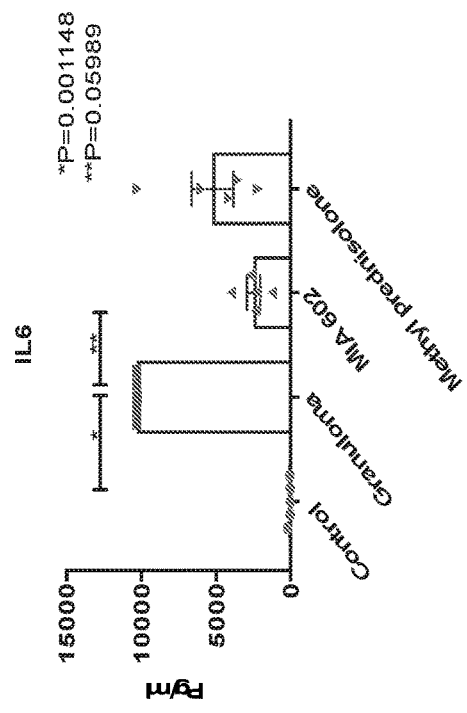
FIGS. 2A-2T: The anti-inflammatory activity of MIA-602 in sarcoid-like granuloma from human cells was tested in peripheral blood mononuclear cells (PBMC) isolated from patients with confirmed sarcoidosis. PBMC were challenged with microparticles resulting in ex vivo granuloma.
Figure 2H:
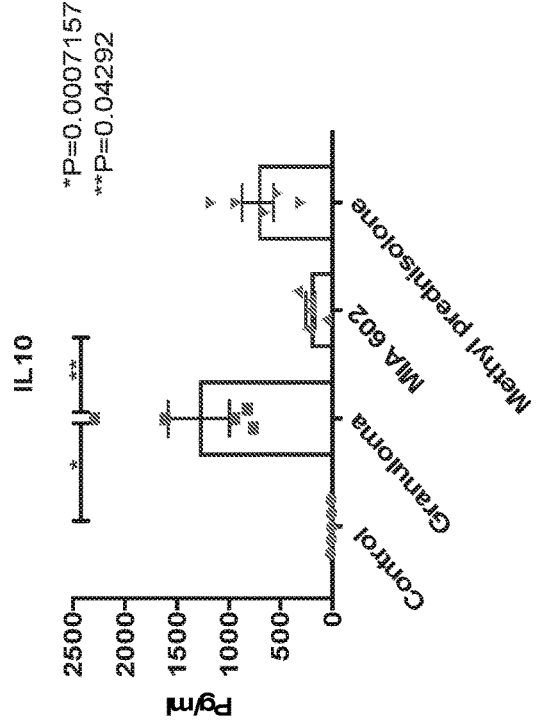
Figure 2E:
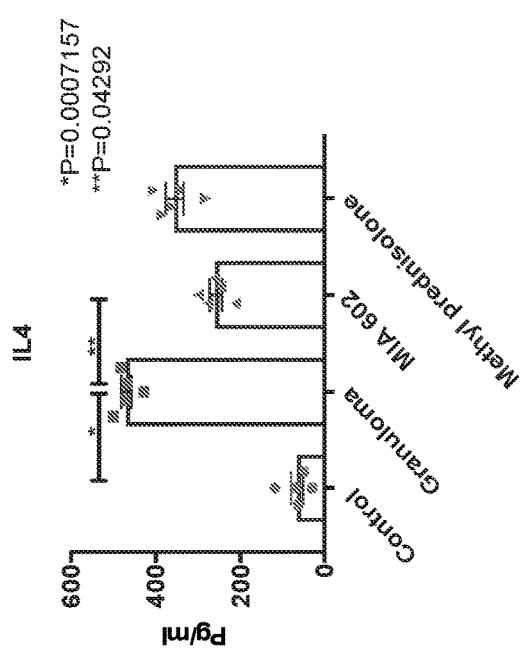
Figure 2G:
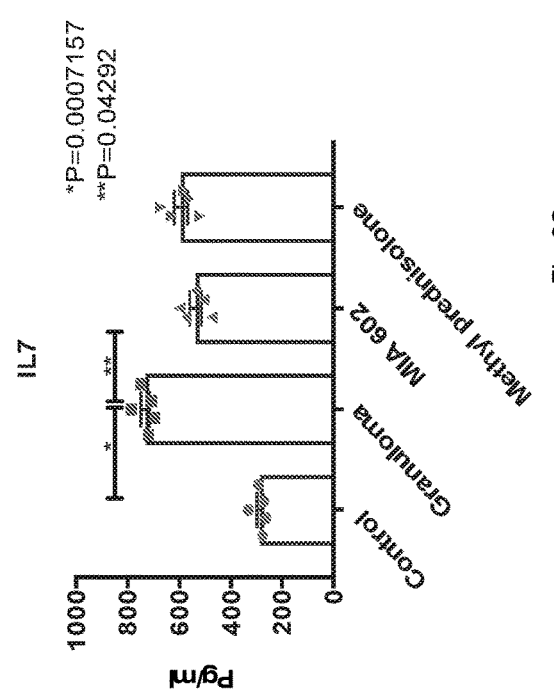
Figure 2J:
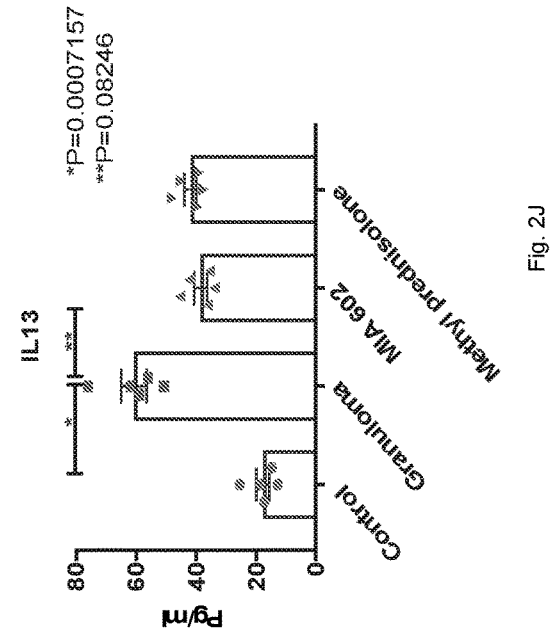
Figure 2L:
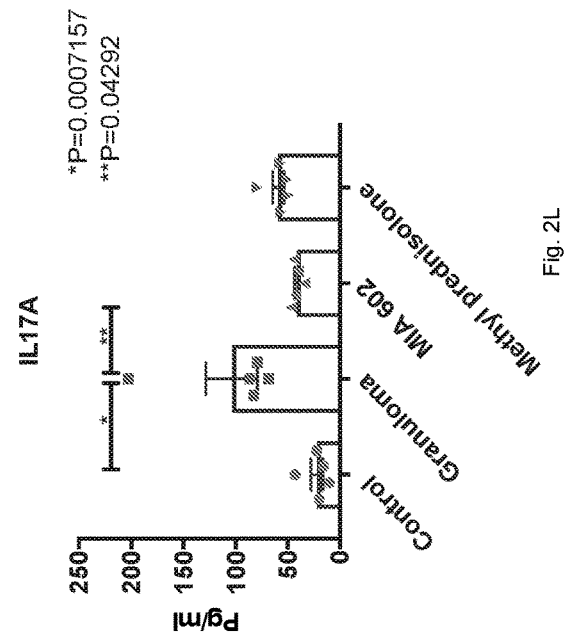
Figure 2I:
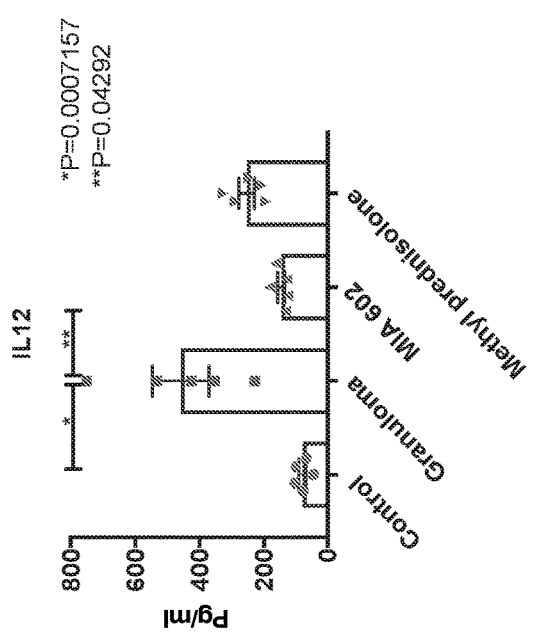
Figure 2K:
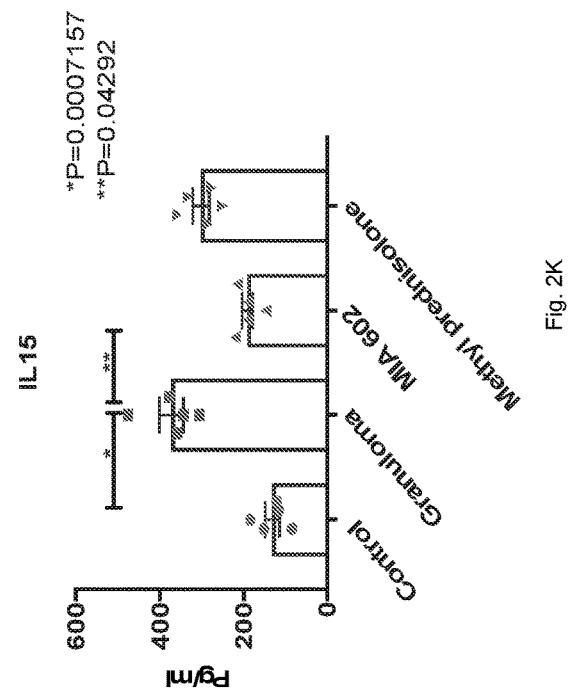
Figure 2M:
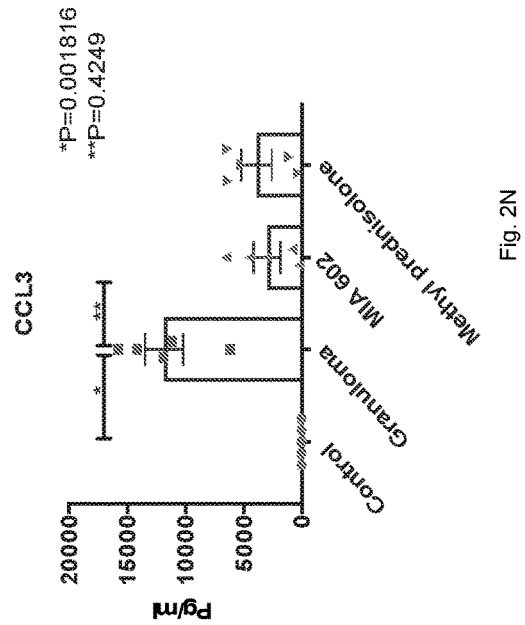
Figure 2O:
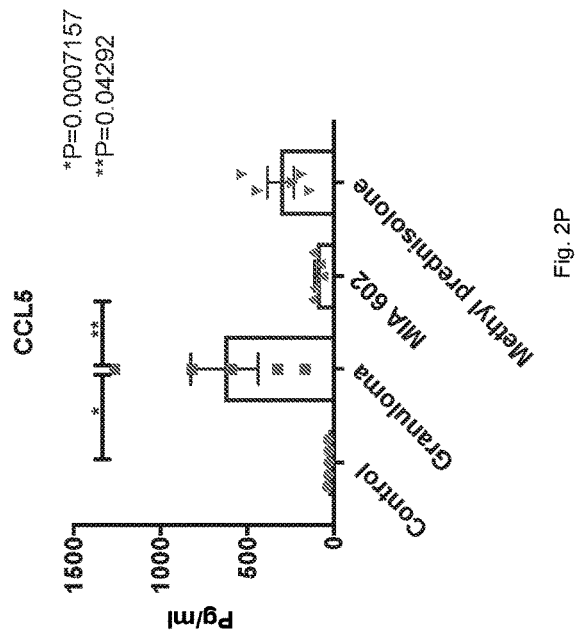
Figure 2N:
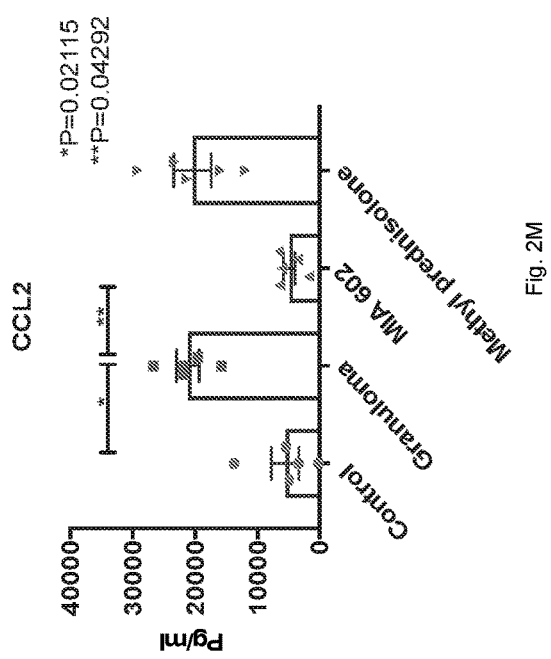
Figure 2P:
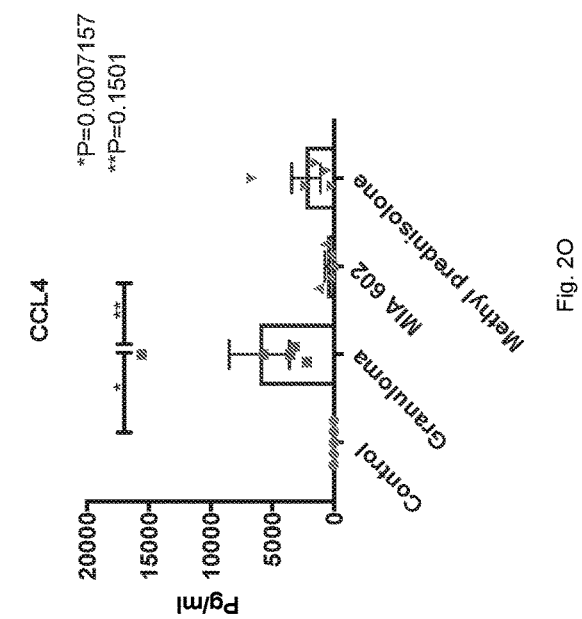
Figure 2Q:
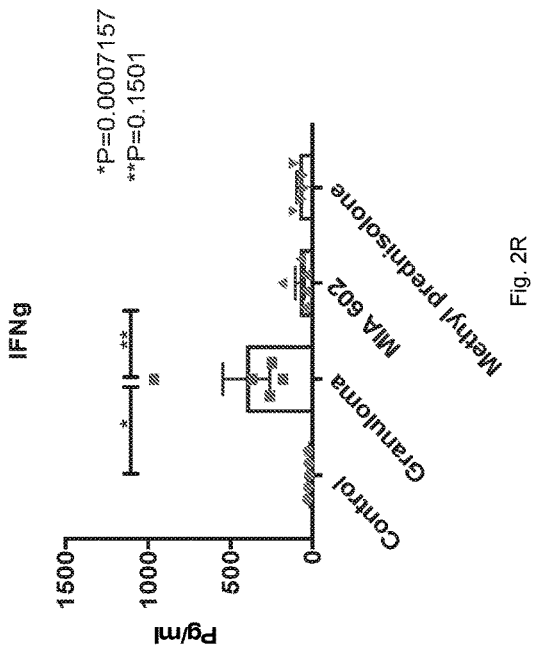
Figure 2R:
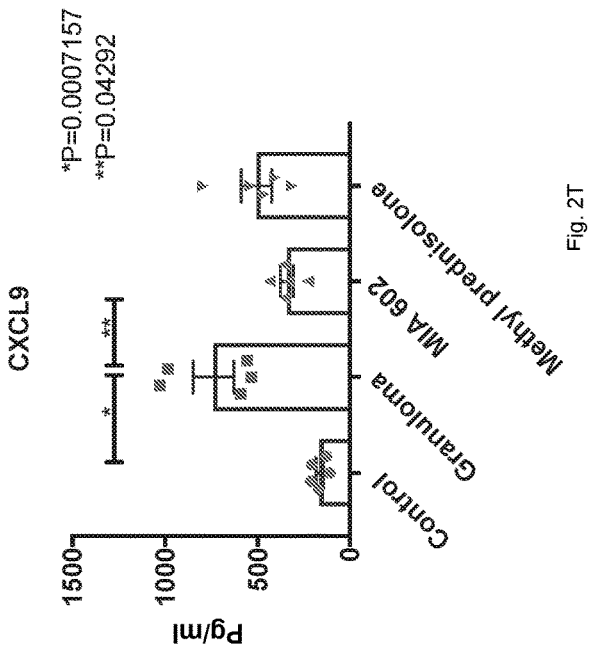
Figure 2S:
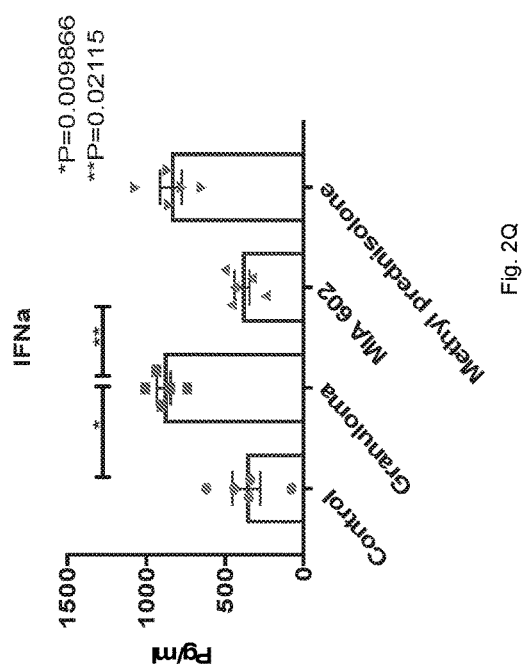

The disclosure provides a method of treating sarcoidosis (e.g., pulmonary sarcoidosis). The method comprises administering a GHRH antagonist to mammalian subject in need thereof. The data set forth herein reveals that GHRH antagonists (e.g., MIA-602) significantly reduces inflammation in an in vivo model of sarcoidosis.

The term "subject" includes, but is not limited to, human and non-human mammals such as wild, domestic and farm animals. Preferably, the subject is a human. The subject may be suffering from any form of sarcoidosis (i.e., sarcoidosis in any organ, such as the lungs).

Growth hormone-releasing hormone (GHRH) is secreted by the hypothalamus and acts on the pituitary gland to stimulate the release of growth hormone (GH). Nearly 2000 synthetic antagonistic analogs of GHRH have been produced by amino acid substitutions in the biologically active N-terminal of GHRH (1-29). Schally et al., Nat. Clin. Pract. Endocrinol. Metab. 4 (1), 33-43 (2008); Zarandi et al., PNAS 91 (25), 12298-302 (1994); Zarandi et al., Peptides 89, 60-70 (2017). The pituitary GHRH receptor (pGHRH-R) is a seven-transmembrane-domain receptor coupled to G-protein. Rekasi et al., PNAS 97 (19), 10561-6 (2000); Havt et al., PNAS 102 (48), 17424-9 (2005). The pGHRH-R, as well as its truncated splice variants (SV) is expressed in various human tissues. SV1 differs from pGHRH-R in the amino-terminal extracellular domain. Rekasi, supra.

In various aspects, the GHRH antagonist is a peptide. Various modifications of GHRH peptides confer antagonistic properties. The GHRH fragment comprising residues 1 to 29, or GHRH(1-29), is the minimum sequence necessary for biological activity on the pituitary. This fragment retains 50% or more of the potency of native GHRH. Many synthetic analogs of GHRH, based on the structure of hGH-RH(1-29)NH$_2$ peptide have been prepared are contemplated herein for use in the context of the method. hGHRH (1-29)NH$_2$ has the following amino acid sequence: Tyr-Ala-Asp-Ala-Ile$^5$-Phe-Thr-Asn-Ser-Tyr$^{10}$-Arg-Lys-Val-Leu-Gly$^{15}$-Gln-Leu-Ser-Ala-Arg$^{20}$-Lys-Leu-Leu-Gln-Asp$^{25}$-Ile-Met-Ser-Arg$^{29}$-NH$_2$ (SEQ ID NO: 1). The GHRH antagonist may comprise a GHRH peptide sequence to which amino acid deletions, insertions, and/or substitutions have been made. The GHRH antagonist may also be a fragment or modified fragment of GHRH having the capability to bind to the GHRH receptor and inhibiting the release of growth hormone. These antagonistic properties are believed to result from replacement of various amino acids and acylation with aromatic or nonpolar acids at the N-terminus of GHRH(1-29)NH$_2$.

Optionally, the GHRH antagonist is an antagonist described in U.S. Patent Publication No. 20150166617 or U.S. Pat. No. 8,691,942 (incorporated by reference herein in their entirety and particularly with respect to description of GHRH antagonists). For example, in various embodiments, the GHRH antagonist comprises the amino acid sequence (Formula I/SEQ ID NO: 2): R$^1$-Tyr$^1$-D-Arg$^2$-Asp$^3$-A$^4$-Ile$^5$-A$^6$-Thr$^7$-A$^8$-Har$^9$-A$^{10}$-A$^{11}$-A$^{12}$-Val$^{13}$-Leu$^{14}$-A$^{15}$-Gln$^{16}$-A$^{17}$-Ser$^{18}$-Ala$^{19}$-A$^{20}$-A$^{21}$-Leu$^{22}$-Leu$^{23}$-Gln$^{24}$-Asp$^{25}$-Ile$^{26}$-Nle$^{27}$-D-Arg$^{28}$-A$^{29}$-R$^2$-R$^3$—NH$_2$, wherein R$^1$ is PhAc (phenylacetyl), Nac (naphthylacetyl), Oct (octanoyl), N-Me-Aib (N-methyl-alpha-aminoisobutyroyl), Dca (dichloroacetyl), Ac-Ada (acetyl-12-aminododecanoyl), Fer (ferulyl), Ac-Amc (acetyl-8-aminoprylyl), Me-NH-Sub (methyl-NH-suberyl), PhAc-Ada (phenylacetyl 12-aminododecanoyl), Ac-Ada-D-Phe, Ac-Ada-Phe, Dca-Ada(dichloroacetyl-12-aminododecanoyl), Nac (naphthylacetyl), Nac-Ada, Ada-Ada, or $CH_3(CH_2)_{10}$—CO-Ada; $A^4$ is Ala or Me-Ala; $A^6$ is Cpa (para-chlorophenylalanine) or $Phe(F)_5$ (also known as Fpa5); $A^8$ is Ala, Pal (pyridylalanine), Dip ((3,3-diphenyl)alanine), or Me-Ala; $A^{10}$ is Fpa5, Tyr(Alk) where Alk is Me or Et; $A^{11}$ is His or Arg; $A^{12}$ is Lys, Lys(0-11) (i.e., Lys(A0-A1-A2-A3-A4-A5-A6-A7-A8-A9-A10-A11-), where each A is a lysine, otherwise described as a string of lysine residues at position $A^{12}$), $Lys(Me)_2$, or Orn (ornithine); $A^{15}$ is Abu (alpha-aminobutyric acid) or Orn; $A^{17}$ is Leu or Glu; $A^{20}$ is Har (homoarginine) or His; $A^{21}$ is Lys, $Lys(Me)_2$ or Orn; $A^{29}$ is Har, Arg or Agm (agmatine); $R_2$ is β-Ala, Amc (8-aminocaprylyl), Apa (5-aminopentanoyl), Ada (12-aminododecanoyl), $AE_2A$ (8-amino-3,6-dioxaoctanoyl), $AE_4P$ (15-amino-4,7,10,13-tetraoxapentadecanoyl), ε-Lys(α-$NH_2$) (a Lys residue, the 8-amino group of which is acylated by the carbonyl group of an N-terminally located amino acid; the α-amino group of the Lys residue is free), Agm (agmatine), or absent; and $R^3$ is Lys(Oct), Ahx (6-aminohexanoyl), or absent.

Optionally, the GHRH antagonist is MIA-602: [PhAc-$Ada^0$-$Tyr^1$, D-$Arg^2$, $Fpa5^6$, $Ala^8$, $Har^9$, $Tyr(Me)^{10}$, $His^{11}$, $Orn^{12}$, $Abu^{15}$, $His^{20}$, $Orn^{21}$, $Nle^{27}$, D-$Arg^{28}$, $Har^{29}$]hGH-RH(1-29)$NH_2$ (SEQ ID NO: 8), further described in U.S. Patent Publication No. 20150166617 (incorporated herein by reference with respect to the discussion of the structure, activity, and methods of making MIA-602, MIA-604, MIA-606, MIA-610, MIA-640, and MIA-690). Alternative GHRH antagonists include, but are not limited to, Phac-Ada-$Tyr^1$-D-$Arg^2$-$Asp^3$-$Ala^4$-$Ile^5$-$Phe(F)_5^6$-$Thr^7$-$Ala^8$-$Har^9$-Tyr(Me)$^{10}$-$His^{11}$-$Orn^{12}$-$Val^{13}$-$Leu^{14}$-$Abu^{15}$-$Gln^{16}$-$Leu^{17}$-$Ser^{18}$-$Ala^{19}$-$His^{20}$-$Orn^{21}$-$Leu^{22}$-$Leu^{23}$-$Gln^{24}$-$Asp^{25}$-$Ile^{26}$-$Nle^{27}$-D-$Arg^{28}$-$Har^{29\text{-}Agm\text{-}NH}{}_2$ (MIA-604/SEQ ID NO: 3); Phac-Ada-$Tyr^1$-D-$Arg^2$-$Asp^3$-$Ala^4$-$Ile^5$-$Phe(F)_5^6$-$Thr^7$-Me-$Ala^8$-$Har^9$-$Tyr(Me)^{10}$-$His^{11}$-$Orn^{12}$-$Val^{13}$-$Leu^{14}$-$Abu^{15}$-$Gln^{16}$-$Leu^{17}$-$Ser^{18}$-$Ala^{19}$-$His^{20}$-$Orn^{21}$-$Leu^{22}$-$Leu^{23}$-$Gln^{24}$-$Asp^{25}$-$Ile^{26}$-$Nle^{27}$-D-$Arg^{2s}$-$Har^{29}$-Agm-$NH_2$ (MIA-606/SEQ ID NO: 4); Phac-$Tyr^1$-D-$Arg^2$-$Asp^3$-$Ala^4$-$Ile^5$-$Cpa^6$-$Thr^7$-$Ala^8$-$Har^9$-$Fpa5^{10}$-$His^{11}$-$Orn^{12}$-$Val^{13}$-$Leu^{14}$-$Abu^{15}$-$Gln^{16}$-$Leu^{17}$-$Ser^{18}$-$Ala^{19}$-$His^{20}$-$Orn^{21}$-$Leu^{22}$-$Leu^{23}$-$Gln^{24}$-$Asp^{25}$-$Ile^{26}$-$Nle^{27}$-D-$Arg^{2s}$-$Har^{29}$-Ada-$NH_2$ (MIA-610/SEQ ID NO: 5); Phac-Ada-$Tyr^1$-D-$Arg^2$-$Asp^3$-$Ala^4$-$Ile^5$-$Cpa^6$-$Thr^7$-$Ala^8$-$Har^9$-$Fpa5^{10}$-$His^{11}$-$Orn^{12}$-$Val^{13}$-$Leu^{14}$-$Abu^{15}$-$Gln^{16}$-$Glu^{17}$-$Ser^{18}$-$Ala^{19}$-$His^{20}$-$Orn^{21}$-$Leu^{22}$-$Leu^{23}$-$Gln^{24}$-$Asp^{25}$-$Ile^{26}$-$Nle^{27}$-D-$Arg^{28}$-$Har^{29}$-Ada-$NH_2$ (MIA-640/SEQ ID NO: 6); Phac-Ada-$Tyr^1$-D-$Arg^2$-$Asp^3$-$Ala^4$-$Ile^5$-$Cpa^6$-$Thr^7$-$Ala^8$-$Har^9$-$Fpa5^{10}$-$His^{11}$-$Orn^{12}$-$Val^{13}$-$Leu^{14}$-$Abu^{15}$-$Gln^{16}$-$Leu^{17}$-$Ser^{18}$-$Ala^{19}$-$His^{20}$-$Orn^{21}$-$Leu^{22}$-$Leu^{23}$-$Gln^{24}$-$Asp^{25}$-$Ile^{26}$-$Nle^{27}$-D-$Arg^{28}$-$Har^{29}$-$NH_2$ (MIA-690/SEQ ID NO: 7). The amino acid sequences of the peptides described above are numbered in correspondence with the amino acid residues in hGHRH(1-29) (SEQ ID NO: 1).

The disclosure provides a method of treating sarcoidosis in a subject in need thereof. "Treating" sarcoidosis does not require a 100% remission. Any decrease in sarcoidosis or symptoms of sarcoidosis (e.g., inflammation, granuloma formation, granuloma size), in increase in quality of life, constitutes a beneficial biological effect in a subject. The progress of the method in treating sarcoidosis can be ascertained using any suitable method, such as biomarker detection/measurement in a biological (e.g., blood) sample, chest imaging (e.g., CT-scan), and PET-CT scan. In certain aspects, the method provides a reduction or improvement in a disease indicator, parameter, or symptom, such as a reduction in angiotensin converting enzyme (ACE), SIL2R, or CRP biomarkers, by at least 50%, at least 65%, at least 75%, at least 80%, at least 85%, at least 90%, at least 95% or by at least 99% as compared to pre-treatment, or a reduction in a disease indicator, parameter, or symptom by at least 50% compared to that achieved by treatment with prednisone (administered prior to the instant method or in a matched patient). In various aspects, "treatment" also includes stabilization of the disease, i.e., controlled or no further progression of the disease (e.g., granuloma burden does not increase, or increases by less than 10%, preferably less than 5%, within a given timeframe).

Alternatively or in addition, treatment as described herein optionally improves the stage of the disease or reduces the severity within a stage. Commonly used stages for sarcoidosis includes: stage I, granulomas located mainly in lymph nodes; stage II, granulomas located in lungs and lymph nodes; stage III, granulomas located mainly in lungs with shrinking lymph nodes; stage IV, pulmonary fibrosis.

Sarcoidosis disease progression is determined using any of a variety of clinical techniques, such as biopsy of the affected organ(s) to identify granulomas, blood test, bronchoscopy, X-ray, neurological tests (e.g., electromyography, evoked potentials, spinal taps, or nerve conduction tests), high-resolution computed tomography (CT) scans, magnetic resonance imaging (MRI), positron electron tomography (PET) scans, pulmonary function tests, and ultrasound.

A particular administration regimen for a particular subject will depend, in part, upon the amount of antagonist administered, the route of administration, and the cause and extent of any side effects. The amount administered to the subject (e.g., human) in accordance with the disclosure should be sufficient to affect the desired response (i.e., ameliorate, prevent or improve an unwanted condition, disease or symptom of a patient) over a reasonable time frame. A therapeutically effective amount of the GHRH antagonist is typically an amount such that when it is administered in a physiologically tolerable excipient composition, it is sufficient to achieve an effective systemic concentration or local concentration in target tissue.

The dose of GHRH antagonist is optionally about 0.005 mg/kg to about 100 mg/kg. In various aspects, the GHRH antagonist is administered in a dose of about 0.05 mg/kg to about 20 mg/kg. In some embodiments, the GHRH antagonist is administered at a dose of about 0.01 mg/kg/dose to about 50 mg/kg/dose, about 0.01 mg/kg/dose to about 25 mg/kg/dose, about 0.1 mg/kg to about 15 mg/kg, or about 1 mg/kg to about 10 mg/kg. Optionally, doses are given once a day or divided into 2-4 administrations/day. When the GHRH antagonist is administered intravenously to human patients, doses are optionally divided into 1-4 bolus injections/day or given as a continuous infusion.

The GHRH antagonist may be administered daily, at least once a week, at least twice a week, at least three times a week, at least four times a week, at least five times a week, six times a week, every two weeks, every three weeks, every four weeks, every five weeks or every six weeks. The treatment period (entailing multiple administrations of the antagonist) will depend on the nature and severity of the disease, as well as the existence of any side effects. Examples of treatment periods include, but are not limited to, 2 weeks, 3 weeks, 1 month, 2 months, 3 months, 4 months, 5 months, 6 months, 9 months, and 12 months.

Methods of administration may include, but are not limited to, oral administration and parenteral administration, including but not limited to, intradermal, intramuscular, intraperitoneal, intravenous, intraarterial, subcutaneous, epidural, sublingual, intranasal, intracerebral, intraventricular, intrathecal, intravaginal, transdermal, rectally, inhalation, intrapulmonary, intra-airway, intrabronchial, intratracheal, or topical (e.g., to the ears, nose, eyes, or skin) delivery. The antagonist is administered subcutaneously in various aspects. In other aspects, such as aspects wherein the subject suffers from pulmonary sarcoidosis, the antagonist is administered via intranasal, inhalation, intrapulmonary, intra-airway, intrabronchial, or intratracheal delivery.

Optionally, the GHRH antagonist is administered either alone or in combination (concurrently or serially) with other pharmaceuticals, optionally as a single, combined formulation or as separate compositions. In some aspects, the method comprises administering multiple GHRH antagonists. Alternatively or in addition, the GHRH antagonist is optionally administered in combination with other anti-inflammatories, such as a steroid. Alternatively or in addition, the GHRH antagonist is optionally administered in combination with one or more disease-modifying antirheumatic drugs (DMARDs; e.g., methotrexate, azathioprine, or leflunomide), a monoclonal antibody (e.g., infliximab, adalimumab, rituximab, or golimumab), colchicine, hormone therapy (e.g., corticotropin), an antibiotic, and/or pentoxifylline.

The GHRH antagonist may be administered in the form of pharmaceutically acceptable, nontoxic salts, such as acid addition salts. Illustrative of such acid addition salts are hydrochloride, hydrobromide, sulphate, phosphate, fumarate, gluconate, tannate, maleate, acetate, trifluoroacetate, citrate, benzoate, succinate, alginate, pamoate, malate, ascorbate, tartarate, and the like. Particularly preferred antagonists are salts of low solubility, e.g., pamoate salts and the like.

Formulations containing the GHRH antagonist and a suitable carrier can be solid dosage forms which include, but are not limited to, softgels, tablets, capsules, cachets, pellets, pills, powders and granules; topical dosage forms which include, but are not limited to, solutions, powders, fluid emulsions, fluid suspensions, semi-solids, ointments, pastes, creams, gels and jellies, and foams; and parenteral dosage forms which include, but are not limited to, solutions, suspensions, emulsions, and powder. In some embodiments, a single dose may comprise one or more administrations (i.e., multiple injections or multiple pills to arrive at a single dose/amount of antagonist).

The GHRH antagonist may be contained in formulations with pharmaceutically acceptable diluents, fillers, disintegrants, binders, lubricants, surfactants, hydrophobic vehicles, water soluble vehicles, emulsifiers, buffers, humectants, moisturizers, solubilizers, preservatives and the like. The means and methods for administration are known in the art and an artisan can refer to various pharmacologic references for guidance. For example, Modern Pharmaceutics, Banker & Rhodes, Marcel Dekker, Inc. (1979); and Goodman & Gilman's The Pharmaceutical Basis of Therapeutics, 6th Edition, MacMillan Publishing Co., New York (1980) can be consulted. Pharmaceutical compositions can comprise suitable solid or gel phase carriers or excipients. Examples of such carriers or excipients include but are not limited to calcium carbonate, calcium phosphate, various sugars, starches, cellulose derivatives, gelatin, and polymers such as, e.g., polyethylene glycols.

The invention, thus generally described, will be understood more readily by reference to the following example, which is provided by way of illustration and is not intended to limit the invention.

EXAMPLES

General Methods
MIA-602 Preparation

The chemical structure of MIA-602 is [PhAc-Ada$^0$, D-Arg$^2$, Fpa5$^6$, Ala$^8$, Har$^9$, Tyr(Me)$^{10}$, His$^{11}$, Orn$^{12}$, Abu$^{15}$, His$^{20}$, Orn$^{21}$, Nle$^{27}$, D-Arg$^{28}$, Har$^{29}$]hGH-RH(1-29)NH$_2$. The compound was dissolved in 100% dimethyl sulfoxide (DMSO, ACS grade, Sigma) for stock, and diluted at 1:1000 in corresponding culture medium to a final concentration of 1 µM. Control group in vitro and in vivo received placebo with the same volume and concentration of DMSO.

Microparticle Development

Microparticles were produced as previously presented (Zhang et al., *Sci Rep* 2020; 10: 7277). Microparticles were generated from a rough colony of a clinical strain of *Mycobacterium abscessus* (MAB) with sonicating and heating live bacilli. High quality images of non-infectious, MAB particles were obtained by scanning electron microscope (SEM).

Human Blood Sample

Blood samples were collected from nine patient with confirmed pulmonary sarcoidosis, randomly selected from the University of Miami Sarcoidosis Biobanking, and matched by age, sex and race with then healthy controls. To avoid the inconvenience and risks associated with additional venipunctures, a 10 ml blood specimen was collected. Patients who currently had a hgb<7 mg/dL were excluded from participating in this study.

Maturing In-Vitro Granuloma Like Formation

In vitro granuloma was developed by challenging PBMC with microparticles as previously described (Zhang et al., Sci Rep 2020; 10: 7277).

Mouse Model Exposure to MAB Microparticles

Granulomatous reaction in the mouse lung was developed as previously described (Zhang et al., *Front Immunol* 2019; 10: 2888).

ELISA (Zhang et al., *Sci Rep* 2020; 10: 7277), PBMCs were lysed in lysis buffer (Cell Signaling Technology, Beverly, MA) with protease inhibitor cocktail (Cell Signaling Technology, Beverly, MA) and sonicated three times for 2 seconds each with at least 1-min rest on ice between each 2-s pulse. Samples were centrifuged at 10,000×g for 5 min at 4° C. and the supernatant was collected. Protein concentration was determined by BCA protein assay kit from Cell Signaling Technology. The methodology is further described in .Zhang et al., *Sci Rep* 2020; 10: 7277.

Thirty micrograms of total protein were mixed in a reducing sample buffer and used for mitochondrial apoptosis assay per the kit instruction. The assay was performed using a Bio-Rad kit (171-WAR3CK).

To measure cytokines in media, supernatant aliquot samples were analyzed, thawed, and spun at 12,000 rpm for 10 min to separate the particulate material at the bottom. Fifty µl of undiluted media was plated from each sample onto a 96-well V-bottom plate (source plate) by manual pipetting according to predefined maps. The aliquots were wrapped in parafilm and kept in a humid chamber at 4° C. during the entire process, but not longer than 72 hr. Growth factors and their receptor's capture antibodies were reconstituted and diluted per manufacturer specification and 50 µl plated into each well of respective 96-well high-binding half-well plates, which were then sealed and incubated overnight at 4° C. The cytokine levels were measured using a procartaplex human th1/th2 cytokine panel 11 plex from Invitrogen, (epx110-10810-901).

Immunofluorescence Confocal Microscopy

The detail of the methodology used for confocal microscopy is discussed in Zhang et al., Front Immunol 2019; 10: 2888. To summarize, mice were killed on day 14, and the left lungs were harvested. Lungs were filled with 10% buffered formalin and fixed in formalin for at least 72 h before IHC staining. H&E staining was used to determine inflammatory pathology.

For immunofluorescence, paraffin-embedded serial sections (5 μm) first underwent standard deparaffinization and rehydration procedures, Sections were then probed with GHRHR (Origene, cat # TA311715) as primary antibody, and anti-Rabbit antibody from Sigma, (cat # F-9887) as secondary. Nuclei were counterstained with DAPI. All reagents were from Sigma-Aldrich. Tissue sections were analyzed using fluorescence microscopy and ImageJ software (version 6.0; NIH) to quantitate fluorescent intensity. In trichrome-stained slides, blue stain (collagen content) was also quantitatively analyzed using ImageJ.

Confocal immunofluorescence images were acquired using a Leica DM6000 microscope with a SP5 confocal module at the University of Miami McKnight Analytical Imaging Core Facility. Captured images were processed using Velocity Software version 6.1.1 software (Perkin-Elmer, Waltham, MA).

For immunohistochemistry, 5-μm paraffin sections were processed by deparaffinization and rehydration followed by endogenous peroxidase blocking (1% $H_2O_2$ in methanol for 20 minutes) and antigen retrieval (boiled in 10 mM citrate buffer for 30 minutes). Tissue sections were blocked with 2% goat or horse serum (Vector Laboratories) and incubated with antibody CD68 (Proteintech, Cat#25747-1-AP), PD-1 (Cell Signaling, cat #84651), PD-L1 (Proteintech, Cat#17952-1-AP), CD30 (Lsbio, cat# LS-c162069) CD3 (Cell Signaling, cat#99940), iNOS (Invitrogen, cat #PAI-036), or Nitrotyrosine (Novus, NBP2-54606) over night at 4° C., washed with TBST five times, then exposed to secondary antibodies (Vector Laboratories, cat# PI-2000). Immunoreactivity was detected using the ABC Elite kit (Vector Laboratories). DAB was used as final chromogen and hematoxylin as the nuclear counterstain. Negative controls for all antibodies were made by replacing the primary antibody with non-immunogen IgG.

Lung inflammation was scored using the three fields with the highest infiltrate's intensity at 100× power magnification as previously described (Zhang et al., Front Immunol 2019; 10: 2888). The area of inflammation was measured and averaged for the three examined high-power fields.

RNA Isolation and Analysis

RNA from mouse lungs were extracted using RNA Miniprep Plus Kit (Zymo Research). Briefly, whole lung was homogenized in TRI reagent and total RNA extraction was performed following the instructions provided by the manufacturer with additional DNase treatment. Quantity and quality of the samples were determined by NanoDrop spectrophotometer and Agilent Bioanalyzer 2100, respectively (Zhang et al., Front Immunol 2019; 10: 2888).

Preparation and sequencing of RNA libraries was performed. Briefly, total RNA quantity and quality were determined using the Agilent Bioanalyzer. At least 300 ng of total RNA was used as input for the KAPA RNA HyperPrep Kit with RiboErase (HMR) according to manufacturer's protocol to create ribosomal RNA-depleted sequencing libraries. Sequencing was performed on the Illumina NextSeq 500, generating ~40 million single-end 75 base reads per sample. Sequencing data were processed with a bioinformatics pipeline including quality control, alignment to the hg19 human reference genome, and gene quantification. Count data was inputted into edgeR software for differential expression analysis. Counts were normalized using the trimmed mean of M-values (TMM) method to account for compositional difference between the libraries and paired differential expression analysis using a generalized linear model with sample as a blocking factor. Genes were considered statistically different with a false discovery rate p-value (FDR) <0.05.

Flow Cytometry

Mice were sacrificed on day 14, and the left lungs were harvested for pathology after perfusing the right ventricle with 10 ml of PBS.

The upper half of left lung tissue (without trachea, main bronchus and branches) was removed and rinsed by PBS to clean off blood. The tissue was minced and dispersed with a scissors to increase total surface area. To develop single cell suspension, the rubber end of a 5 ml plastic syringe was used to mesh cells through a 100 μm cell strainer with continuous rinse using ice-cold RPMI 1640. Cell suspension was again meshed through a 70 μm cell strainer and rinsed thoroughly with 3 ml of washing buffer containing DNAse followed by 15 ml of DNAse-free washing buffer. The sample was centrifuged at 286×g and 18° C. for 5 min, and the supernatant was discarded (Posel et al. J Vis Exp 2016: 53658).

The cells ($10^6$ cells/ml) were resuspended in 100 μl protein blocking solution with 5 μl fluorescent conjugated antibodies, CD8 (Biolegend Cat#100714, CD45 (Biolegend Cat#103130), CD68 (Biolegend Cat#137004), PD-1 (Biolegend Cat#135219), PD-L1 (Biolegend Cat#124308), CD4 (Biolegend Cat#100510), CD11b (Biolegend Cat#101243), CD11c (Biolegend Cat#117318), F4/80 (Biolegend Cat#123146), or IFNg (Biolegend Cat#505836). Samples were analyzed on a BD LSR II flow cytometer using BD FACSDiva software, and data analysis was performed using Flowjo software (TreeStar, Ashland, Oreg.). Cell populations were identified using sequential gating strategy; the expression of activation markers was presented as median fluorescence intensity. Lung immune cells were classified based on FC marker expression as previously described (Misharin et al., Am J Respir Cell Mol Biol 2013; 49: 503-510).

Example 1

The following example demonstrates treatment of sarcoidosis in vivo using a GHRH antagonist of the disclosure.

A mouse model of pulmonary sarcoidosis was established in C57Bl/6 mice by administering microparticles intratracheally. The tongue was pulled out with a small spatula and microparticles were inserted into the trachea using a 20 G angio-catheter tube at the time of laryngeal opening and advanced to main bronchus until reach to resistant. After tube placement, microparticles were administered: a first dose of $5×10^8$ CFU of M. abscessus in 50 μL with three subsequent doses of $2×10^8$ CFU of M. abscessus in 20 μL. A control group received only 20 μL PBS intratracheally. Mice receiving microparticles developed noncaseating granuloma in the lung, as observed use H&E staining and immunohistochemistry staining for CD68 macrophage marker, CD4 marker, and PD-L1.

Four groups of mice demonstrating pulmonary sarcoidosis were established alongside a fifth non-treated group which served as a control exhibiting no sarcoidosis. The first sarcoidosis group received MIA-602 (5 μg/day), administered via intraperitoneal injection. The second sarcoidosis group received α-melanocyte stimulating hormone (α-MSH), the third sarcoidosis group received steroid treatment (methyl-prednisone, the current first line treatment for sarcoidosis), and the fourth group received only saline. Mice were sacrificed after two weeks, and inflammation in lung samples was graded. As shown in FIGS. 1A-E, the untreated sarcoidosis group exhibited significant inflammation in the lung. The sarcoidosis groups treated with MIA-602 and a-MSH had lower inflammation scores. Steroid treatment did not affect inflammation.

The results described above demonstrate for the first time that a growth hormone releasing hormone receptor antagonist (here, MIA-602) is effective in treating sarcoidosis.

Example 2

The following example demonstrates that a peptide of the disclosure positively affects cytokine profiles of treated granuloma.

Granuloma and PBMC were collected from five sarcoidosis subjects. The samples were grouped as control (not challenged), granuloma group challenged with a 10:1 treatment with microparticles but left untreated, challenged granuloma group treated with 1 microM MIA-602 in vitro, and challenged granuloma group treated with methyl prednisolone in vitro. Media were removed 48 h after of treatments. Cytokines were measured using an multiplex ELISA instrument.

Figure 2T:
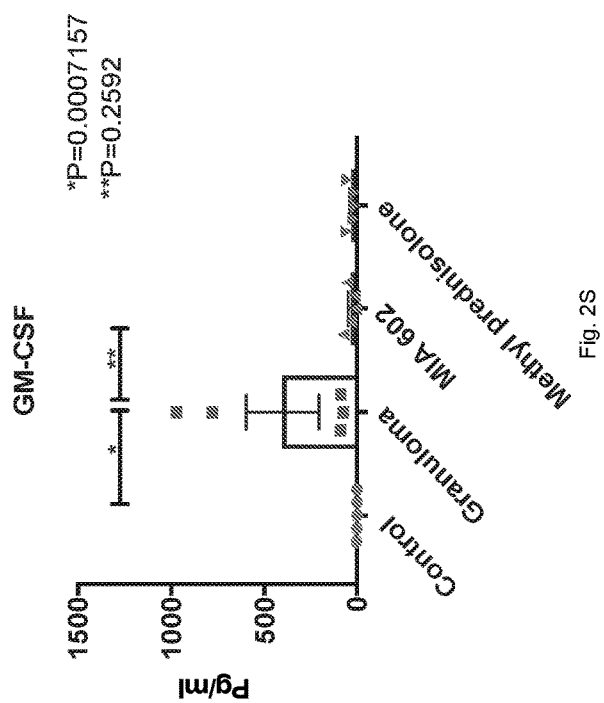

There were significant differences in expression of several cytokines in granuloma in comparison with PBMC. MIA-602 significantly reduced cytokine production of IL2, IL7, IL10, IL12, IL15, IL17A, CCL2, CCLS, IFNα, and CXCL9 in granuloma. See FIGS. 2A-2T.

Example 3

The ability of a peptide of the disclosure, MIA-602, to influence respiration and apoptosis in granuloma cells was examined. The specific processes of apoptosis and mitochondrial dynamics in granuloma have not been fully elucidated. To test if MIA-602 had pro- or anti-apoptotic effects, the protein levels of pro-(active caspase-3) and anti-apoptotic factors (survivin, Bcl-xL/Bak dimer, and Mcl-1/Bak dimer) were measured in an in vitro granuloma model. PBMCs from five confirmed sarcoidosis subjects were grouped as control (not challenged), granuloma group challenged with 10:1 treatment with microparticles generated from M. abscessus cell wall, granuloma group treated with 1 μM of MIA-602, and a granuloma group treated with methyl prednisolone (138 μM). Media were removed 48 h after treatment.

Figure 3A:
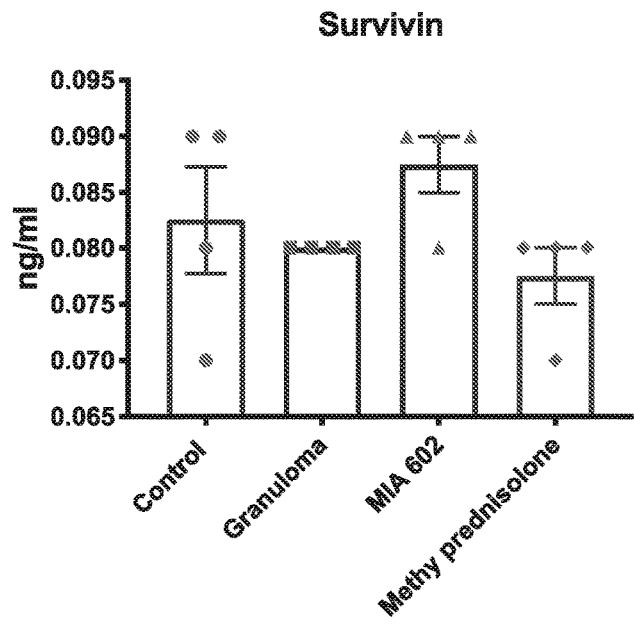
FIGS. 3A-3D: Bar graphs illustrating the percentage of levels of Survivin (FIG. 3A), Mcl-1/Bak dimer (FIG. 3B), Bcl-xL/Baak dimer (FIG. 3C) and active caspase-3 (FIG. 3D) in in vitro granuloma samples following treatment with MIA-602, methyl prednisolone, or control.
Figure 3B:
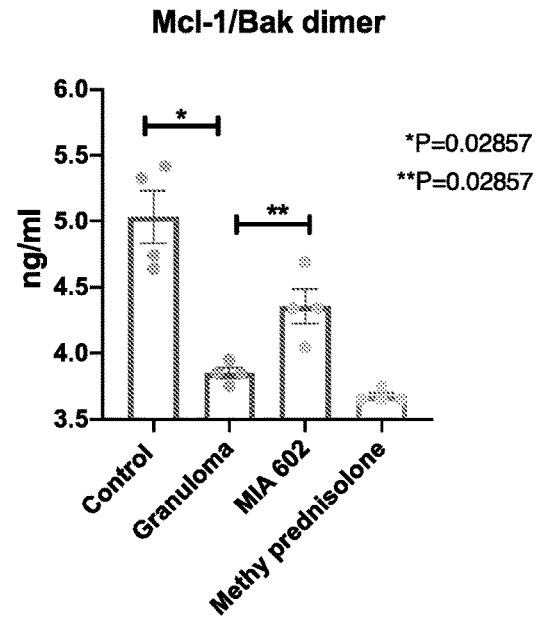
Figure 3C:
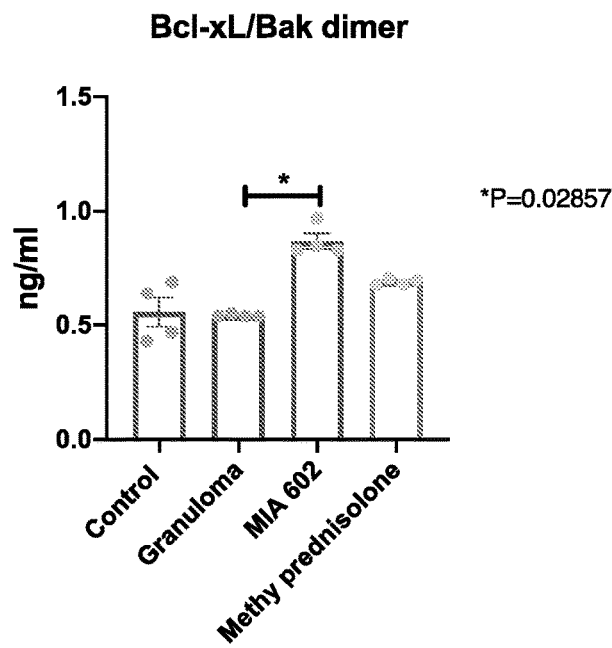
Figure 3D:
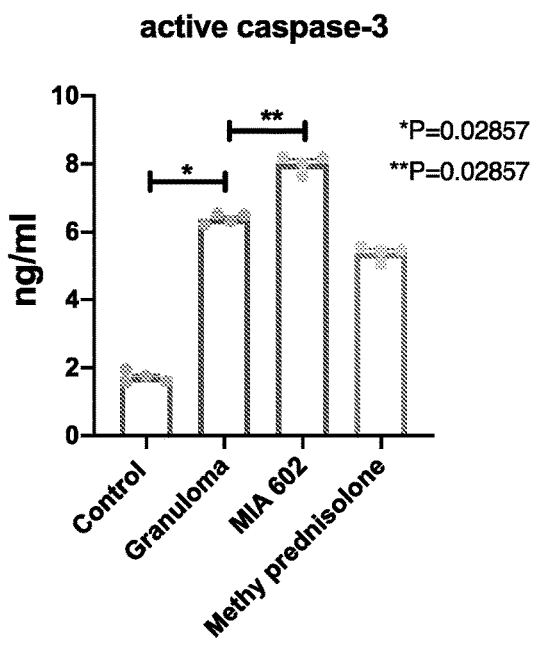

As shown in FIG. 3A, survivin levels showed no statistical difference between groups. The level of Mcl-1/Bak dimer was significantly reduced in untreated granuloma, but was restored with MIA-602 treatment (FIG. 3B). BclxL/Bak Dimer levels increased in granuloma treated with MIA-602 in comparison with granuloma treated with saline (FIG. 3C). Active caspase 3 level significantly increased in granuloma compared to PBMC, possibly due to lymphocyte early activation (Zhang C et al., Sci Rep 2020; 10: 7277). MIA-602 further increased active caspase 3 (FIG. 3D). These data suggest that treatment with a GHRHR antagonist did not increase apoptosis in granuloma.

Example 4

A mouse pulmonary granulomatous model was established for studying type I IFN pathways after exposure to M. abscessus cell wall. The model is applicable for pulmonary sarcoidosis studies due to its characteristics of noninfectious lung granulomatous model. C57Bl/6 mice were used to develop the model (Zhang et al., Front Immunol 2019; 10: 2888).

Mice were treated with 5 μg of a peptide of the disclosure, MIA-602, per day via intraperitoneal injection. After two weeks, the mice were sacrificed, and lung inflammation was graded by a lung pathologist. Lung samples were stained with H&E, CD68, PD1, PD-L1, and CD30, and scored based on percentage of cells expressing each marker.

Figure 4:
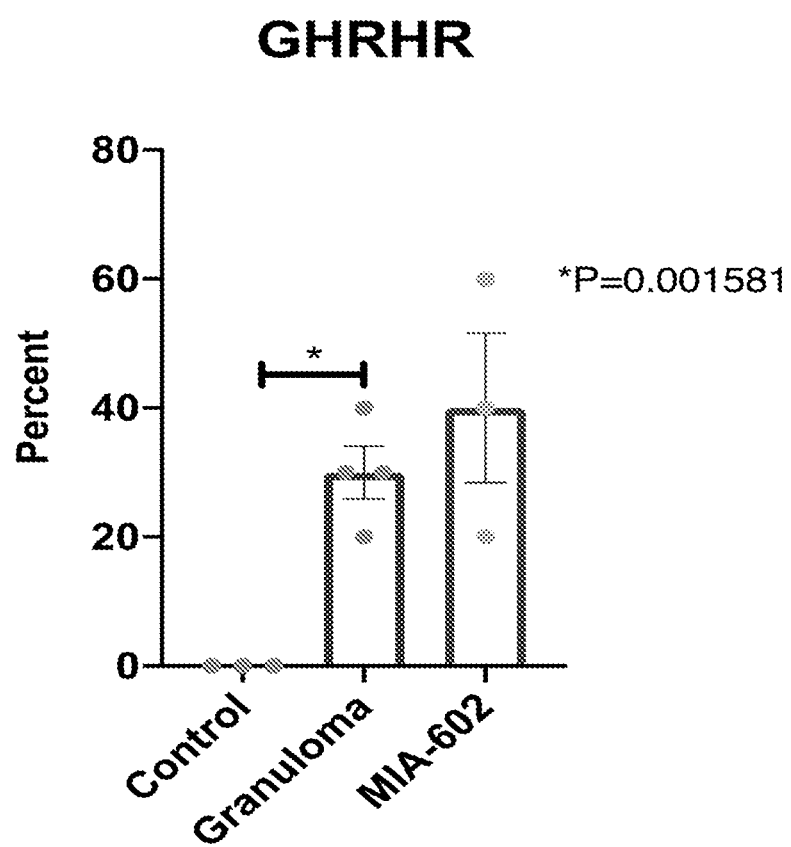
FIG. 4: Bar graph showing the percentage GHRHR immunofluorescence staining in mice lung with developed sarcoid-like granuloma challenged with microparticles versus granuloma treated with saline or control.
Figures 5A, 5B, 5C, 5D, 5E:
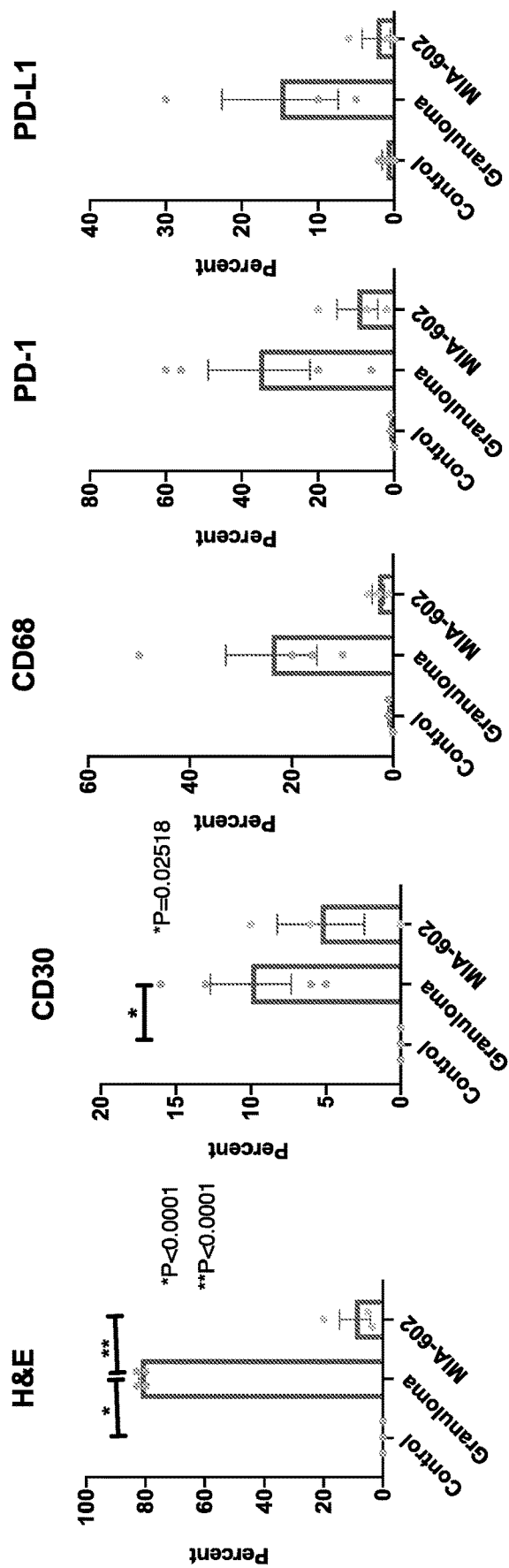
FIGS. 5A-5E: Bar graphs showing H&E (FIG. 5A) and immunohistochemistry (IHC) changes for CD30 (FIG. 5B), CD68 (FIG. 5C), PD-1 (FIG. 5D), PD-L1 (FIG. 5E) in the lungs of mice for control, with granuloma and treated with saline, and granuloma treated with MIA 602. Number of mice: control #3, granuloma #4, MIA 602 #3.

As shown in FIG. 4, the granuloma group had significant inflammation in the lung, but mice treated with MIA-602 had lower inflammation scores. FIG. 4 shows quantification of the GHRHR immunofluorescence staining following MIA-602 treatment in the granulomatous reaction of mice lung.

The inflammation score of lungs was significantly higher in the granuloma group. Lung inflammation was almost normalized in mice that received treatment with MIA-602, as shown in FIGS. 5A-5E. CD30 cells were statistically significantly increased in lung with granuloma, and nonsignificantly reduced in MIA-602 treated mice. The percentage of CD68+ cells in the lung increased in granuloma-afflicted subjects and decreased in MIA-602-treated subjects, but the changes were not statistically significant. This pattern was seen in PD-1+- and PD-L1+ cells in the granuloma group and the MIA-602-treated group.

This animal model study confirmed that GHRHR significantly increased in sarcoidosis lung. MIA-602 has anti-inflammatory properties that reduced inflammatory cell numbers significantly in lung tissue.

Example 5

Figure 6A:
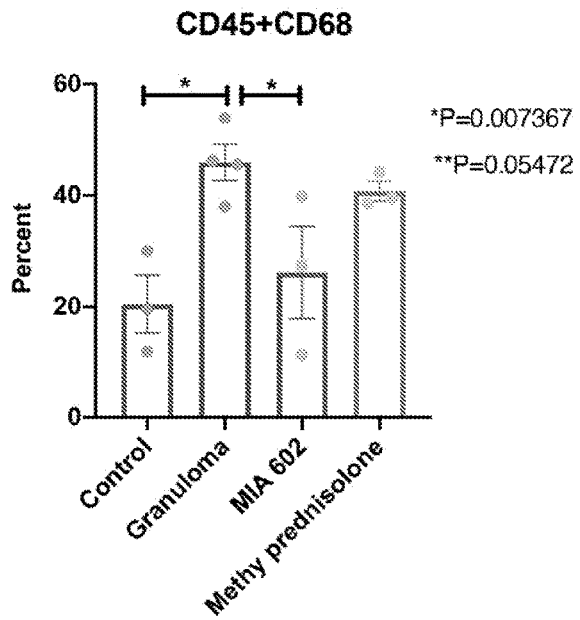
FIGS. 6A-6C: Bar graphs illustrating the percent increase of CD45+CD68+, CD45+CD68+PD-1, or CD45+CD68+ PD-L1 cells in granuloma in control mice, mice treated with MIA 602, and mice treated with methyl prednisolone. The percent increase of CD45+CD68+PD-L1 cells was higher after treatment with MIA-602 compared to the other cell types.

Flow cytometry showed that CD68+ cells reduced after MIA-602 therapy in the sarcoidosis mice model. Mice were grouped as control, challenged with microparticles and treated with saline, challenged and treated with MIA-602 (5 μg), and challenged and treated with methyl prednisolone (100 μg). After two weeks, lungs were harvested from all groups, and lung single cells were generated for flow cytometry analysis. As shown in FIG. 6A, the population of CD45+CD68 cells significantly increased in challenged mice, and the population was significantly reduced by MIA-602 treatment.

Figure 6B:
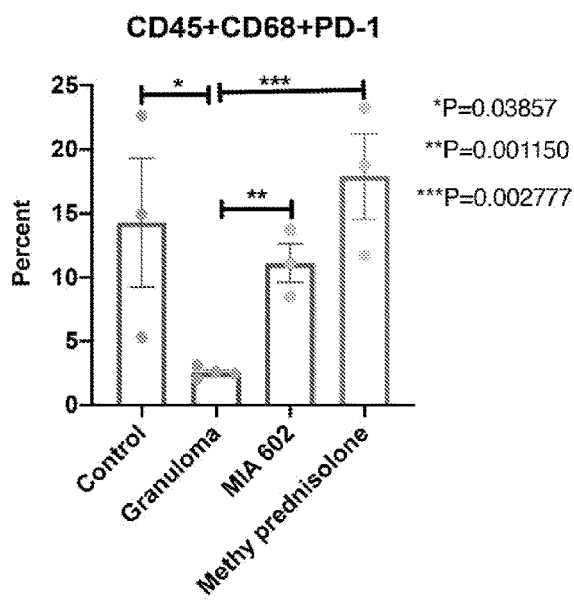

It was hypothesized that MIA-602 will restore the number of CD68+ cells that express PD-1. FIG. 6B shows that the number of CD45+CD68+ cells that expressed PD-1 were significantly reduced in challenged mice with granulomatous reaction in lungs. The percentage of these cells significantly increased following MIA-602 treatment.

Figure 6C:
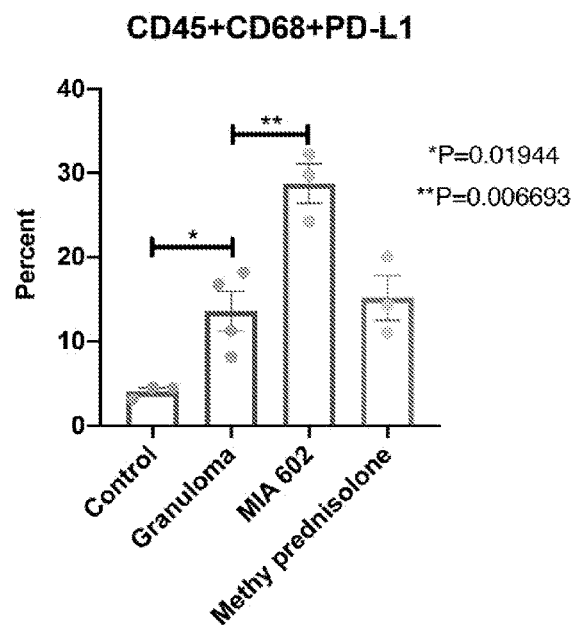

To confirm that mice lung with granuloma shows higher percentage of CD45+CD68+ that expressed PD-L1, lung single cells were stained in all experimental groups. As shown in FIG. 6C, the population of CD45+CD68+PD-L1 cells significantly increased in granuloma, and a higher percentage was detected after treatment with MIA-602. The anti-inflammatory effects of MIA-602 were mainly through reduction in CD68+ cells, and PD-1 and PD-L1 play role on this process.

Example 6

Figure 7:
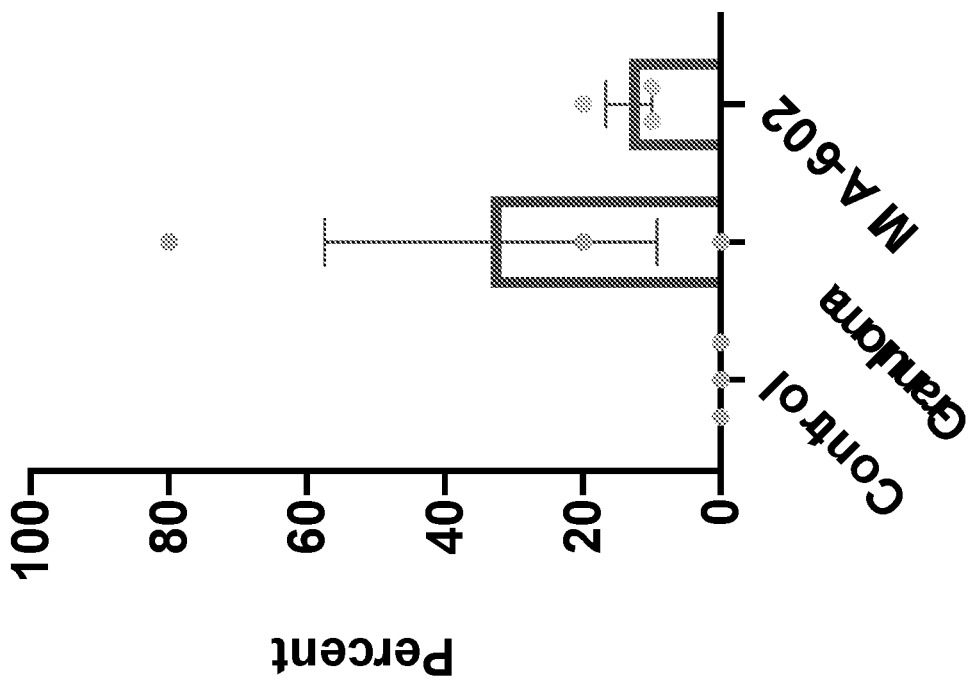
FIG. 7: Bar graph showing the percent NOS2 staining in a control mouse lung (without granuloma), the lung of a mouse challenged with microparticles and having developed granuloma, and the lung of a mouse having granuloma and treated with MIA-602.

Inducible nitric oxide synthases (iNOS) produces nitric oxide and has a crucial role in granuloma development. iNOS is expressed in macrophages after exposure to bacterial lipopolysaccharides and IFNγ (Facchetti et al., *Am J Pathol* 1999; 154: 145-152). To understand MIA-602's effects on nitric oxide response, iNOS and nitrotyrosine (as an indicator of NO function) were detected by staining mice lung challenged with microparticles (sarcoidosis model) and injected with saline daily, those that were treated with daily intraperitoneal injection of MIA-602 (5 μg), and a control group which were not challenged and did not receive MIA-602. Lung tissue was harvested after three weeks and tissue stained with NOS2 and nitrotyrosine. As shown in FIG. 7, NOS2 expression was increased in sarcoid-like granuloma and then reduced following MIA-602 treatment. The finding was not statistically significant.

Figure 8:
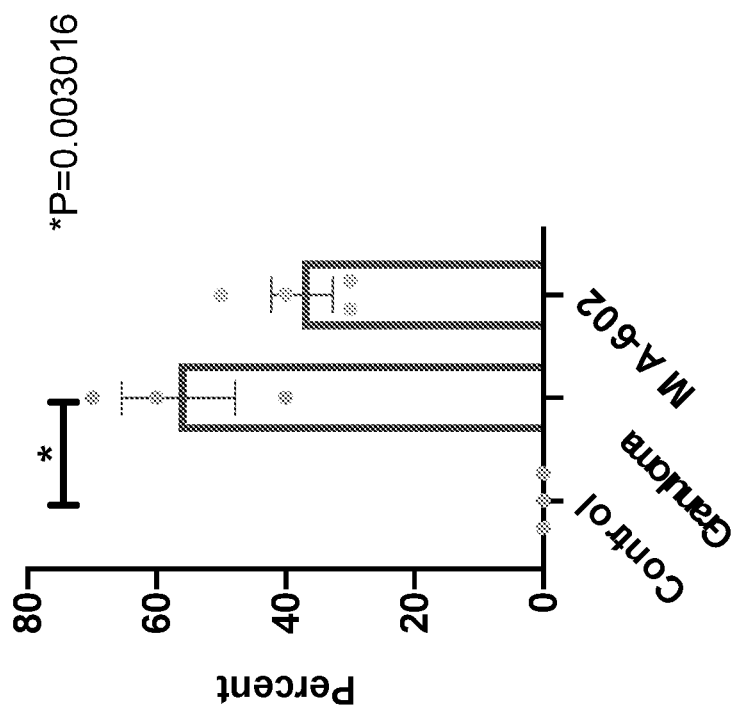
FIG. 8: Bar graph showing the percent Nitrotyrosine staining in a control mouse lung (without granuloma), the lung of a mouse challenged with microparticles and developed granuloma, and the long of a mouse mouse having granuloma and treated with MIA-602.

Nitrotyrosine expression was statistically significantly increased in the lung of mice with sarcoid-like granuloma as shown in FIG. 8. Treatment with MIA-602 reduced the nitrotyrosine levels, but the reduction was not statistically significant.

Challenge with microparticles activated iNOS and increased nitrotyrosine in the lungs. MIA-602 reduced both, but not in a statistically significant manner, in these experiments. These experiments suggest an anti-nitrosative effects of MIA-602 in sarcoidosis mice model.

Example 7

Transcriptomics changes in the sarcoidosis mice model was examined. RNA was extracted from the lungs of mice challenged with microparticles (sarcoidosis model) and injected with saline daily or treated with daily intraperitoneal injection of MIA-602 (5 μg), or extracted from a control group that was never challenged and did not receive MIA-602. RNA was isolated from lung tissue over the course of three weeks, and RNASeq was performed. 778 genes were upregulated, and 293 genes were downregulated (508 protein coding, or TEC genes and rest noncoding) in mice with granuloma that were treated with daily MIA-602 compared to those with granuloma that were treated with saline. Genes that exhibited more than 2.5-fold differential expression upon treatment with MIA-602 are provided as FIG. 9. In various aspects, the disclosure provides a method of characterizing a subject's response to sarcoidosis treatment, wherein the method comprises measuring the expression of one or more of the genes set forth in FIG. 9. In various aspects, a 2.5-fold differential expression compared to the level of expression prior to treatment indicates a therapeutic response to treatment (i.e., the disorder is treated, one more symptoms of the disorder are alleviated, etc.).

The entire document is intended to be related as a unified disclosure, and it should be understood that all combinations of features described herein are contemplated, even if the combination of features are not found together in the same sentence, or paragraph, or section of this document. In addition, the invention includes, as an additional aspect, all embodiments of the invention narrower in scope in any way than the variations specifically mentioned above. With respect to aspects of the invention described or claimed with "a" or "an," it should be understood that these terms mean "one or more" unless context unambiguously requires a more restricted meaning. With respect to elements described as one or more within a set, it should be understood that all combinations within the set are contemplated. If aspects of the invention are described as "comprising" a feature, embodiments also are contemplated "consisting of" or "consisting essentially of" the feature.

Although the applicant(s) invented the full scope of the claims appended hereto, the claims appended hereto are not intended to encompass within their scope the prior art work of others. Therefore, in the event that statutory prior art within the scope of a claim is brought to the attention of the applicants by a Patent Office or other entity or individual, the applicant(s) reserve the right to exercise amendment rights under applicable patent laws to redefine the subject matter of such a claim to specifically exclude such statutory prior art or obvious variations of statutory prior art from the scope of such a claim. Variations of the invention defined by such amended claims also are intended as aspects of the invention. Additional features and variations of the invention will be apparent to those skilled in the art from the entirety of this application, and all such features are intended as aspects of the invention.

All publications, patents and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method of treating sarcoidosis, the method comprising administering a GHRH antagonist to mammalian subject in need thereof.

2. The method of claim 1, wherein the GHRH antagonist comprises the amino acid sequence (Formula I/SEQ ID NO: 2): $R^1$-Tyr$^1$-D-Arg$^2$-Asp$^3$-A$^4$-Ile$^5$-A$^6$-Thr$^7$-A$^8$-Har$^9$-A$^{10}$-A$^{11}$-A$^{12}$-Val$^{13}$-Leu$^{14}$-A$^{15}$-Gln$^{16}$-A$^{17}$-Ser$^{18}$-Ala$^{19}$-A$^{20}$-A$^{21}$-Leu$^{22}$-Leu$^{23}$-Gln$^{24}$-Asp$^{25}$-Ile$^{26}$-Nle$^{27}$-D-Arg$^{28}$-A$^{29}$-R$^2$-R$^3$—NH$_2$, wherein $R^1$ is PhAc (phenylacetyl), Nac (naphthylacetyl), Oct (octanoyl), N-Me-Aib (N-methyl-alpha-aminoisobutyroyl), Dca (dichloroacetyl), Ac-Ada (acetyl-12-aminododecanoyl), Fer (ferulyl), Ac-Amc (acetyl-8-aminocaprylyl), Me-NH-Sub (methyl-NH-suberyl), PhAc-Ada (phenylacetyl 12-aminododecanoyl), Ac-Ada-D-Phe, Ac-Ada-Phe, Dca-Ada(dichloroacetyl-12-aminododecanoyl), Nac-Ada, Ada-Ada, or CH$_3$(CH$_2$)$_{10}$—CO-Ada;

$A^4$ is Ala or Me-Ala;

$A^6$ is Cpa (para-chlorophenylalanine) or Phe(F)$_5$;

$A^8$ is Ala, Pal (pyridylalanine), Dip ((3,3-diphenyl)alanine), or Me-Ala;

$A^{10}$ is Fpa5 or Tyr(Alk) where Alk is Me or Et;

$A^{11}$ is His or Arg; $A^{12}$ is Lys, a string of 2 to 11 lysine residues Lys(Me)$_2$, or Orn (ornithine);

$A^{15}$ is Abu (alpha-aminobutyric acid) or Orn;

$A^{17}$ is Leu or Glu;

$A^{20}$ is Har (homoarginine) or His;

$A^{21}$ is Lys, Lys(Me)$_2$ or Orn;

$A^{29}$ is Har, Arg or Agm (agmatine);

$R_2$ is β-Ala, Amc (8-aminocaprylyl), Apa (5-aminopentanoyl), Ada (12-aminododecanoyl), AE$_2$A (8-amino-3,6-dioxaoctanoyl), AE$_4$P (15-amino-4,7,10,13-tetraoxapentadecanoyl), ε-Lys(α-NH$_2$), wherein the ε-amino group of ε-Lys(α-NH$_2$) is acylated by the carbonyl group of an N-terminally located amino acid and the α-amino group of the ε-Lys(α-NH$_2$) is free, Agm (agmatine), or absent; and $R^3$ is Lys(Oct), Ahx (6-aminohexanoyl), or absent.

3. The method of claim 1, wherein the GHRH antagonist is MIA-602, MIA-604, MIA-606, MIA-610, MIA-640, or MIA-690.

4. The method of claim 1, wherein the GHRH antagonist is MIA-602.

5. The method of claim 1, wherein the GHRH antagonist is administered via intradermal, intramuscular, intraperitoneal, intravenous, intraarterial, subcutaneous, epidural, sublingual, intranasal, intracerebral, intraventricular, intrathecal, intravaginal, transdermal, rectally, inhalation, intrapulmonary, intra-airway, intrabronchial, intratracheal, or topical delivery.

6. The method of claim 5, wherein the GHRH antagonist is administered via intranasal, inhalation, intrapulmonary, intra-airway, intrabronchial, or intratracheal delivery.

7. The method of claim 3, wherein the GHRH antagonist is administered via intradermal, intramuscular, intraperitoneal, intravenous, intraarterial, subcutaneous, epidural, sublingual, intranasal, intracerebral, intraventricular, intrathecal, intravaginal, transdermal, rectally, inhalation, intrapulmonary, intra-airway, intrabronchial, intratracheal, or topical delivery.

8. The method of claim 7, wherein the GHRH antagonist is administered via intranasal, inhalation, intrapulmonary, intra-airway, intrabronchial, or intratracheal delivery.

9. The method of claim 4, wherein the GHRH antagonist is administered via intradermal, intramuscular, intraperitoneal, intravenous, intraarterial, subcutaneous, epidural, sublingual, intranasal, intracerebral, intraventricular, intrathecal, intravaginal, transdermal, rectally, inhalation, intrapulmonary, intra-airway, intrabronchial, intratracheal, or topical delivery.

10. The method of claim 9, wherein the GHRH antagonist is administered via intranasal, inhalation, intrapulmonary, intra-airway, intrabronchial, or intratracheal delivery.

11. The method of claim 1, wherein the sarcoidosis is pulmonary sarcoidosis.

12. The method of claim 3, wherein the sarcoidosis is pulmonary sarcoidosis.

13. The method of claim 4, wherein the sarcoidosis is pulmonary sarcoidosis.

14. The method of claim 6, wherein the sarcoidosis is pulmonary sarcoidosis.

15. The method of claim 8, wherein the sarcoidosis is pulmonary sarcoidosis.

16. The method of claim 10, wherein the sarcoidosis is pulmonary sarcoidosis.

\* \* \* \* \*